(12) United States Patent
Battula et al.

(10) Patent No.: US 9,846,160 B2
(45) Date of Patent: Dec. 19, 2017

(54) GANGLIOSIDE GD2 AS A MARKER AND TARGET ON CANCER STEM CELLS

(71) Applicant: Board of Regents, The University of Texas System, Austin, TX (US)

(72) Inventors: Venkata Battula, Houston, TX (US); Michael Andreeff, Houston, TX (US); Sendurai A. Mani, Houston, TX (US); Tapasree Roy Sarkar, Houston, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 313 days.

(21) Appl. No.: 14/380,807

(22) PCT Filed: Feb. 27, 2013

(86) PCT No.: PCT/US2013/028016
§ 371 (c)(1),
(2) Date: Aug. 25, 2014

(87) PCT Pub. No.: WO2013/130603
PCT Pub. Date: Sep. 6, 2013

(65) Prior Publication Data
US 2015/0044233 A1 Feb. 12, 2015

Related U.S. Application Data

(60) Provisional application No. 61/603,789, filed on Feb. 27, 2012.

(51) Int. Cl.
| | | |
|---|---|---|
| G01N 33/574 | (2006.01) | |
| A61K 31/513 | (2006.01) | |
| A61K 31/4192 | (2006.01) | |
| A61K 39/395 | (2006.01) | |
| C07K 16/30 | (2006.01) | |
| A61K 31/4196 | (2006.01) | |
| A61K 45/06 | (2006.01) | |
| A61K 39/00 | (2006.01) | |

(52) U.S. Cl.
CPC ... *G01N 33/57492* (2013.01); *A61K 31/4192* (2013.01); *A61K 31/4196* (2013.01); *A61K 39/39558* (2013.01); *A61K 45/06* (2013.01); *C07K 16/3084* (2013.01); *G01N 33/57407* (2013.01); *G01N 33/57415* (2013.01); *A61K 2039/505* (2013.01); *G01N 2405/10* (2013.01); *G01N 2800/54* (2013.01); *G01N 2800/7028* (2013.01)

(58) Field of Classification Search
None
See application file for complete search history.

(56) References Cited

U.S. PATENT DOCUMENTS

| | | |
|---|---|---|
| 2003/0040023 A1 | 2/2003 | Klassen et al. |
| 2008/0019968 A1 | 1/2008 | Blixt et al. |
| 2008/0038770 A1 | 2/2008 | Hansford et al. |

FOREIGN PATENT DOCUMENTS

| | | | |
|---|---|---|---|
| WO | WO0240717 | * | 5/2002 |
| WO | WO 02-056835 | | 7/2002 |
| WO | WO 2011-160119 | | 12/2011 |

OTHER PUBLICATIONS

Visvader and Lindeman, Nature Reviews Cancer, 2008, vol. 8, pp. 755-767.*
Katrizky et al (Arkivoc, 2003, vol. xv, pp. 47-64).*
Schumacher-Kuckelhorn et al (Pediatr Blood Cancer 2005, vol. 45, pp. 195-201).*
De Giorgi et al (Cancer Biology & Therapy, 2011, vol. 11, pp. 812-815).*
Agalave et al (Chemistry, An Asian Journal, 2011, vol. 6, pp. 2696-2718).*
Battula et al., "Ganglioside GD2 identifies breast cancer stem cells and promotes tumorigenesis," *The Journal of Clinical Investigation*, 122(6):2066-2078, 2012.
Birklé et al., "Down-regulation of GD3 ganglioside and its O-acetylated derivative by stable transfection with antisense vector against GD3-synthase gene expression in hamster melanoma cells: effects on cellular growth, melanogenesis, and dendricity," *Journal of Neurochemistry*, 74:547-554, 2000.
Cazet et al., "$G_{D3}$ synthase expression enhances proliferation and tumor growth of MDA-MB-231 breast cancer cells through c-met activation," *Mol Cancer Res*, 8:1526-1535, 2010.
Cheung et al., "Ganglioside $G_{D2}$ specific monoclonal antibody 3F8: a phase I study in patients with neuroblastoma and malignant melanoma," *J Clin Oncol.*, 5(9):1430-1440, 1987.
Cheung et al., "Quantitation of GD2 synthase mRNA by real-time reverse transcription-polymerase chain reaction," *Cancer*, 94(11):3042-3048, 2002.
Gu et al., "Silencing of GM3 synthase suppresses lung metastasis of murine breast cancer cells," *Breast Cancer Research*, 10(1):1-12, 2008.
Kwon et al., "Triptolide downregulates human GD3 synthase (hST8Sia I) gene expression in SK-MEL-2 human melanoma cells," *Exp. Mol. Med.*, 42:849-855, 2010.
Lluis et al., "GD3 synthase overexpression sensitizes hepatocarcinoma cells to hypoxia and reduces tumore growth by suppressing the cSrc/NF-κB survival pathway," *PLoS One*, 4(11):e8059, 2009.
Mani et al., "The epithelial-mesenchymal transition generates cells with properties of stem cells," *Cell*, 133:704-715, 2008.

(Continued)

*Primary Examiner* — Karen Canella
(74) *Attorney, Agent, or Firm* — Parker Highlander PLLC

(57) ABSTRACT

Methods for determining the presence of cancer stem cells by detecting GD2 expression. Also provided are methods for reducing proliferation of cancer stem cells by contacting the cells with a GD2 targeting agent, such as an anti-GD2 antibody or a GD3 synthase inhibitor. GD3 synthase inhibitor compounds are also provided.

13 Claims, 31 Drawing Sheets

(56) References Cited

OTHER PUBLICATIONS

Nakatani et al., "Characterization of GD3 ganglioside as a novel biomarker of mouse neural stem cells," *Glycobiology*, 20(1):78-86, 2010.

Navid et al., "Immune therapies for neuroblastoma," *Cancer Biology & Therapy*, 8(10):874-882, 2009.

PCT International Preliminary Report on Patentability issued in International Application No. PCT/US2013/028016, dated Sep. 12, 2014.

PCT International Search Report and Written Report issued in International Application No. PCT/US2013/028016, dated Jun. 13, 2013.

Quintana et al., "Phenotypic heterogeneity among tumorigenic melanoma cells from patients that is reversible and not hierarchically organized," *Cancer Cell*, 18:510-523, 2010.

Ruckhäberle et al., "Gene expression of ceramide kinase, galactosyl ceramide synthase and ganglioside GD3 synthase is associated with prognosis in breast cancer," *J Cancer Res Clin Oncol*, 135:1005-1013, 2009.

Sarkar et al., "GD3 synthase regulates epithelial-mesenchymal transition and metastasis in breast cancer," *Oncogene*, pp. 1-10, 2014.

Yanagisawa, "Stem cell glycolipids," *Neurochem Res*, 36:1623-1635, 2011.

Yang et al., "Triptolide inhibits the growth and metastasis of solid tumors," *Mol Cancer Ther*, 2:65-72, 2003.

* cited by examiner

Tumor initiation in NOD/SCID mice

| Cell type | 10,000 cells/site | 1000 cells/site | 100 cells/site | 10 cells/site | 1 cell/site |
|---|---|---|---|---|---|
| GD2+ | 5/5 | 8/13 | 4/8 | 5/10 | 0/10 |
| GD2- | 5/5 | 3/13 | 2/8 | 1/10 | 0/10 |

| Pat # | Type of breast cancer | % of GD2+ cells | ER status | PR Status | Her2/neu |
|---|---|---|---|---|---|
| 1 | Metastatic Adenocarcinoma | 18%±3% | +(100%) | +(70%) | Negative |
| 2 | High grade malignant neoplasm | 3.5%±0.6% | NA | NA | NA |
| 3 | Lobular carcinoma | 0.5%±0.1% | NA | NA | NA |
| 4 | Invasive ductal carcinoma | 7.5%%±0.6% | +(90%) | +(30%) | Negative |
| 5 | Invasive ductal carcinoma | 2.2%±0.3% | +(85%) | +(60%) | Negative |
| 6 | Invasive ductal and lobular carcinoma | 5.5%±1.1% | +(100%) | +(99%) | Negative |
| 7 | Invasive ductal carcinoma | 16.2%±1.3% | +(80%) | +(80%) | Negative |
| 8 | Invasive lobular carcinoma | 2.4%±0.2% | +(95%) | +(95%) | Negative |
| 9 | Ductal carcinoma In Situ | 1.1%±0.2% | +(100%) | +(95%) | Negative |
| 10 | Invasive lobular carcinoma | 5.2%%±1.5% | +(70%) | Negative | Negative |
| 11 | Metastatic Adenocarcinoma | 35.8%±2.1% | Negative | Negative | Negative |
| 12 | Invasive lobular carcinoma | 2.4%±0.3% | +(100%) | +(100%) | Negative |

*FIG. 2C*

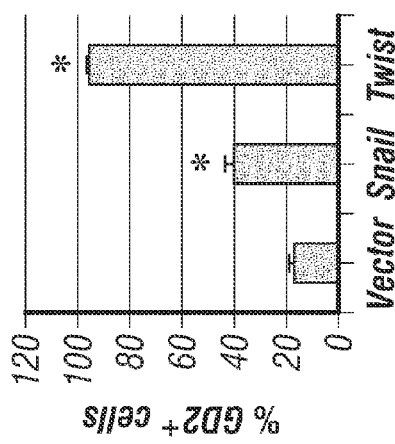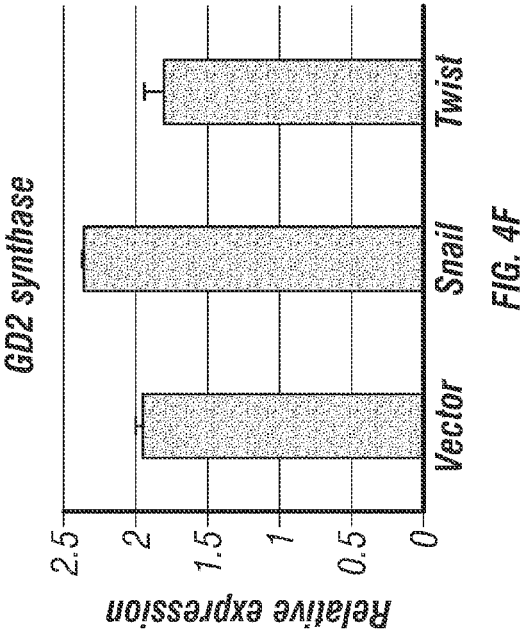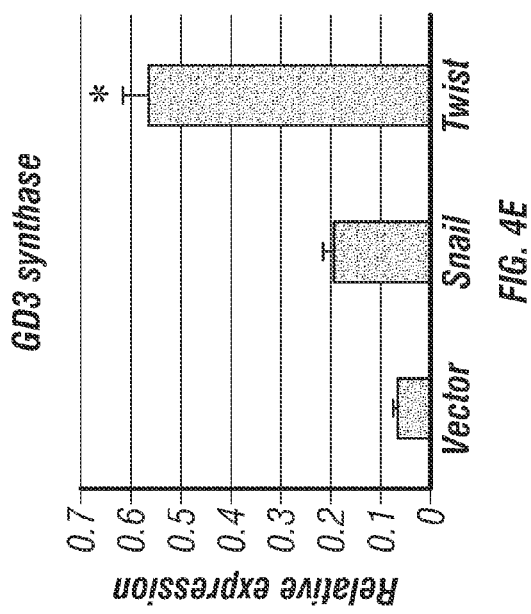

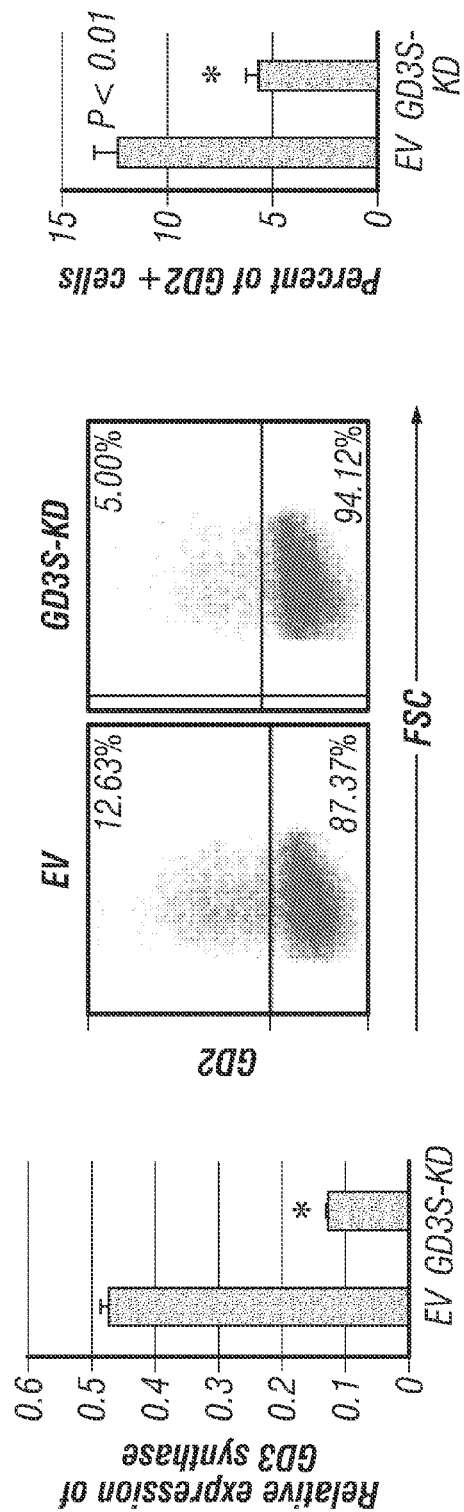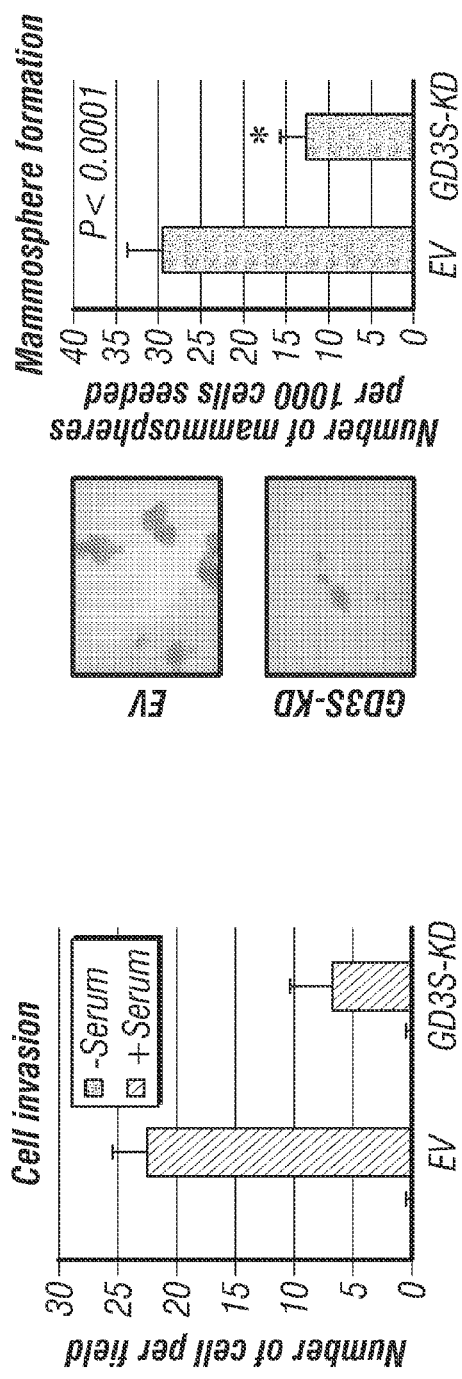
FIG. 5A, FIG. 5B, FIG. 5C, FIG. 5D, FIG. 5E

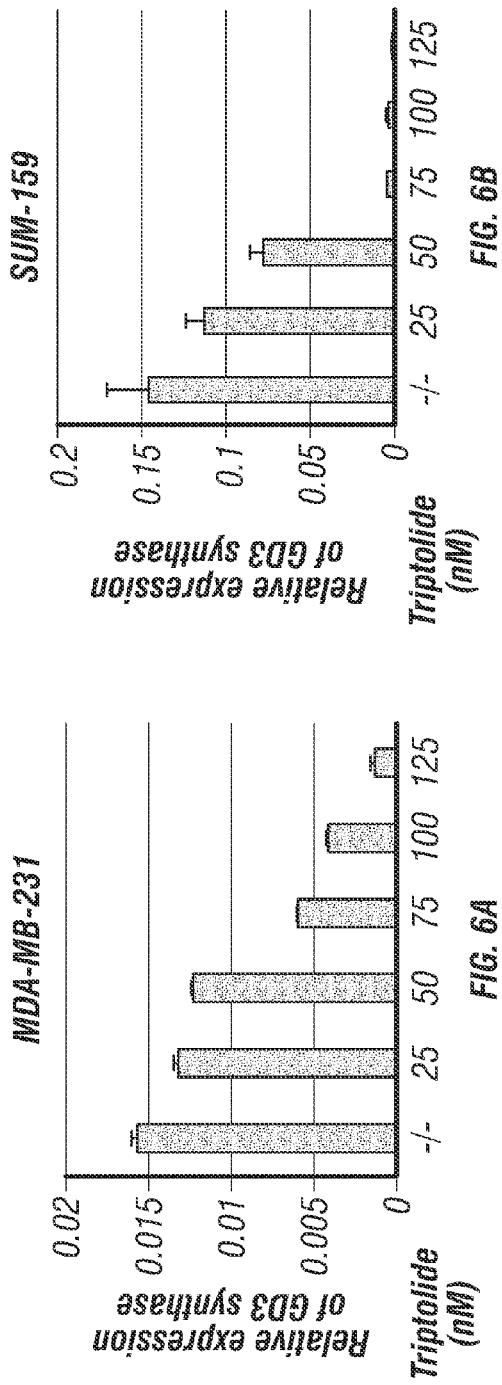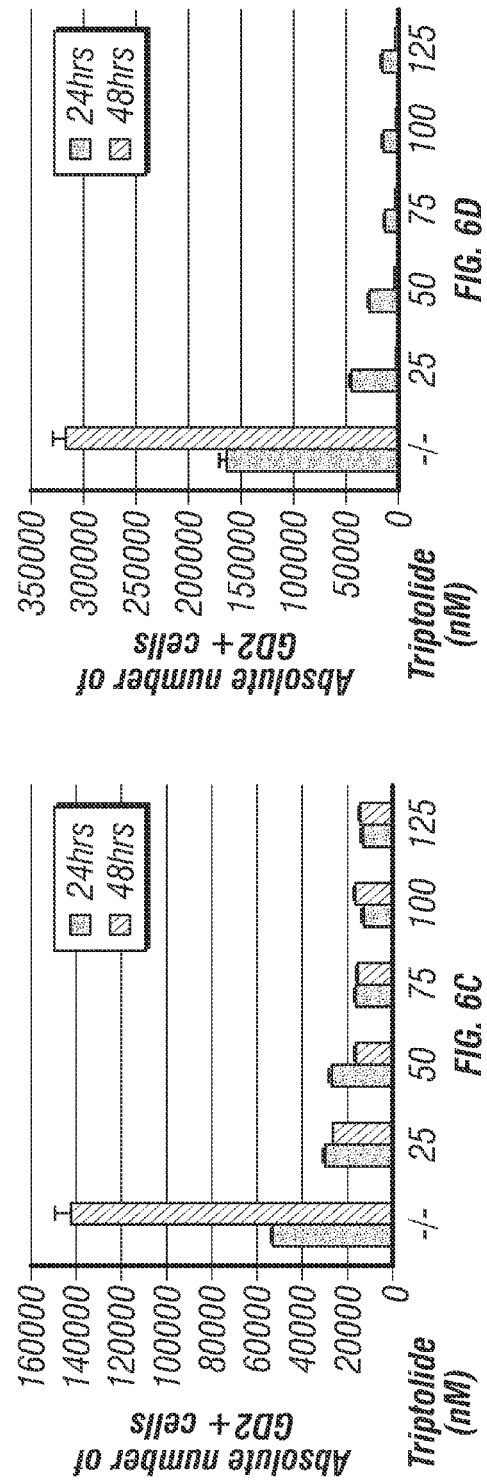

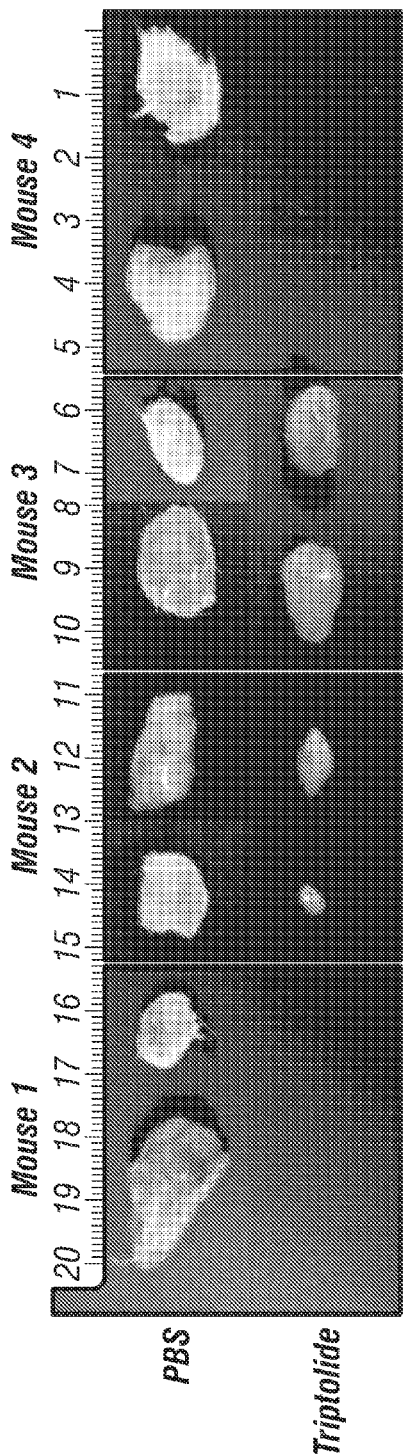
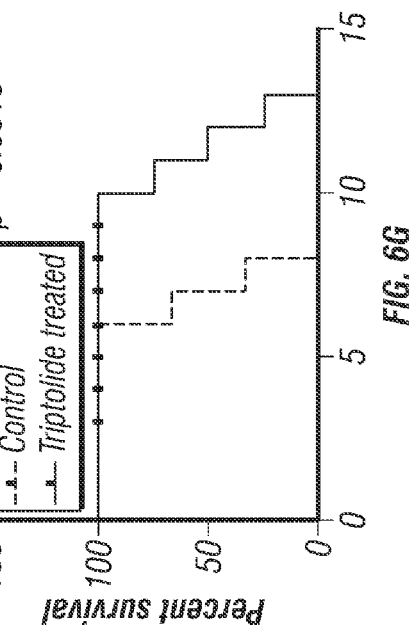
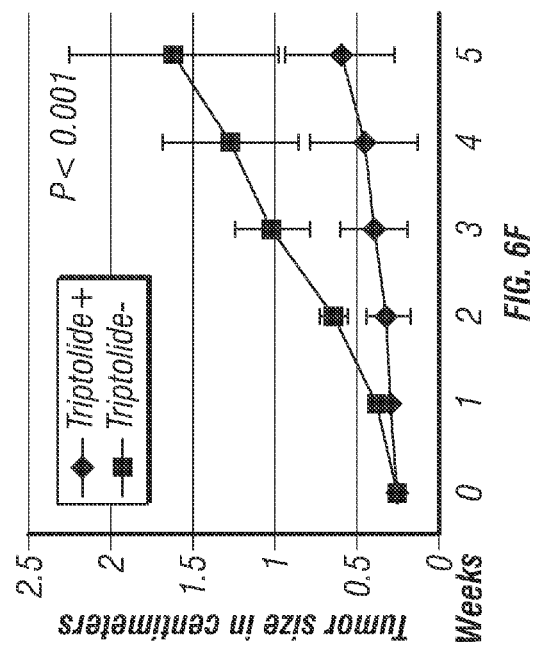
FIG. 6E
FIG. 6G
FIG. 6F

SEQUENCE LISTING

```
<160> NUMBER OF SEQ ID NOS: 1

<210> SEQ ID NO 1
<211> LENGTH: 9737
<212> TYPE: DNA
<213> ORGANISM: Homo sapiens

<400> SEQUENCE: 1
ggggggggtt gcctggcggc gcagcagcgc gggaggcggc gaagggcgca ggagcatcgc      60
tcggagggga caaggggacg ccacgggcca catgtttagg agggagccga gccttctccc     120
ggaccctcgc cgagggcgac cgtgatgctg cagaaccggc gggagcgact cgccgccgcc     180
gctctctgcg cactcggaga ccccagcgcc cgccttctgc aggggaagcg accatggcca     240
tagatcgtga cttcaccccc agccacttcc cctagaaaga aatccttgga aaagttgcat     300
ttgaaaaaat ccttgcgctg acctttgggg ccgacggggc cgaagaagcg tgcgtgcgtt     360
```

-continued

```
tgcaagtaag agaaccaaag gtgtgtgtgc atgggggggct ggcggtgggg gaccctccgc    420
tgccacttcg cctagctttg tgctgaggcc ccggcccccg ccctgggac gccggggctg      480
cgatgagccc ctgcgggcgg gcccggcgac aaacgtccag aggggccatg gctgtactgg    540
cgtggaagtt cccgcggacc cggctgccca tgggagccag tgccctctgt gtcgtggtcc    600
tctgttggct ctacatcttc cccgtctacc ggctgcccaa cgagaaagag atcgtgcagg    660
gggtgctgca cagggcacg gcgtggagga ggaaccagac cgcggccaga gcgttcagga     720
aacaaatgga agactgctgc gaccctgccc atctctttgc tatgactaaa atgaattccc    780
ctatggggaa gagcatgtgg tatgacgggg agttttttata ctcattcacc attgacaatt   840
caacttactc tctcttccca caggcaaccc cattccagct gccattgaag aaatgcgcgg    900
tggtgggaaa tggtgggatt ctgaagaaga gtggctgtgg ccgtcaaata gatgaagcaa    960
attttgtcat gcgatgcaat ctccctcctt tgtcaagtga atacactaag gatgttggat   1020
ccaaaagtca gttagtgaca gctaatccca gcataattcg gcaaaggttt cagaaccttc   1080
tgtggtccag aaagacattt gtggacaaca tgaaaattta taaccacagt tacatctaca  1140
tgcctgcctt ttctatgaag acaggaacag agccatcttt gagggtttat tatacactgt   1200
cagatgttgg tgccaatcaa acagtgctgt ttgccaaccc caacttttctg cgtagcattg  1260
gaaagttctg gaaaagtaga ggaatccatg ccaagcgcct gtccacagga ctttttctgg   1320
tgagcgcagc tctgggtctc tgtgaagagg tggccatcta tggcttctgg cccttctctg   1380
tgaatatgca tgagcagccc atcagccacc actactatga caacgtctta ccctttttctg  1440
gcttccatgc catgcccgag gaatttctcc aactctggta tcttcataaa atcggtgcac   1500
tgagaatgca gctggaccca tgtgaagata cctcactcca gcccacttcc taggaacaat   1560
ggaagaagaa aggactgaac cagggtattt ttgttaggtt ttctatgtga ctccaagagg   1620
gaatggtcaa gttgtttcat gagtttgcat gggcccttgg aaaaacagga aaggagcaat   1680
gaagatccaa gcaaaacttt actttcagcg ttggcttgga ggacaaataa gaaatgaaac   1740
atcctatgaa atactttata gcacatggca gatttgcaac tagtaaaatg ctggtgaaat   1800
gctgttggta aagcacatgg ttcaaatcta gaagatgcag ttcaaaaaca agacagactc   1860
gagttgttag ggctgaggaa ccaatcaagg tagaacaaag aaaatgttgg ggtaaaagtg   1920
ttgctgattg tcaacacaaa ctggcttaat aatattaata agaacctgtc ttattaagac   1980
tggctttaga accgtaggtt ttttttaaaaa attattattt attttttgccc tctttgggga   2040
agtgggtggg tagatttaaa aaatcccttc ctgagtaata aagatacaaa atgttactgc    2100
tgataattgt gatttgttga gccacgtcta tattaactat agctcccctc tattttttaaa   2160
atttttacata agaattgctt cttcctcttt tgtcaagtcc acagagacaa tgtgaagcat   2220
tattgaattt agactgtgtt gcttcatagt ctggataaca ggagccactt tccttcctca   2280
gaatttagga cataaaccca attttaggtc tgcattatgt aagcctgttt gcattgtcat   2340
ttttattttta gtgcaaaaga ctaccaatat gagtgaatta tttgtttgta aattggcata   2400
attgtcttca taatttaatg ttcagaaatg cagtaaagca cgttgatgaa aagcttagtc   2460
tctgtggaag acagaccaga agacaaatcc cttttctatc tactgtggca tattcactgc   2520
aaggtaaagg acatgtatgc atacatgcaa gaatgaattg agcgaaactt tgaatatgtt   2580
tcctcttttg agctattgtt atttagtagt tacctaaaaa agaatacatt tttactagta   2640
taccattaaa aatgtaaaag gcttaacatg tatgcataca tgtagacaca catcacaca   2700
cacaaagtta aacaaagctc attactgtgc aactatgaaa gctgaactca tatgacctgg   2760
```

```
tatggcaaaa atttgtaacc agtgttggag aatcacaaat gtgttatgca ctatccatta    2820
catgttgata taagacaacc gagctcactg gttgccgcac ataatccca tagcagcaca     2880 agatgcaagt cttacccca aatgcttacc cggaatgagc agaattgtct tactcatcct     2940
gattttaccc aaaatctcat gaatgggctt gctgttgagc gtggtcacac aaggtatagt   3000
ttgtacaagt aaagaaatgt gaattagtag ctatttattt ccttagtagc aggtaggact   3060
acttagcttg ttacaacagc tttgatacac agtaagaaaa ctctactgac agattacaag   3120
cagccaaatg tgtttacatt tcagagaagg gtaagggaag cctctcgttg tcttcatact   3180
ttggaatgtc ttaagctaaa atgtgacact agagttcaat ttcttttta ttttaaatgt    3240 cactaaattg taggtaaact gtaccaaaaa gttctagttt aattttaaca gtaaaaactc   3300
agcataccat gttaccacgt aaacaataat ggctggtatt ttctgtgggt taatttaaca   3360
tgacataaac ataggaaagc ccttggcaaa attctacatc attgaagtag accatttcta   3420
aatgcaatta aatagtgagg ttattataaa aattagaatt taaaatatga cttgttgata   3480
gtgcagatta taatgttact tagaaagtta agaattcgag agtaatgatg ctattggaga   3540
actggtttgc tatacggcag caaaaacata atgagaatgt accatgaaga aattgtgtta   3600
aatattcact ttgagtgaaa cttttaaatat gtttcctctt ttgagctact gttatttagc   3660
agttacctaa aaaagaatac attttttacta gtctaccatt aaaaatataa aaggcttaac   3720
aaaaacgcat ataaaagtta ataaaatgtt actcagatta gtactttaat tgttaaaatg   3780
taattaatga gctccataga gcccatacat cacagttcca ttgaaaatat catctggact   3840
agaatctctt aaacccagga agtggaggtt gcagtgagcc aagatggtgc cactgcactc   3900
cagcctgggt gacagggcaa gaccctgtct caaaaaaaaa aaaagaaaa gaaaagaaaa   3960 gaaaatatta tgtggaaatt tttcatcttt ttatgatgcc tgggatagat ttatgcagta   4020
gatttatata taatgtttag tttacaaact tgtgaaacta tttcatgtgg gttctgaaag   4080
gcaaaacaga aatggccagt gctggtgatg tttgattaga ccagctcttc tcagctgggg   4140
tgattcatta tccctctctg gtgacatttg gcaatgtctg gagaccagag acattttta   4200 ttttcatgac tcaagggtgc taatagcatg tacttagtag aggttaggga tcctgctaaa   4260
gatcttacaa tgcacaagtc agcctctcac agcaaaataa ttatccaggc tgagatgtca   4320
gtagtatcaa ggttgacatc tcagacctgg attagacctg gattagacca aaatgaaatt   4380
ttgattgttc caccttgtct tcacttaaag atagatatac atgctcacag cattcaaaat   4440
atgactacaa tttaatgaaa atattttctt atggtagatt acaactcact agatacacca   4500
tacatatgcc ttttggacat aattggttag ataggagtgt gtgtgtgtgt gtgtgtgtgt   4560
gtgtgtgtgt gtgtgtgtgt gtagcatgaa gttaggcatc tctatcctta actgtgctat   4620
gtgttcctaa gtaaggacct cgctagaatc atcctgtaga gtgctctgga atactctatt   4680
attaagatct tcaattctaa gctcccatta tctttctttg tttatctgaa attaagacct   4740
tcagaattag gcctggtact tttccagatt tgatcagtta cattttgata taactgactc   4800
ttaaaattca gcttagaaga cattcaataa gaaaatcttt aatcacttt ggtgatgcac    4860 ctgccaagag ggggcatcac tttgtaccat cagactaatt aaaaaaattg ttgtgtagtc   4920
ataaaaatta ggctgatcca taggggcaaa aggaagggtg aagagactaa aaactagtac   4980
cctgatagaa ttttagtttt tattagcctc gatttgagaa ctgcattgat tccaaagatc   5040
atgaaggtag gtgaaggatt aagtcattcc ataattaaga aaagtaatgt ttatatgaaa   5100
```

```
gattttata  tggacaatga  ctcacagaca  catatgcttt  gtatagagga  ttttgccaaa    5160
agtttataca  aaattgcaca  tctaaactgc  ataattctca  tacaagaagt  taaggaagtg    5220
ctcactggat  tttgcttctg  tatagttcac  ttttatctgt  cttcacaagg  gtaggaagta    5280
aatgatctca  aatggcacat  gttcagacaa  tactgtgttt  ggctttgtga  tgtctcatgt    5340 cttctcttg   gctaaaaaaa  attgtttagg  ctatatataa  cttgtacctg  aagcaatctg    5400
gacaacatgg  cttaaaatgg  aaataactg   aaaaaatcct  gggattttaa  atttgccaaa    5460 aataccttg   gattagtcaa  aggctttaca  agagtgttat  agatgatcca  aatggaaac    5520 aatattgata  acatttcttt  tcgtcagcag  ctacatattc  cagttttata  actttattat    5580 atacatttt   tgattattaa  tagaaagtca  gccatccaga  gttttaactt  ctgtggttga    5640
aatattgact  ttgtgaaatt  tttcactgac  aaatacttgt  taggagggac  taaggggga    5700 ggggaatgtt  accagtccac  tgaaaacttt  aggaaatgtt  cattgtgttg  tgtaaatact    5760
ttcccaccag  caccaggtaa  tatattctct  atgtttgtag  aattccaaag  atcaaaagct    5820
gtaaggacgt  ttatgtgaac  ttgacgcaaa  cttgtggagg  aataaggact  gagagtaatg    5880
ttgtgctttt  tctttatctt  cccgtcgtat  aggtcgactc  tcaggttata  tgacttttat    5940
tgggcacacg  tcaggggtgg  aagtggtaga  agtgggttaa  caatttcaag  gcctggcaac    6000
ctaggtcaaa  acctctaata  aagtcagcag  taaacataac  tagcaacttc  attccactat    6060
gtgctaggag  gagggtgagg  caagttgaaa  ggagatgacc  ctatccccac  actctcagga    6120
tgtaaaaggg  cagagtgctc  tctacccta   accttggctt  tttagcaccg  tcagtctctg    6180
tcctctccca  ggagagctgc  cttggctcca  gagttgagct  agtagcattg  tgactagaga    6240
ggtagtgtgg  aaattcgctg  aggacctcaa  aattttacac  tgccttaaac  tgttttgttt    6300
ttgcttaaac  tcgtgctgtc  taaatgtggg  tgttttgtgg  cagagtctga  tcaccccgac    6360
ctagttatag  ccctgccagt  gattctaaag  tggaactttt  ccccctcatt  catatggata    6420
gtctgagtcc  ttgaagctag  ggagatatca  aatattctac  cagttcctac  atagcttctt    6480
taaaagtcct  agagactaac  tcacaggaag  tctgaagccc  agagcgtctg  tttataaact    6540
cctaaatatg  aggccacaat  atttaggttg  agcactagaa  aatttctatt  ttgcaagtgg    6600
aaggagactt  gaatctataa  ttgctgtagc  ttttttttccc  ttctatcata  agaaatgga    6660 taccatctgc  tttaccctca  gcccagactt  gtcttttgaa  ttttttacat  acatcttagg    6720
ggtgagagat  tgaaacaagt  gcatgaatga  aaagcttatt  gaaacataac  acagcccctg    6780
ctcaccattt  cagtaaggga  aaatacatgt  ttctgttcc   ctctaatttg  ttttctctgg    6840
tgccaacatt  tctgatttct  tctgtctcta  atacataagg  aataaatacc  atattttaaa    6900
ttgacttaca  tgcctgcgag  catttgccag  ataatcaaag  cctatgactc  taactttta    6960 aagcacagaa  gaggaattat  attttatggt  cactcctctg  tgtttctatt  gatctctata    7020
ttgtgctaaa  attctttcag  gtaattttt   tcttgttgaa  gctgtgggat  ataatcaatg    7080
atgccaagct  gtctgagaat  tttatagaat  aatatccaaa  tatattgatc  ctgcctcttt    7140
ctgcttctat  gtaattaaac  tttcttttga  tgtttatttt  taaaatgtat  gcttcacaca    7200
acaccaataa  acatctaaga  gatgtgatat  aatccaaggc  aaagaaaagt  aagaatcagt    7260
taatgtctat  tttatctgca  cagcattacg  aacagaaaat  tgtaataaaa  aaggtttaa    7320 ccaaactgaa  aaaagagag   acaaatctct  ggttttaatt  tgaaagatg   attgggagtg    7380 atctcagaag  agagttcagc  aggaagcaag  gaagaggctg  ttgaccttga  gtgcagcctc    7440
aagaatggaa  ccttttttgaa  atattttaaa  ggaaatatct  tgtcatccag  ctgttatggt    7500
```

```
taataatgaa tagttttctc tgggtgaagc ttatccattg cacacctgat gtgctggccc    7560
ctgcgatttc cccaaatgtt ggaatgttgc ctgcataatt tgtggtaatg ggggactgtg    7620
ttcctgcttt tacctggtta caaaaaacaa aacaaaacaa aacaaaacaa caaacagaaa    7680 aaaaagaga gaaaagatgc tagaggaagc agtgtgacag acagatcatg agatgctgac    7740
ggagagaaca gagtggtacc tgtttaccca cttggaccat gacagtatca aggctccacc    7800
ccttgctgtc ccttcccaag aggtgctctc ctgggagttt gatcacagtg aaacaacact    7860
cccgttttct ttttcctttc tttctttctt tctttttttt tttttttttt tttttgttg     7920 agacagagtt ttttgctctt gttgcccagg ctggagtgca atggcgtgat ctcggctcac    7980
cgcaacctcc gcctcccagg ttcaagcgat tctcgtgcct cagcctctgg agtagctggg    8040
attacaggca tgcgccacca cacccggcta attttgtact tttagtagag atggggtttc    8100
tccatattgg tcaggctggt cccgaactcc tgacctcagg tgatctgccc gcctcagcct    8160
cccaaagtgc tgggattaca ggcataagcc accgagccca gccccacact cctgttttca    8220 tagcccttt ttgtctgtac tttggtacat attccccaaa taagattatt atttacatct     8280
gtcatgatga ggcagtgata gcagcaagtg tcactttgac cctcacccct ggaaagtggg    8340
ctatgcatag ctagagttag aacaggaggt tctaatcctg cttccacaat tacttcagta    8400
acaggctttt gtatccatga ttacttaagc tgacttagat gcatttctta ccctgtattc    8460
tagtgtacac aacacaaaca cacataagcc ctttacctgt ggagaagagg gagatggttg    8520
attcagtggg agtggggagt ggcagagggt gccttaactt tttctggctt gaccccact    8580 tccttatgtg tttccttcat atacctctgt cactttagag atgtaatcat gtctgttcca    8640
agttgtatcg ttattatcaa gaagtcctat aaatgtagca aatgtgacta ttttatagaa    8700
atgcacaata gtttataggc cttggagaag tctgataata gtatgtaaat atccttcatt    8760
gaagtcatag aaccttctag taggaagctc cataggtgat aactgcaaga ggattaatgt    8820
ttgtttctcc agtaaacacc ggaagcaagg aatcaatctg tcactgttta tcattcagtc    8880
ttgagcaccg ttgggtgttg ataggttact atagacactc cccttataat taatatacag    8940
gactcacaat ttaggatgtc tgatggccac tagggtacat catagagaca ctagagagaa    9000
gagaacaaat atagctccat caaaaagcct gcttaatctt taacaagtct gaaatattac    9060
taaaattcca gttaccgtgc agcatagtca gtctaaaaag cactggggaa aaaggtgtct    9120
ttttggtctc tttaattcta ttatggcaca ttttaatatt attccacatg tgtgcaaact    9180
atttctcaag agcaaagttt gaggctggag ttaagaaaat agaaaaatta aaacattatt    9240
ttttctcata taatataatc tgactactag ttcatggata taataattct gggaaaaatt    9300
ttagattaaa ctataaaatt gaaatcacct ttgaagagta tatggaattg cttcttttcta   9360 ttaaagccaa cctacattgg caaaaagtgt ggagaaaatc agtgtgctca attctttttg    9420
tagagtttca tctaaaatgt tgcaggtaaa aagaaaact ttaattggta ctttctacgg     9480
tgtgattaga aaaattagta tctatctctg ttggttctgc tgacttgctt ctttccaccg    9540
aatctaaatg caatgtcata ggaggaggtt tgctgtaaaa acatgtcttt ttctttggtg    9600
tattcattgt aattatggct ggcagtgaga aggttcggta agtctcaatt tctctacctc    9660
ctttacttgg agaaaatttg taaatgtacc ctgtgaataa aatgatttt tataaaaaaa      9720 aaaaaaaaaa aaaaaaa                                                   9737
```

GANGLIOSIDE GD2 AS A MARKER AND TARGET ON CANCER STEM CELLS

This application is a national phase application under 35 U.S.C. §371 of International Application No. PCT/US2013/028016, filed Feb. 27, 2013, which claims the benefit of U.S. Provisional Patent Application No. 61/603,789, filed Feb. 27, 2012, each of which are incorporated herein by reference in their entirety.

This invention was made with Government support under grant nos. CA-55164, CA-16672 and CA116199 from the National Institutes of Health. The Government has certain rights in the invention.

INCORPORATION OF SEQUENCE LISTING

The sequence listing that is contained in the file named "UTFC1127WO_ST25.txt", which is 13 KB (as measured in Microsoft Windows®) and was created on Feb. 22, 2013, is filed herewith by electronic submission and is incorporated by reference herein.

BACKGROUND OF THE INVENTION

1. Field of the Invention

The present invention relates generally to the field of molecular biology and oncology. More particularly, it concerns methods for detecting cancer stem cells and methods for therapeutic targeting of such cells.

2. Description of Related Art

In several types of cancer, a distinct subpopulation of cancer cells has a greater capacity to initiate new tumors compared to the bulk of the tumor cells upon transplantation into mice (Rosen and Jordan, 2009; Schatton et al., 2009). These cancer cells have both, long-term self-renewal capacity and the ability to initiate tumors. Since their properties are similar to normal stem cells, these cancer cells have been termed cancer stem cells (CSCs) (Visvader and Lindeman, 2008; Kelly et al., 2007). More recently, CSCs were found to be inherently resistant to conventional cancer therapies and capable of establishing metastases (Fillmore and Kuperwasser, 2008; Bertolini et al., 2009). Accordingly, there is need to identify biomarkers that can be used to detect CSC. Likewise, CSC therapeutic targets need to be identified to provide more effective anti-cancer therapies.

SUMMARY OF THE INVENTION

In a first embodiment there is provided a method for selectively detecting cancer stem cells in a cancer patient comprising testing cells of the cancer to detect the presence of ganglioside GD2 (GD2) positive cells, said cells being candidate cancer stem cells (CSCs). In some aspects, a method comprises selectively detecting cancer stem cells in a cancer patient having a cancer that would be characterized as a GD2 negative cancer, the method comprising testing cells of the GD2 negative cancer to detect the presence of GD2 positive cells therein, said cells being cancer stem cells. In some aspects, the cancer can be an epithelial cancer, such as a breast cancer or melanoma. Thus, in some embodiments a method is provided for detecting the presence of candidate CSCs in a ganglioside GD2 negative cancer, characterized as a cancer composed of at least 90% GD2 negative cells (e.g., at least 92%, 93%, 94%, 95%, 96%, 97%, 98% or 99% GD2 negative cells), the method comprising a) obtaining a cell population from the GD2 negative cancer and b) testing the population with an anti-GD2 antibody to detect the presence of GD2 positive cells, said GD2 positive cells being candidate CSCs.

In a further embodiment a method is provided for predicting relapse in a cancer patient that has been treated for the cancer, the method comprising detecting GD2 expression in the cancer or a biological sample from the patient, wherein the presence of GD2 expression indicates the patient is more likely to relapse. In further aspects, a method of the embodiments comprises predicting relapse in a cancer patient having a GD2 negative cancer and that has been treated for the cancer, the method comprising detecting GD2 expression in the cancer or a biological sample from the patient, wherein the presence of GD2 expression indicates the patient is more likely to relapse. For example, the cancer patient can be a patient treated for an epithelial cancer, such as a breast cancer or melanoma. In still further embodiments a method of predicting relapse in a cancer patient who has been treated for the cancer is provided, the method comprising detecting the presence of candidate CSCs in accordance with the embodiments, wherein the presence of candidate CSCs which are GD2 positive indicates the patient is more likely to relapse.

In some aspects of the embodiments selectively detecting cancer stem cells further comprises detecting CD44 and/or CD24 expression on cells wherein the presence of GD2 expression and the presence of elevated CD44 expression and/or decreased CD24 expression (relative to control levels) indicates the presence of cancer stem cells. In still further aspects, a method of detecting cancer stem cells comprises detecting elevated expression or activity of ganglioside GD3 synthase (GD3S) in cells, said cells being cancer stem cells. Likewise, in some aspects, a method of predicting relapse in a cancer patient further comprises detecting cells that express CD44 and/or CD24 wherein the presence of cell that express GD2, elevated levels of CD44 and/or reduced level of CD24 relative to control levels indicates the patient is more likely to relapse. Thus, a further embodiment there is provided a method for selectively detecting cancer stem cells in a cancer patient comprising testing a sample from the patient to detect the presence of cells that are ganglioside GD2 (GD2) positive, CD44 positive and/or CD24 negative, said cells being candidate cancer stem cells (CSCs). For example, such a method can comprise testing cells from the blood of a patient (e.g., by flow cytometry).

Testing of cells to detect the presence of GD2 positive cells can comprise a range of assays that are well known in the art. For example, testing can comprise performing an ELISA, an immunoassay, a radioimmunoassay (RIA), an immunoradiometric assay, a fluoroimmunoassay, a chemiluminescent assay, a bioluminescent assay, thin layer chromatography (TLC), flow cytometry, positron emission tomography (PET), single photon emission computed tomography (SPECT) imaging or a microscopic assay. Such testing can be in vivo (e.g., as in PET or SPECT) or in vitro (such as by immunoassay (e.g., immunohistochemistry) or TLC). For instance, testing cells to detect the presence of GD2 can comprise contacting cells with a reagent, such as an antibody, that labels cells comprising ganglioside GD2 expression. A reagent can, for example, be labeled by a fluorescent, enzymatic, radioactive or affinity label.

In a further embodiment a method of selectively inhibiting proliferation of cancer stem cells in a patient is provided comprising: (i) identifying a patient with a cancer that would be characterized as a GD2 negative cancer; and (ii) administering a GD2-targeted therapy to the patient in an amount effective to inhibit proliferation of cancer stem cells in the patient. For example, the patient can be a patient with an epithelial cancer, such as a breast cancer or melanoma. In some aspects, the GD2-targeted therapy is administered in an amount effective to kill cancer stem cells in the patient (e.g., by inducing apoptosis in the cells). In certain aspects, a patient for treatment according to the embodiments is a patient that was identified as comprising GD2 expressing cancer stem cells as detailed herein.

In yet a further embodiment there is provided a composition comprising an anti-GD2 antibody for use in detecting the presence of candidate CSCs in a GD2 negative cancer, characterized as a cancer composed of at least 90% GD2 negative cells. In some aspects, a composition further comprises anti-CD44 and/or anti-CD24 antibodies, the anti-GD2 and the anti-CD44 and/or anti-CD24 antibodies for use in detecting the presence of candidate CSCs in a GD2 negative cancer.

In still a further embodiment there is provided a composition comprising a GD2-targeted agent (e.g., a GD2-binding antibody or a GD3S inhibitor) for use in treating a patient having a GD2 negative cancer, characterized as a cancer composed of at least 90% GD2 negative cells, wherein the cancer was determined to comprise GD2 positive candidate CSCs in accordance methods detailed herein.

Certain aspects of the embodiments concern GD2-targeted therapy and administration of such therapy to a patient. For example, the GD2-targeted therapy can be a GD2-binding agent, such as a GD2-binding aptamer or antibody. Examples of GD2-binding antibodies include, but are not limited to, a monoclonal antibody, a Fc portion, Fab, Fab2, ScFv, or a single domain antibody. In some aspects, the GD2-binding agent comprises a toxin, a chemotherapeutic, or a radionuclide. Such a GD2-targeted therapy can be administered locally or systemically relative to the site (or sites) of a cancer. In still further aspects, the GD2-targeted therapy is administered in conjunction with at least a second anti-cancer therapy, such as a chemotherapy, radiotherapy, gene therapy, surgery, hormonal therapy, anti-angiogenic therapy and/or cytokine therapy.

Further examples, of GD2-targeted therapies include GD3 synthase inhibitors. For example, the GD3 synthase inhibitor can be an inhibitor of GD3 synthase expression or an inhibitor of GD3 synthase enzymatic activity. In some aspects, the inhibitor of GD3 synthase expression is a targeted inhibitory RNA (e.g., a siRNA, miRNA or shRNA) or a small molecule (e.g., Triptolide or a Tripolide derivative). In still further aspects, an inhibitor of GD3 synthase enzymatic activity is one of the compounds provided herein (e.g., in Table 5, 8 or 9).

In still a further embodiment there is provided an isolated compound having a structure according to:

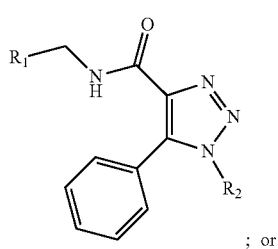

; or

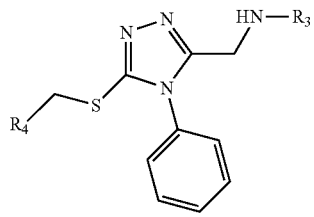

wherein $R_1$ is alkyl, alkenyl, aryl, aralkyl, heteroaryl or one of the groups selected from Table 3; $R_2$ is alkyl, alkenyl, aryl, aralkyl, heteroaryl or one of the groups selected from Table 4; $R_3$ is alkyl, alkenyl, aryl, aralkyl, heteroaryl or one of the groups selected from Table 6; and $R_4$ is alkyl, alkenyl, aryl, aralkyl, heteroaryl or one of the groups selected from Table 7. For example, the compound can be one of those provided in Table 5 or Table 8. In still a further aspect, a compound is provided having a structure provided in Table 9. In some aspects, a composition is provided comprising any of the foregoing compounds and pharmaceutically acceptable carrier.

In still a further embodiment there is provided a method of reducing proliferation in cancer cells comprising contacting the cells with a compound of the embodiments. For example, the cancer cells can be an epithelial cancer cells, such as cells from a breast cancer or melanoma. In still further aspects, the cancer cells are cancer stem cells. In some aspects, the cancer cells are GD2-expressing cell.

Thus, in a further embodiment there is provided a method of treating a patient having a cancer (e.g., a GD-2 expressing cancer) comprising administering an effective amount of a compound of the embodiments to the patient. Similarly, there is provided a composition for use in the treatment of cancer comprising a compound of the embodiments.

In still yet a further embodiment there is provided a method of selectively inhibiting proliferation of cancer stem cells in a patient (e.g., a patient having an epithelial cancer, such as a melanoma or breast cancer) comprising administering an inhibitor of GD3 synthase enzymatic activity to the patient in an amount effective to inhibit proliferation of cancer stem cells in the patient. Accordingly, a composition for use in treating a cancer is provided comprising an inhibitor of GD3 synthase enzymatic activity. In certain aspects, the inhibitor of GD3 synthase enzymatic activity is a small molecule inhibitor, such as one of the compounds provided herein. In some aspects, the inhibitor of GD3 synthase enzymatic activity is administered in an amount effective to kill cancer stem cells in the patient.

In still a further aspect there is provided a method of selectively inhibiting proliferation of cancer stem cells in a patient having cancer comprising: (i) administering a chemotherapy and/or radiation therapy to the patient in an amount effective to inhibit proliferation of cancer cells in the patient; and (ii) administering a GD2-targeted therapy to the patient in an amount effective to inhibit proliferation of cancer stem cells in the patient. For example, the GD2-targeted therapy can be administered before, after or concurrently with a chemotherapy or radiation therapy. In some aspects, the GD2-targeted therapy is administered in an amount effective to kill cancer stem cells in the patient. In some cases, a GD2-targeted therapy, a chemotherapy and/or radiation therapies are administered locally. In some aspects, one or more of the therapies is administered systemically.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6: Triptolide inhibits the expression of GD3 synthase, induce apoptosis in MDA-MB-231 cells, and blocks tumor growth in NOD/SCID mice. MDA-MB-231 cells (A) or SUM159 cells (B) ($5 \times 10^5$/well) of 6 well cell culture dish was treated with 25 nM or 50 nM or 75 nM or 100 nM or 125 nM concentration of Triptolide for 24 hrs. Total RNA was extracted and GD3S expression was measured by real-time RT-PCR. (C) To measure $GD2^+$ cells growth inhibition, $5 \times 10^5$ MDA-MB-231 cells were plated in each well of 6 well cell culture dish and treated with 25 nM or 50 nM or 75 nM or 100 nM or 125 nM concentration of Triptolide for 48 hrs or 72 hrs. After incubation, the cells were detached with trypsin and stained with anti-GD2 antibody and Sytox-Red (for dead cells). The stained cells were analyzed on LSR-II flow cytometer. Absolute number of live cells were calculated by measuring 1000 events for True Count® beads as explained methods. (D) To determine the inhibition of tumor growth, $1 \times 10^6$ MDA-MB-231 cells were subcutaneously transplanted into NOD/SCID mice (n=8, 4 mice/group). A group of the mice were treated with 0.15 mg/kg/day of triptolide and the control group was treated with PBS everyday by intra peritoneal injections. At the end of 8 weeks, mice were sacrificed, tumors were dissected out and photographed. (E) Tumors sizes from the mice in experiment in FIG. 6D were measured every week after tumor engraftment and the measurements were shown in a line graph. (F) The survival analysis was based on Kaplan-Myer estimation and groups were compared by the log-rank test. Control (n=4, black line) and Triptolide (n=4, blue line), were analyzed for cumulative survival. Survival was defined as the time (in weeks) from transplant until death. P value represents the statistical significance.

DESCRIPTION OF ILLUSTRATIVE EMBODIMENTS

I. The Present Invention

Figures 1A, 1B:
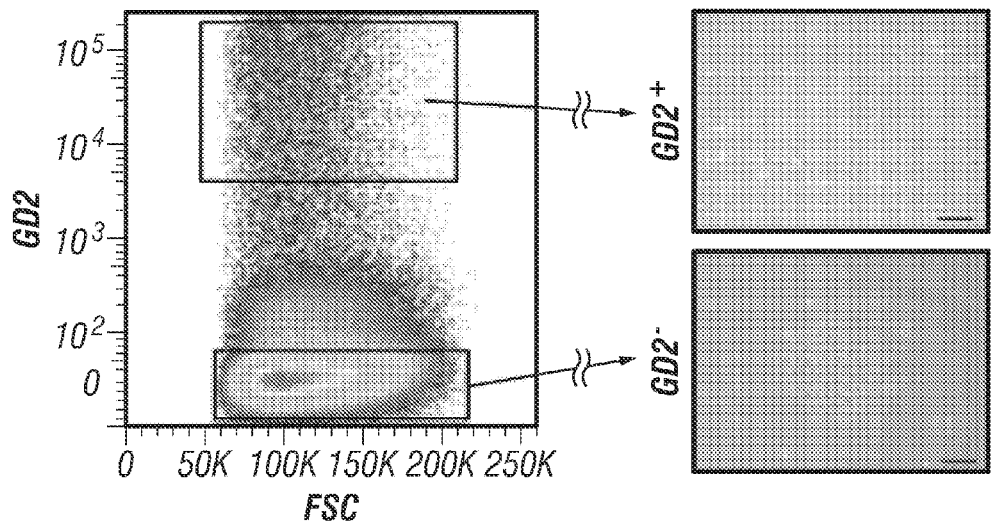
FIG. 1: GD2 identifies CSCs in breast cancer. (A) HMLER cells were stained with anti-GD2 antibody by indirect staining and cells were analyzed on LSR-II flow cytometer. $GD2^{+/-}$ gates were drawn based on IgG2a isotype control. (B) $GD2^{+/-}$ HMLER cells were cell sorted and cultured in cell cultured dish for 4 days. (C) $2\times10^4$ $GD2^{+/-}$ HMLER cells were cultured in 6 well cell culture dishes in triplicates. Total cells were counted on day 2, 4 and 6 using VI-CELLO cell counter. (D) HMLER (left panel) or MDA-MB-231 cells ($1\times10^3$) were sorted into each well of 24-well ultra-low attachment dishes containing mammosphere growth medium using the FACSAria-II cell sorter. Cells were cultured for 12 days, and the photos were taken using a light microscope. (E-F) Bar graph showing the number of mammospheres formed from $GD2^{+/-}$ HMLER (E) or MDA-MB-231 (F) cells. The experiment was performed in triplicates. (G) $GD2^{+/-}$ MDA231 cells were sorted (1 cell or 5 cells/well) into 96-well ultra-low attachment dishes containing mammosphere growth medium. Cells were cultured for 12 days, and mammospheres were counted using a light microscope. (H) Bar graph showing the number of mammospheres formed from single $GD2^{+/-}$ MDA231 cells. (I) Graphic representation of the size of mammospheres measured using a hemocytometer. (J) $GD2^{+/-}$ MDA231 cells were FACS sorted as described previously, and 10,000, 1,000 or 100 or 10 or 1 cells were transplanted subcutaneously into NOD/SCID mice. Tumor formation was observed 4-12 weeks after transplantation.

Cancer stem cells (CSCs) are a small subpopulation of cancer cells that have increased resistance to conventional therapies and are capable of establishing metastasis. Accordingly, these cells often survive conventional cancer therapy and can then reconstitute the cancer leading to relapse. The presence of CSC may, in fact, partly explain why long-term relapse-free remission is so rare even after aggressive anti-cancer therapy. Therefore, there is a pressing need for ways of identifying CSCs and therapeutically targeting these cells. Unfortunately, to date, very few biomarkers of CSCs have been identified.

The studies herein establish that ganglioside GD2 identifies a small fraction of cells in human breast cancer cell lines and patient samples, capable of forming mammospheres and initiating tumors. The majority of GD2+ cells have a CD44$^{high}$/CD24$^{low}$, CSC associated, cell surface phenotype (FIG. 2). Gene expression analysis likewise revealed that GD3 synthase (GD3S) is highly expressed in GD2+ as well as in CD44$^{high}$/CD24$^{low}$ cells (FIG. 3). Thus, GD2 (and GD3S) expression represent markers that can be use to rapidly identify cancer stem cells. Even in cancers that would be characterized as GD2 negative, a small subset of cells that represent CSCs can be identified by the presence of Gd2 and/or increased GD3S expression. Such methods for detecting CSCs can allow the prognostic features of a cancer to be determined, which can guide therapeutic intervention. Moreover, the effectiveness of ongoing anticancer therapy can be guided by detecting CSCs as method of determine a risk of relapse.

Perhaps even more importantly GD2 and precursors or enzymes involved in its synthesis (e.g., GD3S) were identified by the studies herein as effective targets for inhibition of CSCs. For example, the cell surface marker GD2 can be used to directly target CSC with GD2-binding therapeutics, such as antibodies. It has also been demonstrated that interrupting GD2 production reduced growth, or even cause cell death, in CSCs. For example, stable knock-down of GD3S expression using shRNA decreased cell proliferation, impaired in vitro matrigel invasion by more than 10-fold and completely abolished tumor growth in vivo (FIG. 5). Furthermore, Triptolide, an anti-inflammatory and anti-cancer drug, which acts to inhibit GD3S expression in melanoma cells, also inhibited GD3S expression in breast cancer cells by >95% in a dose dependent manner and induced apoptosis in a time dependent manner (FIG. 6). In fact, intra-peritoneal administration of Triptolide in NOD/SCID mice bearing breast-derived tumors eliminated tumors in 50% and reduced the tumor volume 7- to 8-fold in 25% of the mice. These studies demonstrate the effectiveness of GD2-targeting agents, such as GD3S inhibitors, for the treatment of cancer, or more particularly for selective targeting of CSCs.

II. Gangliosides and Ganglioside Synthases

Ganglioside GD2 (as per Svennerholm's nomenclature system (Svennerholm, 1963)) is highly expressed on bone marrow-derived MSCs and therefore, this marker is being used for the prospective isolation of these cells (Martinez et al., 2007). Gangliosides are sialic acid-bearing glycosphingolipids expressed on all vertebrate cells (Posse de Chaves and Sipione, 2009). They are anchored to the plasma membrane through their ceramide lipids with their varied glycans extending into the extracellular space (Sonnino and Prinetti, 2010). Among gangliosides, GM2, GD2, and GD3 are highly expressed in human tumors of neuro-ectodermal origin, such as melanomas, gliomas, and neuroblastomas, whereas they are absent or weakly expressed in normal tissues (Lloyd and Old, 1989; Hakomori, 1996). GD2 is a b-series ganglioside expressed mostly on the cell membrane.

GD2 and GD3 are produced from their precursors GD3 and GM3, respectively, by the enzymes GD2 synthase (GD2S) and GD3 synthase (GD3S), respectively (Fishman and Brady, 1976). For example, human GD3S also known as ST8 alpha-N-acetyl-neuraminide alpha-2,8-sialyltransferase 1 (ST8SIA1) is encoded by the nucleic acid sequence of SEQ ID NO: 1 (see, e.g., NCBI accession no. NM_003034.3, incorporated herein by reference).

III. GD2 and GD3S Binding Agents

Among other things, the present invention provides compositions and methods for detecting cancer stem cells, for treating a cancer or for selectively selling cancer stem cells. Accordingly, certain embodiments of the invention concern agents that bind to GD3S or to GD2 (e.g., for detecting GD2 or targeting GD2-expressing cells). In certain aspects a GD3S- or GD2-binding agent is a polypeptide (e.g., an anticalin or a lectin), antibody or a nucleic acid (e.g., an aptamer). Certain non-limiting and exemplary binding molecules are discussed in detail below.

A. Immunological Reagents

In particular embodiments of the invention, immunological reagents are employed. For example, antibodies may be utilized to bind GD2, for detecting GD2expression or to target GD2-expressing cells. Likewise, GD3S-binding antibodies can be used to detect GD3S expression in a sample or a cell. Thus, in some embodiments, antibodies to GD2 or GD3S are employed in diagnostic aspects of the embodiments, such as for detecting the presence of GD2 in a sample, or on or in a cell.

1. Antibodies

In certain aspects of the invention, one or more antibodies may be obtained or produced which have specificity for GD2 or GD3S. These antibodies may be used in various diagnostic or therapeutic applications described herein. A number of antibodies with specificity to GD2 or GD3S are commercially available. For example, the anti-GD2 antibodies for use according to the instant invention include, but are not limited to, HB 8568 (see, e.g., U.S. Pat. No. 4,675,287) and 14G2a.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')2, single domain antibodies (DABs), Fv, scFv (single chain Fv), and polypeptides with antibody CDRs, scaffolding domains that display the CDRs (e.g., anticalins) or a nanobody. For example, the antibody can be a VHH (i.e., an antigen-specific VHH) antibody that comprises only a heavy chain. For example, such antibody molecules can be derived from a llama or other camelid antibody (e.g., a camelid IgG2 or IgG3, or a CDR-displaying frame from such camelid Ig) or from a shark antibody. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with the present invention. Minibodies are sFv polypeptide chains which include oligomerization domains at their C-termini, separated from the sFv by a hinge region, Pack et al. (1992). The oligomerization domain comprises self-associating α-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992); Cumber et al. (1992).

Antibody-like binding peptidomimetics are also contemplated in the present invention (Liu et al., 2003) describe "antibody like binding peptidomimetics" (ABiPs), which are peptides that act as pared-down antibodies and have certain advantages of longer serum half-life as well as less cumbersome synthesis methods. Likewise, in some aspects, antibody-like molecules are cyclic or bicyclic peptides. For example, methods for isolating antigen-binding bicyclic peptides (e.g., by phage display) and for using the such peptides are provided in U.S. Patent Publn. No. 20100317547, incorporated herein by reference.

Monoclonal antibodies (MAbs) are recognized to have certain advantages, e.g., reproducibility and large-scale production. Embodiments of the invention provide monoclonal antibodies of the human, murine, monkey, rat, hamster, rabbit and chicken origin. Due to the ease of preparation and ready availability of reagents, murine monoclonal antibodies will often be preferred.

"Humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

2. Antibody Conjugates

The present invention provides antibodies against GD2 and/or GD3S proteins, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins (e.g., TNF alpha or gelanin), anti-tumor agents, therapeutic enzymes, radio-labeled nucleotides, antiviral agents, chelating agents, cytokines, growth factors, and oligo- or poly-nucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin. For example, an antibody can be conjugated to a maytansinoid (e.g., maytansinol or the DM1 maytansinoid, see, U.S. Pat. Nos. 5,208,020; 6,333,410; and 7,276,497), auriculin, calicheamicin, duocarmicin or tubulysin.

Certain examples of antibody conjugates are those conjugates in which the antibody is linked to a detectable label (e.g., for use in antibody diagnostics). "Detectable labels" are compounds and/or elements that can be detected due to their specific functional properties, and/or chemical characteristics, the use of which allows the antibody to which they are attached to be detected, and/or further quantified if desired.

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might use astatine211, 14carbon, 51chromium, 36chlorine, 57cobalt, 58cobalt, copper67, 152Eu, gallium67, 3hydrogen, iodine123, iodine125, iodine131, indium111, 59iron, 32phosphorus, radium223, rhenium186, rhenium188, 75selenium, 35sulphur, technicium99m, thorium227 and/or yttrium90. 125I is often used in certain embodiments, and technicium99m and/or indium111 are also often used due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

Antibody conjugates contemplated in the present invention include those intended primarily for use in vitro, where the antibody is linked to a secondary binding ligand and/or to an enzyme (an enzyme tag) that will generate a colored product upon contact with a chromogenic substrate. Examples of suitable enzymes include, but are not limited to, urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817, 837; 3,850,752; 3,939,350; 3,996,345; 4,277,437; 4,275,149 and 4,366,241; each incorporated herein by reference.

IV. GD3 Synthase Inhibitors

As discussed above, the embodiments of the invention contemplate the use of one or more inhibitors of GD3S. As used herein an inhibitor includes enzymatic inhibitors (i.e., that reduce GD3S enzymatic activity), as well as inhibitors of GD3S expression. For example, the inhibitor can be a small molecule inhibitor of GD3S expression such as Triptolide or a derivative thereof (see, e.g., PCT Pat. Publn. WO02/056835, incorporated herein by reference). Likewise, the GD3S inhibitor can be a nucleic acid molecule for reducing expression GD3S. Examples of an inhibitory nucleic acid include, but are not limited to, molecules targeted to a GD3S nucleic acid sequence, such as an siRNA (small interfering RNA), short hairpin RNA (shRNA), double-stranded RNA, an antisense oligonucleotide, a ribozyme and molecules targeted to a GD3S polypeptide such as an aptamer.

A. GD3S Nucleic Acid Targeted Molecules

An inhibitory nucleic acid may inhibit the transcription of a gene or prevent the translation of a GD3S gene transcript in a cell. An inhibitory nucleic acid may be from 16 to 1000 nucleotides long, and in certain embodiments from 18 to 100 nucleotides long (e.g., at least 19, 20, 21, 22, 23, 24, 25, 30, 35, 40, 50 or more nucleotides). In certain embodiments, the inhibitory nucleic acid is an isolated nucleic acid that binds or hybridizes to a GD3S nucleotide sequence such as the GD3S coding sequence of SEQ ID NO:1.

Inhibitory nucleic acids are well known in the art. For example, siRNA, shRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

Since the discovery of RNAi by Fire and colleagues in 1998, the biochemical mechanisms have been rapidly characterized. Double stranded RNA (dsRNA) is cleaved by Dicer, which is an RNAase III family ribonuclease. This process yields siRNAs of ~21 nucleotides in length. These siRNAs are incorporated into a multiprotein RNA-induced silencing complex (RISC) that is guided to target mRNA. RISC cleaves the target mRNA in the middle of the complementary region. In mammalian cells, the related microRNAs (miRNAs) are found that are short RNA fragments (~22 nucleotides). MiRNAs are generated after Dicer-mediated cleavage of longer (~70 nucleotide) precursors with imperfect hairpin RNA structures. The miRNA is incorporated into a miRNA-protein complex (miRNP), which leads to translational repression of target mRNA.

In designing RNAi there are several factors that need to be considered such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Particularly the siRNA exhibits greater than 80, 85, 90, 95, 98% or even 100% identity between the sequence of the siRNA and a portion of a GD3S nucleotide sequence. Sequences less than about 80% identical to the target gene are substantially less effective. Thus, the greater identity between the siRNA and the GD3S gene to be inhibited, the less likely expression of unrelated genes will be affected.

In addition, the size of the siRNA is an important consideration. In some embodiments, the present invention relates to siRNA molecules that include at least about 19-25 nucleotides, and are able to modulate GD3S gene expression. In the context of the present invention, the siRNA is particularly less than 500, 200, 100, 50, 25, 24, 23 or 22 nucleotides in length. In some embodiments, the siRNA is from about 25 nucleotides to about 35 nucleotides or from about 19 nucleotides to about 25 nucleotides in length.

To improve the effectiveness of siRNA-mediated gene silencing, guidelines for selection of target sites on mRNA have been developed for optimal design of siRNA (Soutschek et al., 2004; Wadhwa et al., 2004). These strategies may allow for rational approaches for selecting siRNA sequences to achieve maximal gene knockdown. To facilitate the entry of siRNA into cells and tissues, a variety of vectors including plasmids and viral vectors such as adenovirus, lentivirus, and retrovirus have been used (Wadhwa et al., 2004).

Within an inhibitory nucleic acid, the components of a nucleic acid need not be of the same type or homogenous throughout (e.g., an inhibitory nucleic acid may comprise a nucleotide and a nucleic acid or nucleotide analog). Typically, an inhibitory nucleic acid form a double-stranded structure; the double-stranded structure may result from two separate nucleic acids that are partially or completely complementary. In certain embodiments of the present invention, the inhibitory nucleic acid may comprise only a single nucleic acid (polynucleotide) or nucleic acid analog and form a double-stranded structure by complementing with itself (e.g., forming a hairpin loop). The double-stranded structure of the inhibitory nucleic acid may comprise 16-500 or more contiguous nucleobases, including all ranges there between. The inhibitory nucleic acid may comprise 17 to 35 contiguous nucleobases, more particularly 18 to 30 contiguous nucleobases, more particularly 19 to 25 nucleobases, more particularly 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

siRNA can be obtained from commercial sources, natural sources, or can be synthesized using any of a number of techniques well-known to those of ordinary skill in the art. For example, commercial sources of predesigned siRNA include Invitrogen's Stealth™ Select technology (Carlsbad, Calif.), Ambion® (Austin, Tex.), and Qiagen® (Valencia, Calif.). An inhibitory nucleic acid that can be applied in the compositions and methods of the present invention may be any nucleic acid sequence that has been found by any source to be a validated downregulator of a GD3S.

In some embodiments, the invention features an isolated siRNA molecule of at least 19 nucleotides, having at least one strand that is substantially complementary to at least ten but no more than thirty consecutive nucleotides of a nucleic acid that encodes GD3S, and that reduces the expression of GD3S. In one embodiments of the present invention, the siRNA molecule has at least one strand that is substantially complementary to at least ten but no more than thirty consecutive nucleotides of the mRNA that encodes GD3S.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Publication 2004/0019001 and U.S. Pat. No. 6,673,611 (each of which is incorporated by reference in its entirety). Collectively, all such altered nucleic acids or RNAs described above are referred to as modified siRNAs.

In one embodiment, RNAi is capable of decreasing the expression of GD3S by at least 10%, at least 20%, at least 30%, or at least 40%, at least 50%, at least 60%, or at least 70%, at least 75%, at least 80%, at least 90%, at least 95% or more or any ranges in between the foregoing.

Certain embodiments of the present invention pertain to methods of inhibiting expression of a gene encoding GD3S in a cell by introduction of inhibitory nucleic acids into the cell. Introduction of siRNA into cells can be achieved by methods known in the art, including for example, microinjection, electroporation, or transfection of a vector comprising a nucleic acid from which the siRNA can be transcribed. Alternatively, a siRNA can be directly introduced into a cell in a form that is capable of binding to target GD3S mRNA transcripts. To increase durability and membrane-permeability the siRNA may be combined or modified with liposomes, poly-L-lysine, lipids, cholesterol, lipofectine or derivatives thereof. In certain aspects cholesterol-conjugated siRNA can be used (see, Song et al., 2003).

B. Small Molecule GD3S Inhibitors

Small molecule inbitors of GD3S include, but are not limited to, inhibitors of GD3S enzymatic activity and inhibitors of GD3S expression. For example, the inhibitor can be Triptolide (see, structure (III)) or a derivative of Triptolide that has been modified to enhance its solubility. In some aspects, the Triptolide derivative is one of the Triptolide prodrugs provided in PCT Pat. Publn. WO02/056835 (incorporated herein by reference).

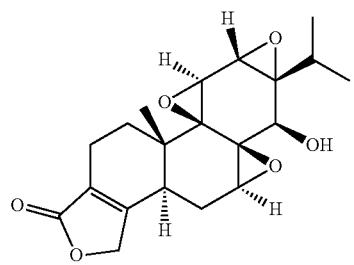

(III)

Molecular modeling was also used to identify candidate GD3S inhibitors. Such inhibitors are contemplated for use in reducing proliferation and/or inducing cell death in cancer cells, in particular in cancer stem cells, such as GD2-expressing cells.

A first set of candidate GD3S inhibitors have a general structure according to:

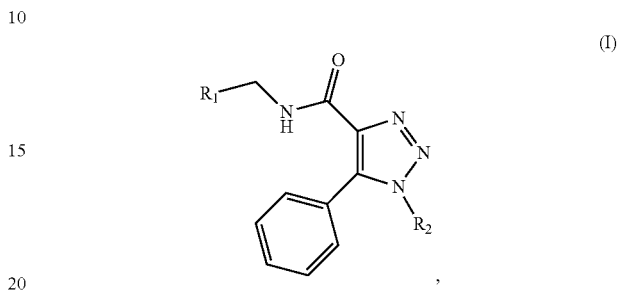

(I)

wherein $R_1$ is alkyl, alkenyl, aryl, aralkyl, heteroaryl or one of the groups selected from Table 3; and $R_2$ is alkyl, alkenyl, aryl, aralkyl, heteroaryl or one of the groups selected from Table 4. Some specific GD3S inhibitor candidates are provided in Tables 5 below.

TABLE 3

Selected $R_1$ groups for compound (I).

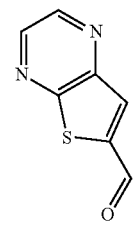

1

857283-69-3

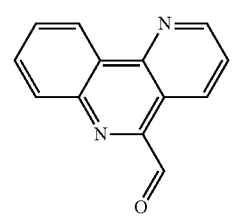 [SMILES: O=Cc1nc2ccccc2c2ncccc12]

2

69164-27-8

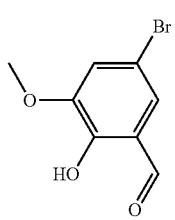

3

5034-74-2

TABLE 3-continued
Selected R₁ groups for compound (I).
4
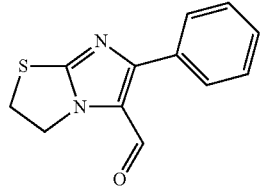 [SMILES: O=Cc1c(-c2ccccc2)nc2n1CCS2]
75224-64-5
5
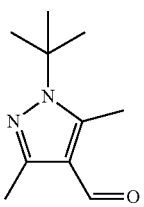
647824-51-9
6
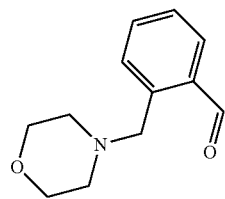 [SMILES: O=Cc1ccccc1CN1CCOCC1]
736991-21-2
7
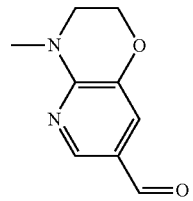
921938-80-9
8
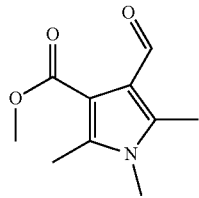
175276-49-0
9
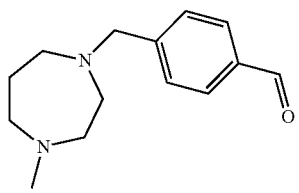 [SMILES: CN1CCCN(Cc2ccc(C=O)cc2)CC1]
884507-48-6
TABLE 4
Selected R₂ groups for compound (I).
1
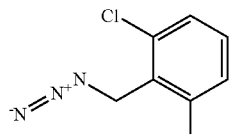
EN400-16143
2
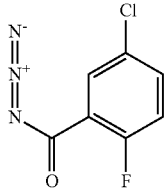 [SMILES: [N-]=[N+]=NC(=O)c1cc(Cl)ccc1F]
EN400-16228
3
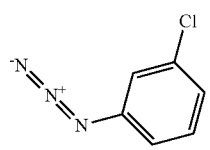
EN400-16264
4
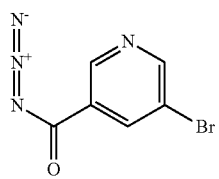
EN400-16219
5
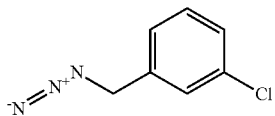
EN400-16135
6
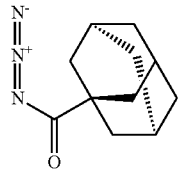 [SMILES: [N-]=[N+]=NC(=O)[C@]12CC3C[C@H](C[C@H](C3)C1)C2]
EN400-15950
7
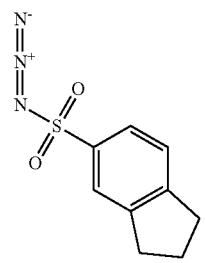 [SMILES: [N-]=[N+]=NS(=O)(=O)c1ccc2c(c1)CCC2]
EN400-16071

TABLE 4-continued
Selected R₂ groups for compound (I).
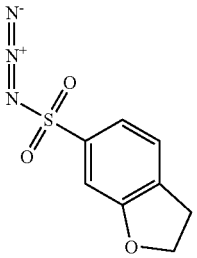 [SMILES: [N-]=[N+]=NS(=O)(=O)c1ccc2c(c1)OCC2]
EN400-16052
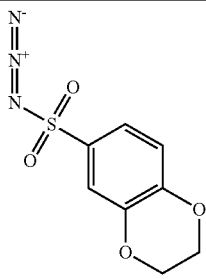
EN400-16111
Thus, in certain specific aspects the GD3S inhibitor is selected from one of those provided in Table 5.
TABLE 5
Selected GD3S inhibitor candidates.
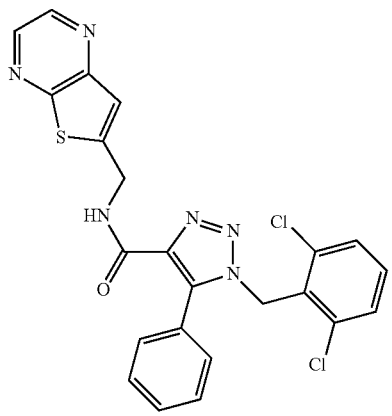 [SMILES: O=C(NCc1cc2nccnc2s1)c1nnn(Cc2c(Cl)cccc2Cl)c1-c1ccccc1]
| | |
|---|---|
| Name: | GD3S2-857283-69-3_EN400-16143 |
| Rank: | 1 |
| Score: | 8.92 |
| MMGBSA DGbind: | −89.25 |
| QPlogS: | −7.12 |
| CSCQRE | 4 |
| Z-Score | 3.15 |
| R1 CASID: | 857283-69-3 |
| R2 CASID: | EN400-16143 |
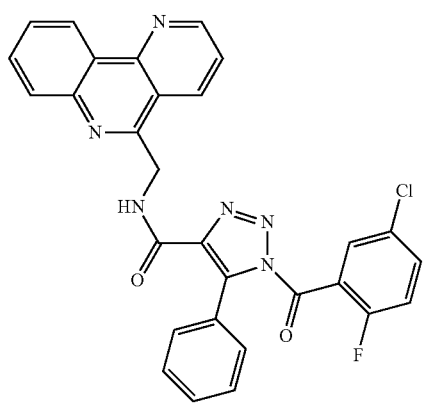 [SMILES: O=C(NCc1nc2ccccc2c2ncccc12)c1nnn(C(=O)c2cc(Cl)ccc2F)c1-c1ccccc1]
| | |
|---|---|
| Name: | GD3S2-69164-27-8_EN400-16228 |
| Rank: | 2 |
| Score: | 9.21 |
| MMGBSA DGbind: | −87.46 |
| QPlogS: | −7.02 |
| CSCQRE | 4 |
| Z-Score | 3.22 |
| R1 CASID: | 69164-27-8 |
| R2 CASID: | EN400-16228 |

TABLE 5-continued

Selected GD3S inhibitor candidates.

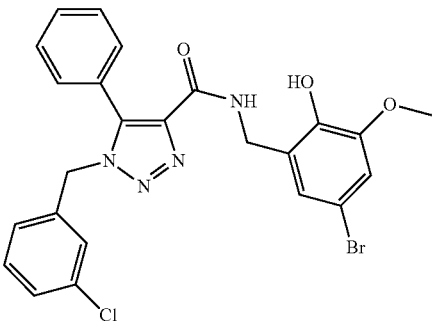 [SMILES: COc1cc(Br)cc(CNC(=O)c2nnn(Cc3cccc(Cl)c3)c2-c2ccccc2)c1O]

| | |
|---|---|
| Name: | GD3S2-5034-74-2_EN400-16246 |
| Rank: | 3 |
| Score: | 9.05 |
| MMGBSA DGbind: | −87.27 |
| QPlogS: | −7.36 |
| CSCQRE | 3 |
| Z-Score | 3.13 |
| R1 CASID: | 5034-74-2 |
| R2 CASID: | EN400-16246 |

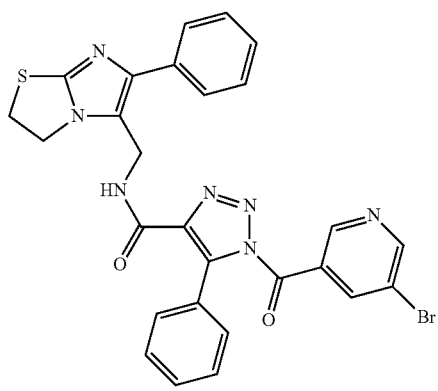 [SMILES: O=C(NCc1c(-c2ccccc2)nc2n1CCS2)c1nnn(C(=O)c2cncc(Br)c2)c1-c1ccccc1]

| | |
|---|---|
| Name: | GD3S2-75224-64-5_EN400-16219 |
| Rank: | 4 |
| Score: | 8.23 |
| MMGBSA DGbind: | −92.13 |
| QPlogS: | −7.22 |
| CSCQRE | 3 |
| Z-Score | 2.94 |
| R1 CASID: | 75224-64-5 |
| R2 CASID: | EN400-16219 |

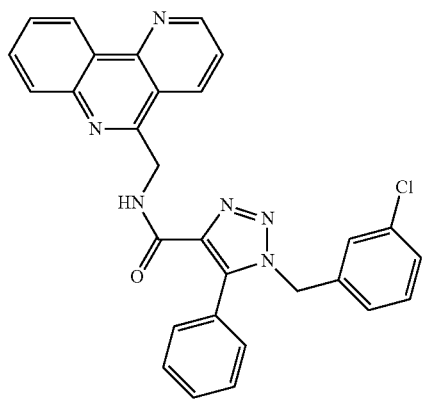 [SMILES: O=C(NCc1nc2ccccc2c2ncccc12)c1nnn(Cc2cccc(Cl)c2)c1-c1ccccc1]

| | |
|---|---|
| Name: | GD3S2-69164-27-8_EN400-16135 |
| Rank: | 5 |
| Score: | 9.46 |
| MMGBSA DGbind: | −82.16 |
| QPlogS: | −7.44 |
| CSCQRE | 4 |
| Z-Score | 3.12 |
| R1 CASID: | 69-164-27-8 |
| R2 CASID: | EN400-16135 |

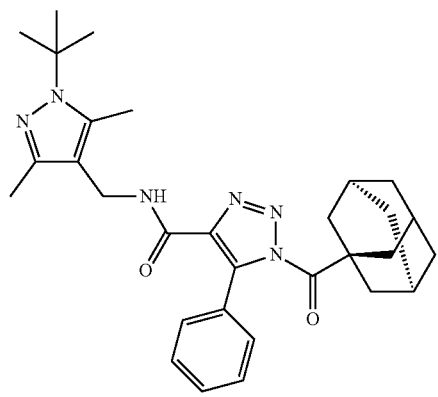 [SMILES: Cc1nn(C(C)(C)C)c(C)c1CNC(=O)c1nnn(C(=O)[C@]23CC4C[C@H](C[C@H](C4)C2)C3)c1-c1ccccc1]

| | |
|---|---|
| Name: | GD3S2-647824-51-9_EN400-15950 |
| Rank: | 6 |
| Score: | 8.60 |
| MMGBSA DGbind: | −88.98 |
| QPlogS: | −7.84 |
| CSCQRE | 2 |
| Z-Score | 2.99 |
| R1 CASID: | 647824-51-9 |
| R2 CASID: | EN400-15950 |

TABLE 5-continued

Selected GD3S inhibitor candidates.

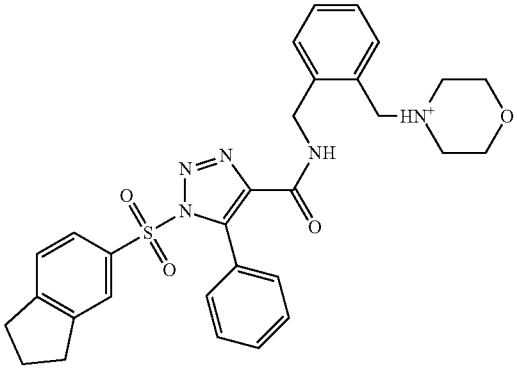 [SMILES: O=C(NCc1ccccc1C[NH+]1CCOCC1)c1nnn(S(=O)(=O)c2ccc3c(c2)CCC3)c1-c1ccccc1]

| | |
|---|---|
| Name: | GD3S2-736991-21-2_EN400-16071 |
| Rank: | 7 |
| Score: | 8.26 |
| MMGBSA DGbind: | −86.95 |
| QPlogS: | −4.13 |
| CSCQRE | 3 |
| Z-Score | 2.74 |
| R1 CASID: | 736991-21-2 |
| R2 CASID: | EN400-16071 |

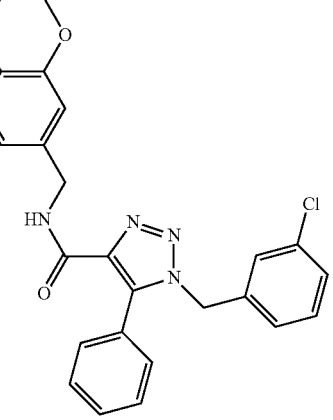

| | |
|---|---|
| Name: | GD3S2-921938-80-9_EN400-16135 |
| Rank: | 8 |
| Score: | 8.54 |
| MMGBSA DGbind: | −87.97 |
| QPlogS: | −8.52 |
| CSCQRE | 2 |
| Z-Score | 2.92 |
| R1 CASID: | 921938-80-9 |
| R2 CASID: | EN400-16135 |

A second set of candidate GD3S inhibitors have a general structure according to:

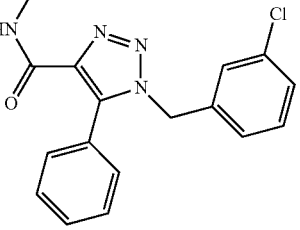
(II)

wherein $R_3$ is alkyl, alkenyl, aryl, aralkyl, heteroaryl or one of the groups selected from Table 6; and $R_4$ is alkyl, alkenyl, aryl, aralkyl, heteroaryl or one of the groups selected from Table 7. Some specific GD3S inhibitor candidates are provided in Tables 8-9 below.

TABLE 6

Selected $R_3$ groups for compound (II).

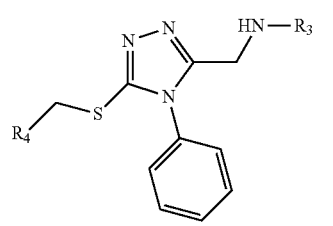

22876-17-1

TABLE 6-continued

Selected $R_3$ groups for compound (II).

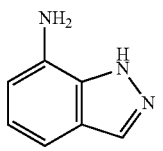

41748-71-4

2

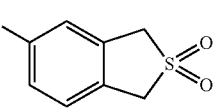

70654-85-2

3

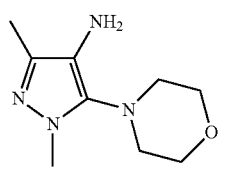

568577-87-7

4

TABLE 6-continued
Selected R₃ groups for compound (II).
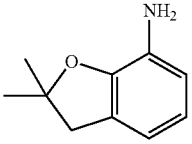
68298-46-4
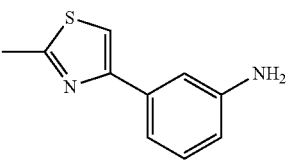
89250-34-0
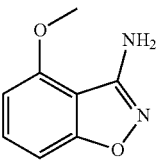
177995-40-3
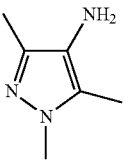
28466-21-9
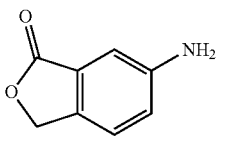 [SMILES: Nc1ccc2c(c1)C(=O)OC2]
57319-65-0
TABLE 7
Selected R₄ groups for compound (II).
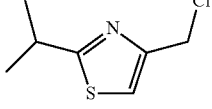
PBMR123293
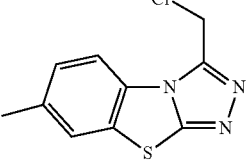
PBMR043509
TABLE 7-continued
Selected R₄ groups for compound (II).
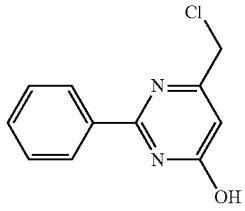 [SMILES: Oc1cc(CCl)nc(-c2ccccc2)n1]
PBMR033476
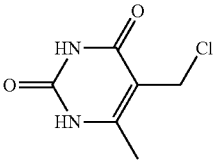
PBMR014533
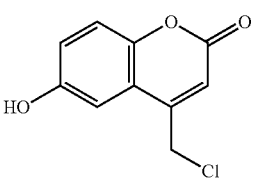 [SMILES: O=c1cc(CCl)c2cc(O)ccc2o1]
PBMR08005
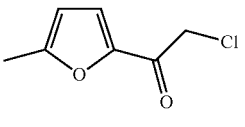
PBMR101394
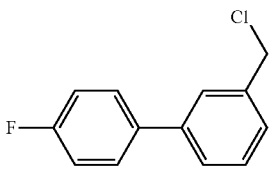
PBMR007592
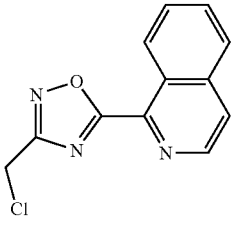 [SMILES: ClCc1noc(-c2nccc3ccccc23)n1]
PBMR007578
PBMR086937

TABLE 8

Selected GD3S inhibitor candidates.

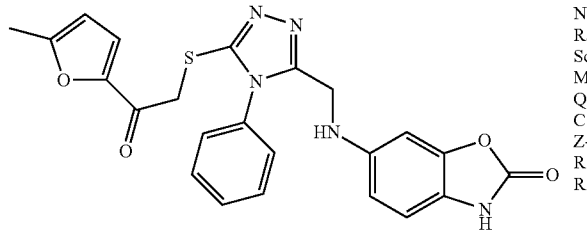

| | |
|---|---|
| Name: | GD3S3-22876-17-1_PBMR123293 |
| Rank: | 1 |
| Score: | 9.82 |
| MMGBSA DGbind: | −80.69 |
| QPlogS: | −4.64 |
| CSCQRE | 2 |
| Z-Score | 3.23 |
| R1 CASID: | 22876-17-1 |
| R2 CASID: | PBMR123293 |

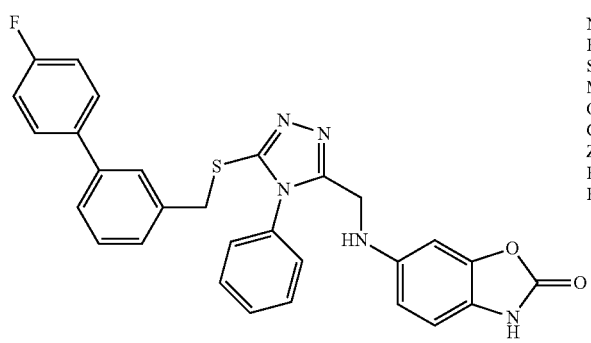

| | |
|---|---|
| Name: | GD3S3-22876-17-1_PBMR043509 |
| Rank: | 2 |
| Score: | 10.00 |
| MMGBSA DGbind: | −82.32 |
| QPlogS: | −5.63 |
| CSCQRE | 4 |
| Z-Score | 3.38 |
| R1 CASID: | 22876-17-1 |
| R2 CASID: | PBMR043509 |

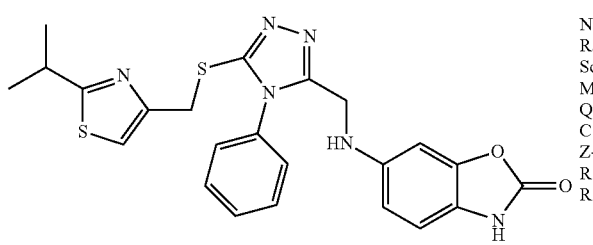

| | |
|---|---|
| Name: | GD3S3-22876-17-1_PBMR033476 |
| Rank: | 3 |
| Score: | 9.87 |
| MMGBSA DGbind: | −80.26 |
| QPlogS: | −7.03 |
| CSCQRE | 3 |
| Z-Score | 3.24 |
| R1 CASID: | 22876-17-1 |
| R2 CASID: | PBMR033476 |

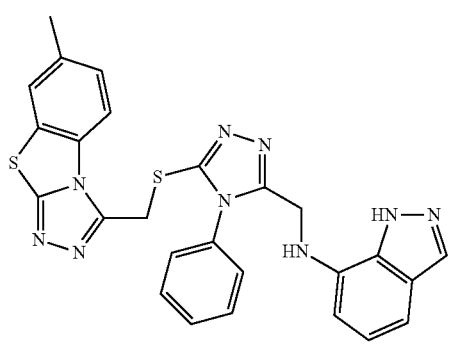 [SMILES: Cc1ccc2c(c1)sc1nnc(CSc3nnc(CNc4cccc5cn[nH]c45)n3-c3ccccc3)n12]

| | |
|---|---|
| Name: | GD3S3-41748-71-4_PBMR014533 |
| Rank: | 4 |
| Score: | 9.97 |
| MMGBSA DGbind: | −82.88 |
| QPlogS: | −8.07 |
| CSCQRE | 3 |
| Z-Score | 3.39 |
| R1 CASID: | 41748-71-4 |
| R2 CASID: | PBMR014533 |

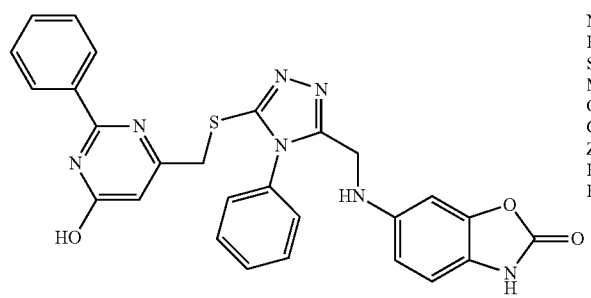

| | |
|---|---|
| Name: | GD3S3-22876-71-1_PBMR080005 |
| Rank: | 5 |
| Score: | 9.80 |
| MMGBSA DGbind: | −80.89 |
| QPlogS: | −6.32 |
| CSCQRE | 2 |
| Z-Score | 3.23 |
| R1 CASID: | 22876-17-1 |
| R2 CASID: | PBMR080005 |

TABLE 8-continued

Selected GD3S inhibitor candidates.

| Structure | Properties |
|---|---|
| (structure) | Name: GD3S3-70654-85-2_PBMR101394<br>Rank: 6<br>Score: 10.00<br>MMGBSA DGbind: −80.19<br>QPlogS: −6.23<br>CSCQRE: 2<br>Z-Score: 3.29<br>R1 CASID: 70654-85-2<br>R2 CASID: PBMR101394 |
| (structure) | Name: GD3S3-568577-87-7_PBMR007592<br>Rank: 7<br>Score: 9.93<br>MMGBSA DGbind: −81.72<br>QPlogS: −5.41<br>CSCQRE: 2<br>Z-Score: 3.33<br>R1 CASID: 658577-87-7<br>R2 CASID: PBMR007592 |
| (structure) | Name: GD3S3-22876-17-1_PBMR007578<br>Rank: 8<br>Score: 9.54<br>MMGBSA DGbind: −81.62<br>QPlogS: −7.44<br>CSCQRE: 3<br>Z-Score: 3.13<br>R1 CASID: 22876-17-1<br>R2 CASID: PBMR007578 |

TABLE 9

Additional selected GD3S inhibitor candidates.

Total_Score: 11.06    1

(structure)

D0000201-F5338-0304

TABLE 9-continued

Additional selected GD3S inhibitor candidates.

Total_Score: 10.67    2

(structure)

D0000194-8017-3681

TABLE 9-continued
Additional selected GD3S inhibitor candidates.
Total_Score: 10.38    3
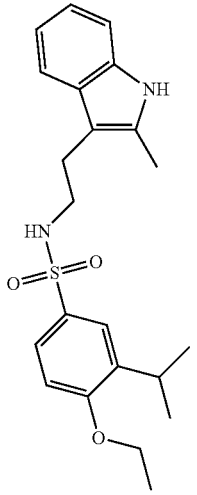 [SMILES: CCOc1ccc(S(=O)(=O)NCCc2c(C)[nH]c3ccccc23)cc1C(C)C]
D0000194-8016-8520
Total_Score: 10.13    4
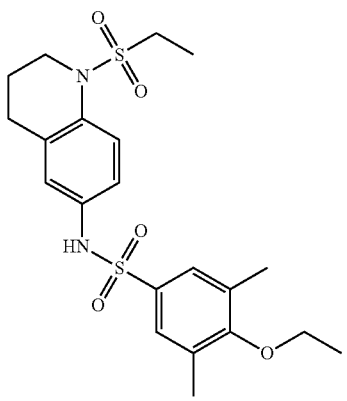 [SMILES: CCOc1c(C)cc(S(=O)(=O)Nc2ccc3c(c2)CCCN3S(=O)(=O)CC)cc1C]
D0000201-F2043-0462
Total_Score: 9.9280    5
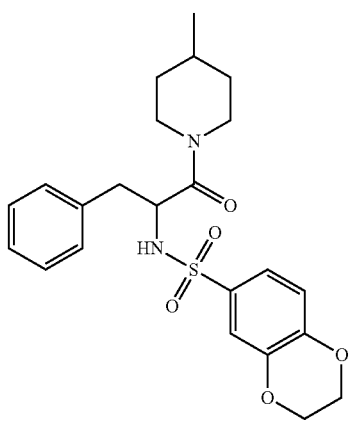 [SMILES: CC1CCN(C(=O)C(Cc2ccccc2)NS(=O)(=O)c2ccc3c(c2)OCCO3)CC1]
D0000199-T5838686
TABLE 9-continued
Additional selected GD3S inhibitor candidates.
Total_Score: 9.9197    6
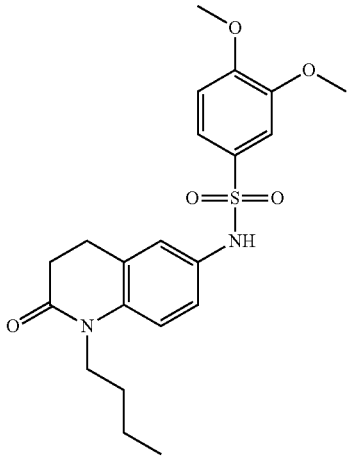 [SMILES: CCCCN1C(=O)CCc2cc(NS(=O)(=O)c3ccc(OC)c(OC)c3)ccc21]
D0000201-F2385-0198
Total Score: 9.7727    7
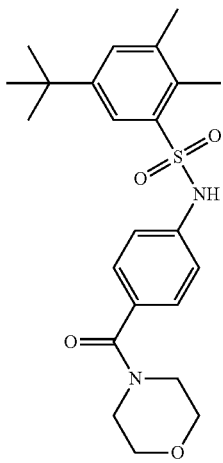 [SMILES: Cc1cc(C(C)(C)C)cc(S(=O)(=O)Nc2ccc(C(=O)N3CCOCC3)cc2)c1C]
D0000200-7116410615
Total Score: 9.7620    8
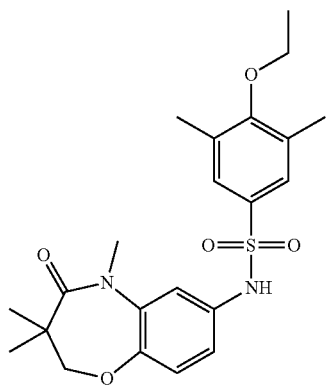
D0000201-F2297-0079

TABLE 9-continued

Additional selected GD3S inhibitor candidates.

Total Score: 9.6359

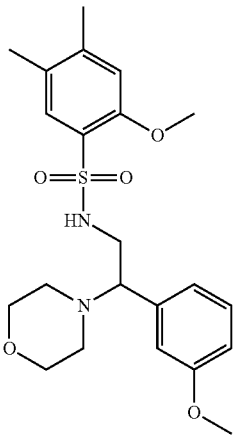

D0000201-F2880-3759

Total_Score: 9.175

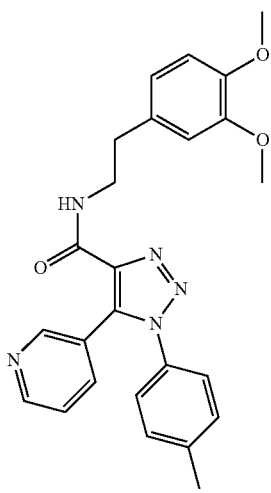 [SMILES: COc1ccc(CCNC(=O)c2nnn(-c3ccc(C)cc3)c2-c2cccnc2)cc1OC]

D0000201-F3398-2599

V. Chemical Group Definitions

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⹀" represents a single bond or a double bond. Thus, for example, the structure

includes the structures

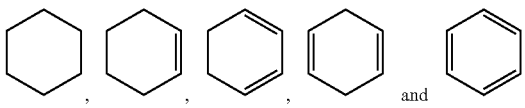

As will be understood by a person of skill in the art, no one such ring atom forms part of more than one double bond. The symbol " ⌇ ", when drawn perpendicularly across a bond indicates a point of attachment of the group. It is noted that the point of attachment is typically only identified in this manner for larger groups in order to assist the reader in rapidly and unambiguously identifying a point of attachment. The symbol "◀" means a single bond where the group attached to the thick end of the wedge is "out of the page." The symbol "⋯⋯‖" means a single bond where the group attached to the thick end of the wedge is "into the page". The symbol " ⌇ " means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

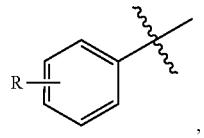

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

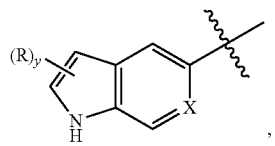

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$," or the class "alkene$_{(C≤8)}$," is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neopentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

, are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CHF, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

, are non-limiting examples of alkenediyl groups. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The groups, —CH═CHF, —CH═CHCl and —CH═CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. When alkynyl is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

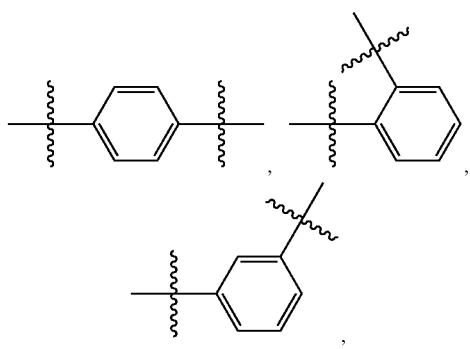

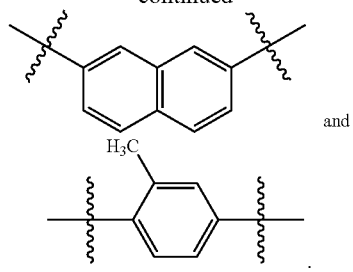

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

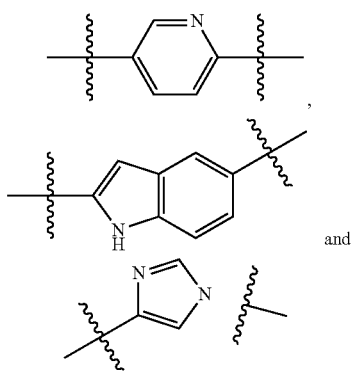

, and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, C(O)CH$_2$CH$_2$CH$_3$, C(O)CH(CH$_3$)$_2$, C(O)CH(CH$_2$)$_2$, C(O)C$_6$H$_5$, C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, A, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Experimental Procedures

Antibodies

The following antibodies were used: Anti-GD2 (clone 14G2a, isotype IgG2a), anti-GD3 (Clone R24, isotype IgG3) as well as isotype control antibodies for IgG2a and IgG3 are from BD (San Jose, Calif., USA). Anti-GD2 antibody (Clone 2Q549) was purchase from abcam (San Francisco, Calif., USA). Anti-GM3 (isotype IgMk) antibody was purchased from Cosmo Bio USA. Inc. (Carlsbad, Calif.). Antibody conjugates anti-CD44 (APC, Allophycocyanin), anti-CD105 (PE, Phycoerythrin), anti-CD106-PE, anti-CD117-PE antibodies are from eBiosciences (San Diego, Calif., USA); Anti-CD166-PE, anti-CD73-PE, anti-CD140b-PE, anti-CD90 (FITC, Fluorescein isothiocyanate) and anti-CD24-FITC antibodies are from BD. Anti-CD271-APC antibody is from Miltenyi Biotec (Auburn, Calif., USA)

Cell Culture

Human mammary epithelial cells (HMECs, also known as HMLE) expressing H-Ras oncogene (—R) were cultured as described (Battula et al., 2010). In brief, HMECs obtained from Clonetics were immortalized with the catalytic subunit of human telomerase and SV40 large T antigen. These cells were transduced with pBabe-puro retroviral vectors expressing Twist, Snail, or empty vector. Human breast cancer cell lines MDA-MB-231, MCF7, MDA-MB-453, SKBR3, BT474, ZR751, MDA-MB-361, B-20, MDA-MB-468, HS578T, Sum159 and Sum149 were cultured according to ATCC recommendations.

Patient Samples

Primary breast tumors were obtained from patients undergoing mammectomy. Following institutional protocols and guidelines, tumors were transferred to the laboratory immediately after surgery, where they were cut into ~2-mm3 pieces. The tumor tissues were washed once with PBS and then incubated with a combination of collagenase-III (Sigma-Aldrich, St. Louis, Mo.) and hyaluronidase (Sigma-Aldrich) for 8-10 hours with constant shaking at 37° C. After incubation, the cells were washed once with PBS containing 10% serum to stop any residual enzyme activity. The resulting cell pellet was re-suspended in PBS and processed on Ficoll density gradient centrifugation to eliminate red blood cells and undigested tissue compartments. The resulting buffy coat was then collected and used for antibody staining.

Flow Cytometry

Single-color staining of HMLE-R cells was performed as described previously (Battula et al., 2009). Briefly, cells were washed twice with phosphate-buffered saline (PBS) containing 1% fetal bovine serum (FBS, FACS buffer), incubated with the indicated primary antibodies for 15 min on ice, washed in FACS buffer, and incubated with the F(ab)2 fragment of goat anti-mouse secondary antibody conjugated with R-phycoerythrin (PE; Dako Cytomations, Glostrup, Denmark) for 15 min. After washing, the cells were analyzed with LSR-II flow cytometer (BD) using FCS-Express (De Novo Software, Los Angeles, Calif.) or FlowJo software (Ashland, Oreg., USA). For double or triple fluorescence staining of HMLE-R and primary breast tumors, cells were first stained with GD2 or GD3 or GM3 or IgG2a or IgG3 or IgM isotype control antibodies (BD) as described above. Next, free binding sites of the secondary antibody were blocked with mouse IgG polyclonal antibody (Southern Biotech, Birmingham, Ala., USA), and cells were diluted 1:20 with PBS or FACS buffer for 25 min on ice, stained with the indicated antibody conjugates, and (after washing) analyzed with an LSR-II flow cytometer. For flow cytometric analysis of cell lines and primary tumor cells, ~1×10$^6$ cells were stained with primary antibodies or antibody conjugates as described above. At least 1×104 events were measured in cell lines and 1×105 cells from primary breast tumors. Sorting of single cells or bulk populations was performed on a FACSAria-II cell sorter (BD).

Immunohistochemistry (IHC)

After deparaffin, the tissue sections (4-μm) were retrieved by being boiled in retrieval buffer (DAKOCytomation Ink. Carpinteria, Calif.) for 20 minutes. After washing the tissue sections were incubated in protein blocking buffer for 15 min (Protein Block Serum-Free, DAKO) at room temperature and then incubated with anti-GD2 antibody (BD, IgG2a, 1:100 dilution, v/v) and anti-Pan Cytokeratin antibody (ab6401, IgG1 abcam, 1:300 dilution, v/v) at 4° C. overnight in a humidified chamber. After washing the sections were incubated with fluorochrome conjugated secondary antibodies (anti-mouse IgG2a conjuagated with Alexafluor 488 and anti-mouse IgG1 conjugated with Alexafluor 594, both from Invitrogen). The nuclei were stained by DAPI. IgG2a k antibody (1:100 dilution, BD Phamingen) was used for isotype control. Following the staining protocol, the sections were photographed using Olympus FV1000 laser confocal microscope (Olympus Imaging America Inc. Center Valley, Pa.).

Viral Transduction

Lentiviral plasmids containing GD3S shRNA (PLKO.1, RHS3979-9603453) or an empty vector were purchased from Open Biosystems (Huntsville, Ala.). Viral supernatants were generated as described before (Rey et al., 2010) using viral packaging system which includes psPAX2 and pM2DG plasmids (kindly provided by Dr. Boyko S. Atanassov). Two days after transfections, the viral supernatants were collected and used for viral transduction.

Mammosphere Assay

GD2+/− of HMLE-R or MDA-MB-231 cells were FACS sorted after staining with anti-GD2 antibody (BD). To measure the mammosphere formation potential of the sorted cells (GD2+/− of HMLE-R or MDA-MB-231), 1×103 cells were plated in ultra-low attachment 24-well dishes containing mammosphere growth medium (MEGM medium with all required growth factors as described above for the growth of HMLE-R cells plus B-27 supplements, without Bovine pituitary extract (BPE)) from Lonza (Hopkinton, Mass., USA). After 12 days of culture at 37° C., the resulting mammospheres were counted. To generate mammospheres from single cells, GD2+/− from MDA-MB-231 cells were directly FACS sorted into low-attachment 96-well cell plate containing mammosphere growth medium. After 12 days of culture at 37° C., the resulting mammospheres were counted.

Microarray Analysis

GD2+/− cells of HMLE-R cells were cell sorted, and total RNA was extracted using the Qiagen mini-prep kit (Qiagen, Valencia, Calif., USA). Total RNA was analyzed on an Affymetrix human genome chip (Affymetrix, Santa Clara, Calif., USA) at the MD Anderson DNA core facility. The experiment was performed in triplicate. The statistical analysis of the Affymetrix CEL data was performed using the Bioconductor (Gentleman et al., 2004) package in the R (2009) statistical software environment. To assess differential expression the intensity values in the CEL files were transformed to RMA (Robust Multichip Average) expression measures (Irizarry et al., 2003). The RMA measure is reported in a log base 2 scale. Using the Limma R package (Smyth, 2004), linear models were fit with the lmFit function to assess differential expression between two RNA sources: $GD2^+$ vs. $GD2^-$ and $CD44^{high}CD24^{low}$ vs. $CD44^{low}CD24^{high}$ cells. To obtain empirical Bayes test statistics for each gene, including moderated t-statistics and log-odds of differential expression, the fitted model object was further analyzed using the eBayes function. Adjustment for multiple testing was based on controlling the false discovery rate (the expected proportion of false discoveries among the rejected hypotheses) by the method of Benjamini and Hochberg (Klipper-Aurbach et al., 1995). Results are reported for the top 600 differentially expressed genes for each of the comparisons.

To assess the degree of agreement between $GD2^+$ and $CD44^{high}CD24^{low}$ groups with respect to their differential expression regulation ($GD2^+$ vs. $GD^-$ and $CD44^{high}CD24^{low}$ vs. $CD44^{low}CD24^{high}$) 231 genes were identified between the two sets of top 600 differentially expressed genes. These genes were cross-classified in a two-by-two table by $GD2^+$ up/down regulation and $CD44^{high}CD24^{low}$ up/down regulation. Pearson's chi-square test with a Yates continuity correction was applied to assess the association. Statistical significance was assessed at the 0.05 level.

In Vivo Tumor Initiation Assay

Figure 11A:
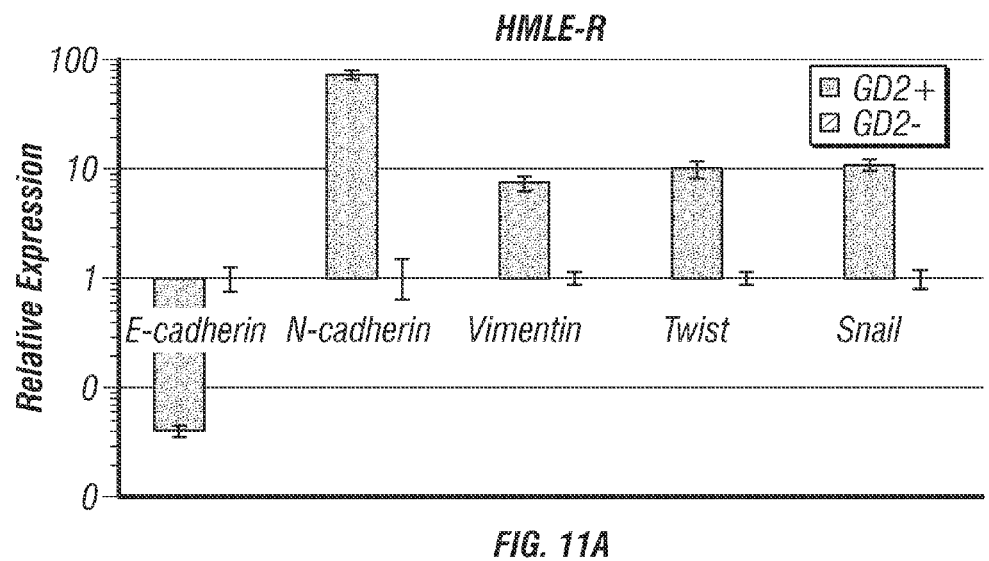
FIG. 11: Expression of EMT markers on $GD2^+$ cells. To analyze the EMT markers including E-cadherin, N-Cadherin, vimentin, Twist and Snail, $GD^{+/-}$ from HMLER (A) and MDA-MB-231 (B) cells were sorted, and total RNA was analyzed for the above mentioned markers by real-time RT-PCR.
Figure 11B:
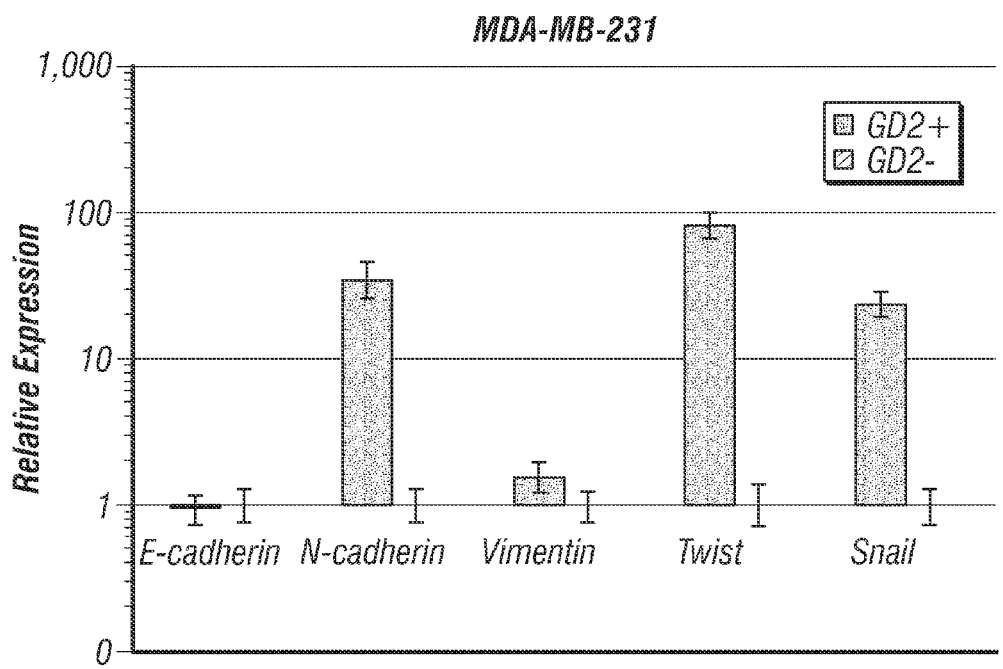

All the experiments involving animals were approved by and conducted in accordance with the animal care and use committees of M. D. Anderson Cancer Center. $GD2^{+/-}$ from MDA-MB-231 cells were FACS sorted using FACSAria-II cell sorter (BD). $GD2^{+/-}$ cells were transplanted subcutaneously into NOD/SCID mice at concentrations of 10,000, 1000, and 100 cells per site. Two injection sites were used per mouse, and 3-7 mice were used in each group. After 10-12 weeks the tumors were identified by palpation. In a similar experiment, GD3S knockdown or empty vector control MDA-MB-231 cells were subcutaneously transplanted (1×106 per site) into NOD/SCID mice to observe the tumor initiation potential. Four mice were used in this experiment, with GD3S-KD-MDA-MB-231 cells transplanted on the dorsal right and vector control cells on the dorsal left. Mice were killed after tumors reached a diameter of 1.5 cm, in accordance with institutional guidelines. To determine generation of GD− cells by GD2+ cells and vice versa in vivo, $1×10^6$ $GD2^+$ (FIG. 11A) or GD2− (FIG. 11B) GFP+ MDA-MB-231 cells were transplanted subcutaneously into NOD/SCID mice. The tumors were dissected 4 weeks after transplantation, minced and digested into single cell suspensions using collagenase-III and hyluronidase (both from Sigma). The cell suspension was analyzed using a flow cytometer.

Real-Time RT-PCR Using TaqMan Assays

To analyze the mRNA expression of GD3S and GD2S total RNA was extracted from $CD44^{high/low}CD24^{low/high}$ HMLE-R cells and $GD2^{+/-}$ HMLE-R cells. Real-time RT-PCR was performed using TaqMan gene expression assays from Applied Biosystems (Carlsbad, Calif., USA) as described previously (Konopleva et al., 2006). The assay for GD3S was Hs00268157, the assay for GD2S was B4GALNT1 and the assay for nestin was Hs00707120_s1. qRT-PCR for E-cadherin, N-Cadherin, vimentin, Snail and Twist was performed as described before (Battula et al., 2010).

In Vitro Matrigel Invasion Assay

An in vitro Matrigel invasion assay was performed using 24-well Biocoat Matrigel Invasion Chambers containing BD Falcon Cell Culture Inserts with a PET membrane (8 µm diameter pore size) that has been treated with Matrigel Matrix (BD Biosciences) as described previously (Battula et al., 2010). Briefly, MDA-MB-231 cells that were knockdown for GD3S or empty vector control cells were serum starved for 24 hr before the assay to avoid any receptor-blocking factors from serum. Cell suspensions of MDA231-vector control or MDA231-GD3S-KD were adjusted to a concentration of $15×10^4$ cells/ml, and 200 µl of the adjusted cell suspension ($3×10^4$ cells/insert) was immediately placed in the Matrigel-coated upper chamber. After incubation at 37° C. for 24 hr in a 5% $CO_2$ incubator, the residual cells on the upper surface of the filter were completely removed with cotton swabs. The membranes were then stained and cell counting was performed as described before. Each assay was performed in triplicate in three separate experiments.

Triptolide Treatments

For mRNA analysis $5×10^5$ MDA-MB-231 or SUM159 breast cancer cell lines were incubated with triptolide (Alexis Biochemicals, San Diego, Calif.) at 25, 50, 75, 100 and 125 nM concentrations for 24 hrs at 37° C. in six-well cell culture dishes. For the growth inhibition studies, $3×10^5$ MDA-MB-231 cells cultured in a 6 well tissue culture dishes were treated with triptolide at specified concentrations for either 24 hrs or 48 hrs. After incubation the cells were detached using trypsin and stained with anti-GD2 antibody (by indirect staining protocol) and pacific-blue conjugated Annexin-V (Invitrogen, Carlsbad, Calif.) following the manufactures instructions. The cells were analyzed in LSR-II flow cytometer (BD). The absolute number of cells were counted by measuring True Count® counting beads (Invitrogen) as per manufacturer's instructions. To examine tumor growth inhibition, survival of murine tumor xenografts was determined by subcutaneous administration of 1×106 MDA-MB-231 cells into 8-10 week old NOD/SCID mice. After growing for 2 weeks tumor xenografts reached a size of ~50 mm³ Thereafter, Triptolide (0.15 mg/Kg/day) was administered IP into the mice on a daily basis. The mice were sacrificed when the control tumors reached 2 cm or higher following institutional guidelines.

Statistics

Unless otherwise indicated, data are mean±SEM. Statistical significance of tumor growth was determined by 2-way ANOVA for repeated measures. All other group differences were evaluated by 2-tailed unpaired Student's t test. Survival data were analyzed using Kaplan-Meier log rank tests. A P value less than 0.05 was considered significant.

Study Approval

Animal protocols were approved by the Animal Care and Use Committees of M. D. Anderson Cancer Center. Patient tumors were obtained following written informed consent in accordance with tissue procurement protocols approved by the Institution Review Board of MD Anderson Cancer Center.

Example 2—GD2 Enriches for Breast CSCs

Figure 1C:
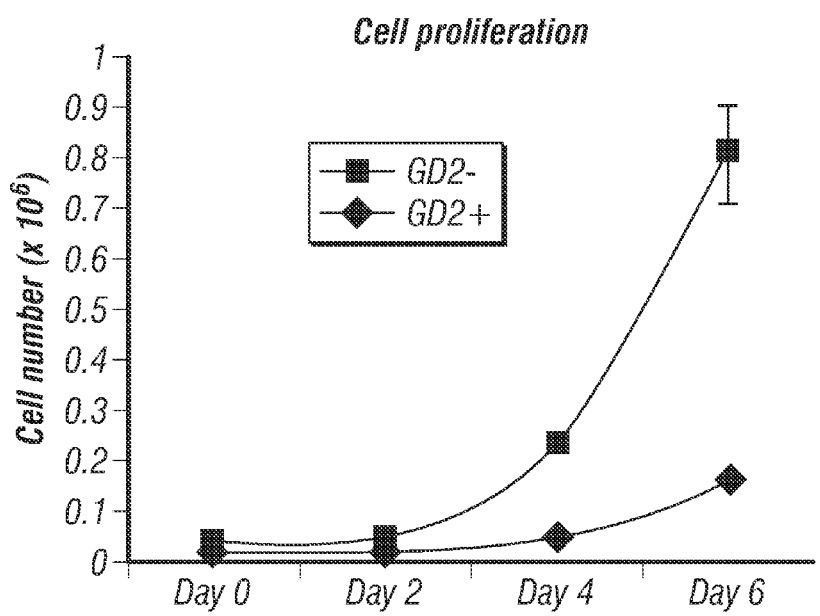
Figure 1D:
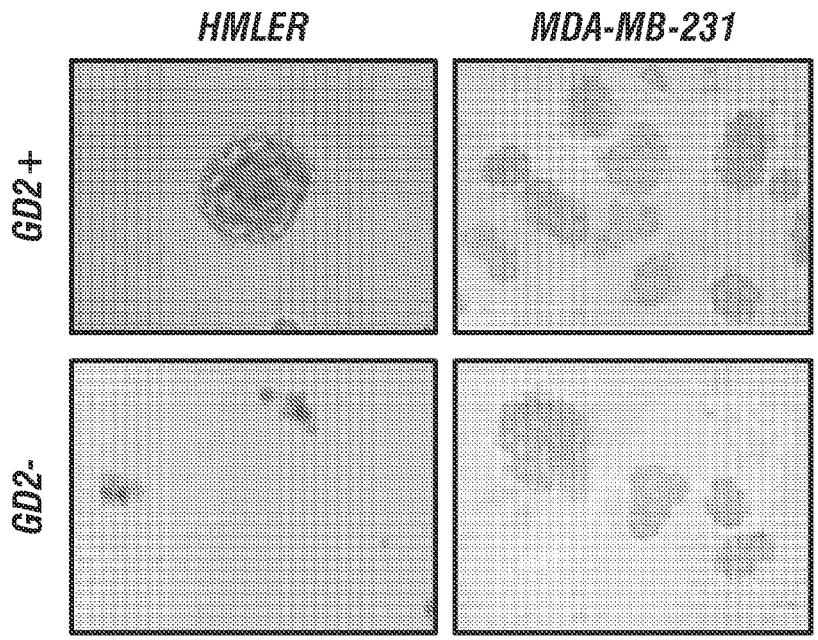
Figure 1E:
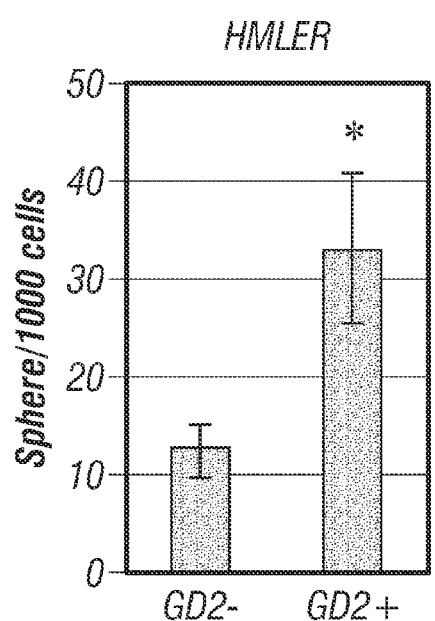
Figure 1F:
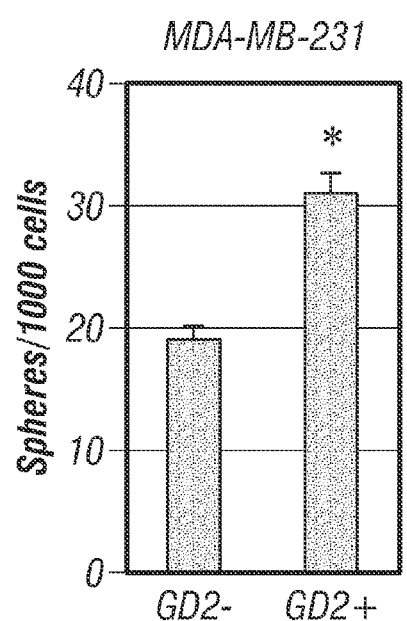
Figure 1G:
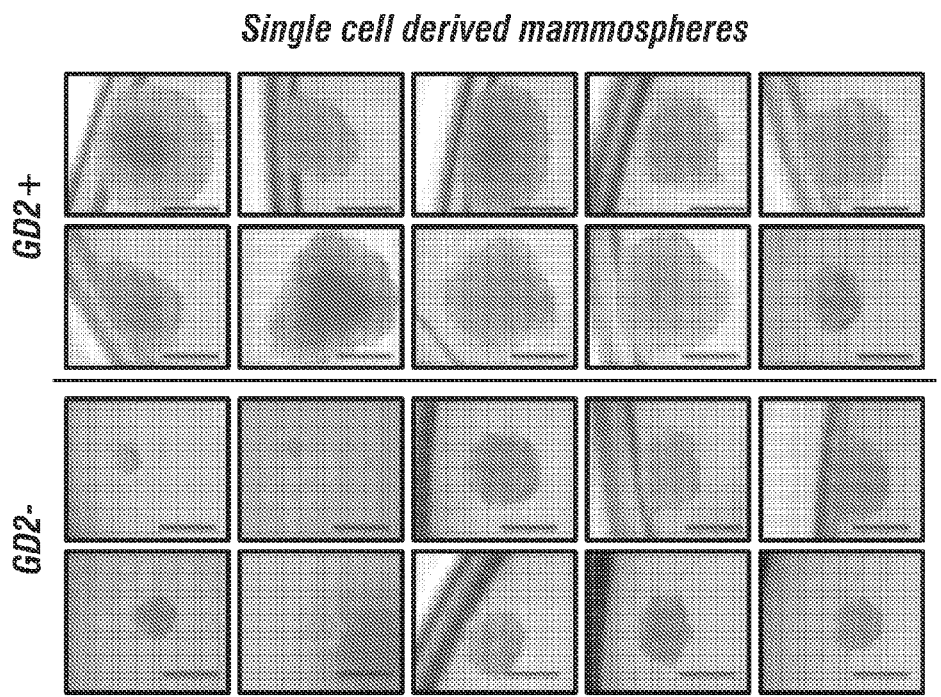
Figure 1H:
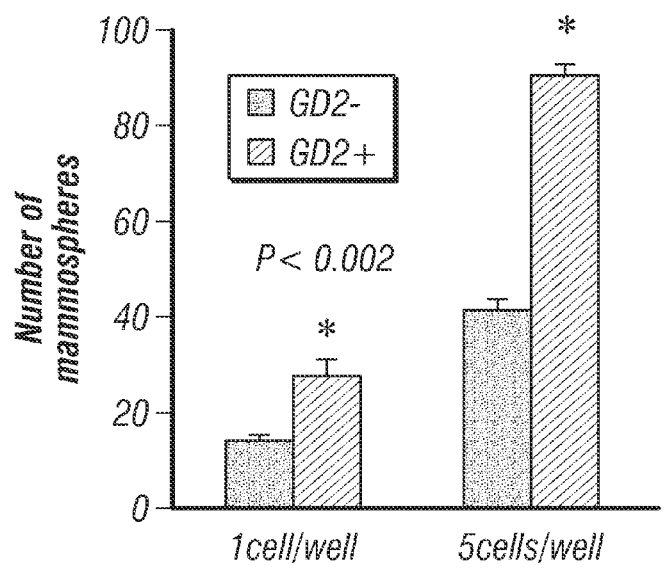
Figure 7:
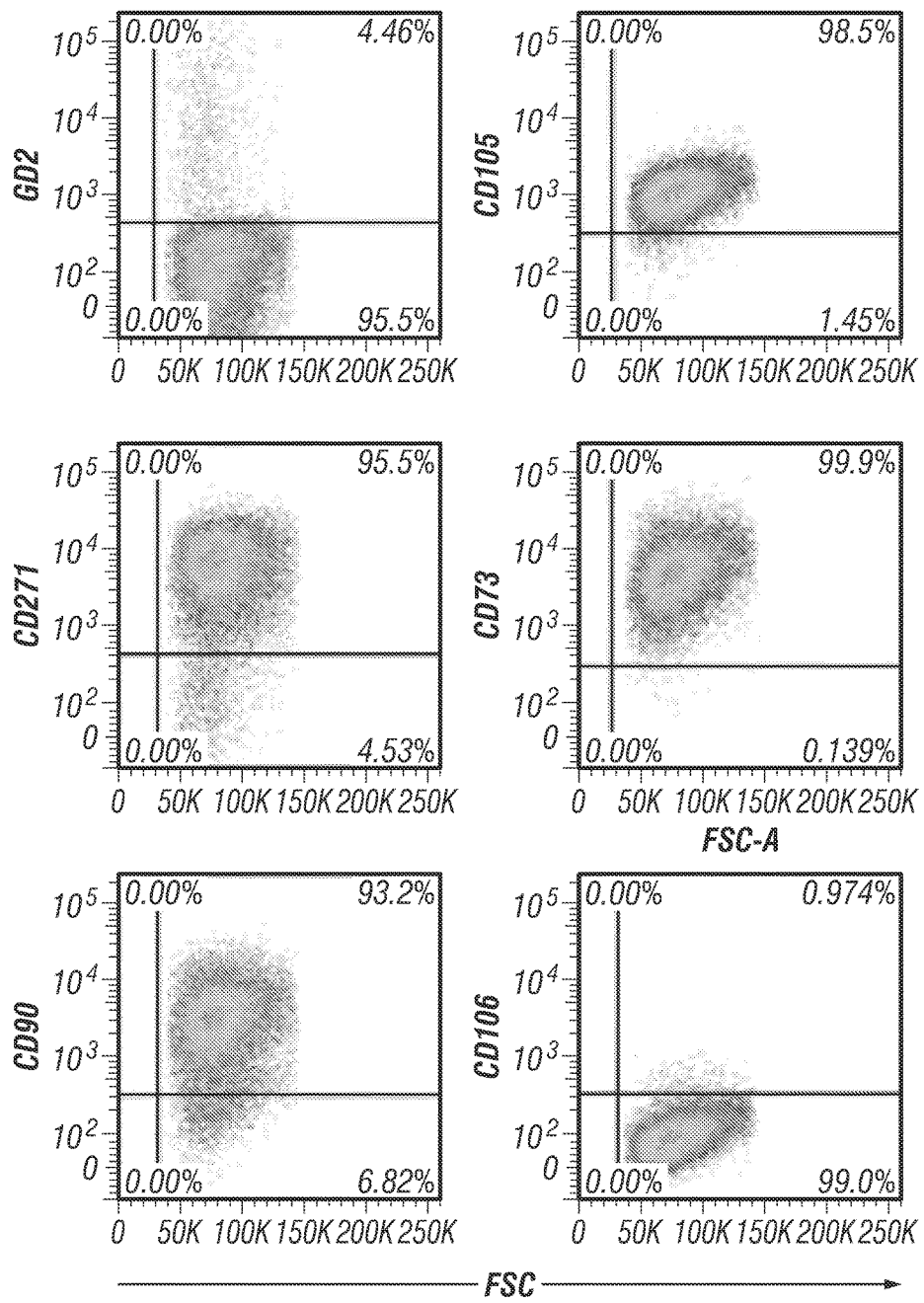
FIG. 7: Phenotypic analysis of HMLER cells. HMLER cells were stained with antibodies as indicated in the FIG. Data was acquired using LSR-II flow cytometer and analyzed using Flow Jo data analysis software.
Figure 7:
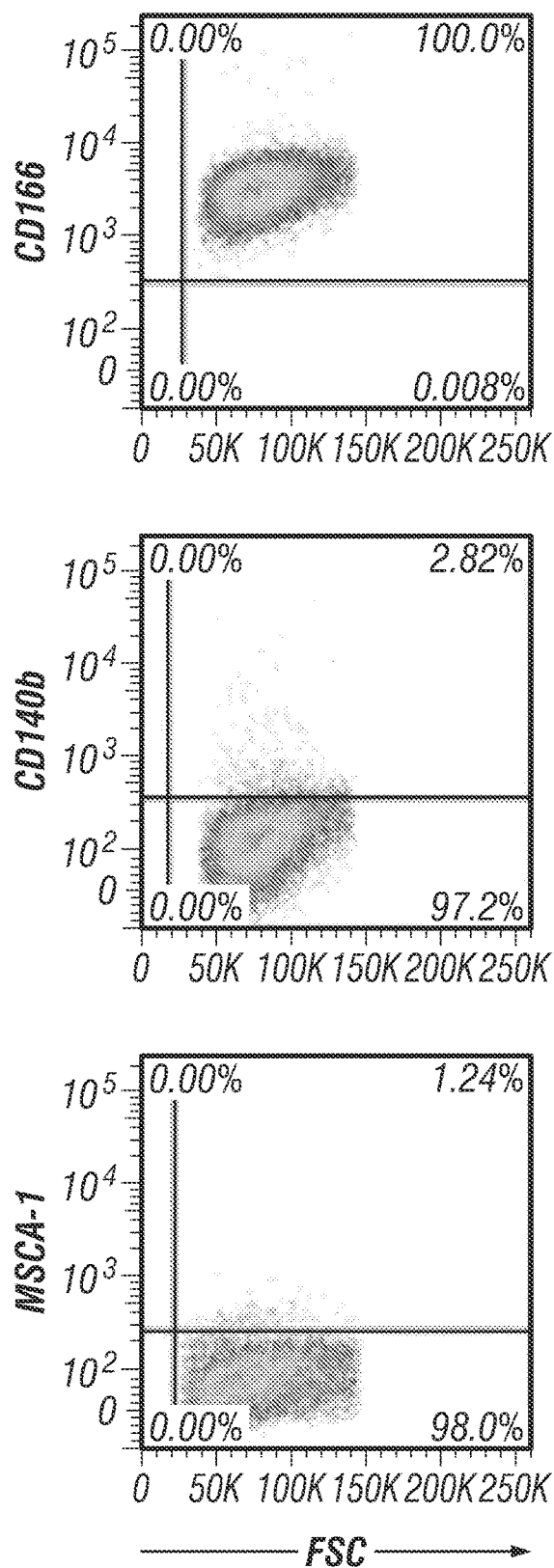

It was recently reported that, following the induction of EMT, human mammary epithelial cells (HMECs) behave functionally similar to human bone marrow-derived mesenchymal stem cells (MSCs) (Battula et al., 2010). Therefore, it is hypothesized that the cell markers expressed on the surface of MSCs could also be expressed on the surface of breast CSCs. To test this hypothesis, the expression of several known MSC cell surface markers was analyzed (i.e. CD105, CD90, CD106, CD166, CD73, CD271, MSCA-1 and GD2) on HMECs that have been experimentally transformed to become tumorigenic using oncogenic V12-H-Ras (HMLER) (Elenbass et al., 2001). Absolute expression of most of the markers analyzed could not divide HMLER cells into 2 distinct subpopulations (FIG. 7) similar to $CD44^{high}/CD24^{low}$ (Mani et al., 2008). However, Ganglioside GD2, one of the cell surface markers for MSCs, is able to separate HMLERs into $GD2^+$ (4.5±2.4%) and $GD2^-$ (92.7±3.8%) populations (FIG. 7, FIG. 1A). Strikingly, $GD2^+$ HMLERs isolated using FACS appeared spindleoid with limited cell-cell contacts, conversely, the $GD2^-$ cells displayed cobblestone epithelial morphology (FIG. 1B). Moreover, the $GD2^+$ HMLERs proliferated ~5 fold slower than the $GD2^-$ HMLERs (FIG. 1C).

To further investigate the functional properties of $GD2^+$ and $GD2^-$ cells, HMLER and MDA-MB-231 cells were sorted based on GD2 expression and examined them by mammosphere assay. Interestingly, the $GD2^+$ cells from HMLER and MDA-MB-231 cells formed 2-fold more mammospheres compared to $GD2^-$ cells (FIGS. 1 D&E, p<0.01). Direct sorting of $GD2^+$ and $GD2^-$ MDA-MB-231 cells into low-attachment 96-well plates at cell numbers of either 1 or 5 cells per well also resulted in a 2-fold increase in sphere formation by $GD2^+$ cells regardless of the number of cells per well compared to $GD2^-$ cells (FIGS. 1 G&H). In addition, the mammospheres generated by $GD2^+$ cells are 3-times larger than those generated by $GD2^-$ cells (FIGS. 1G and I), indicating that the $GD2^+$ cells are capable of growing better in suspension cultures.

Figures 1I, 1J:
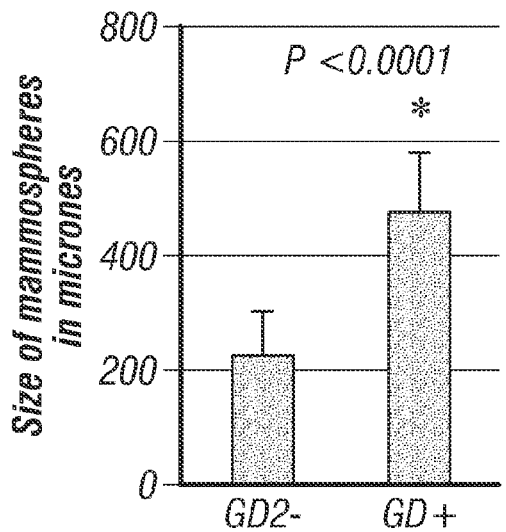
Figure 8:
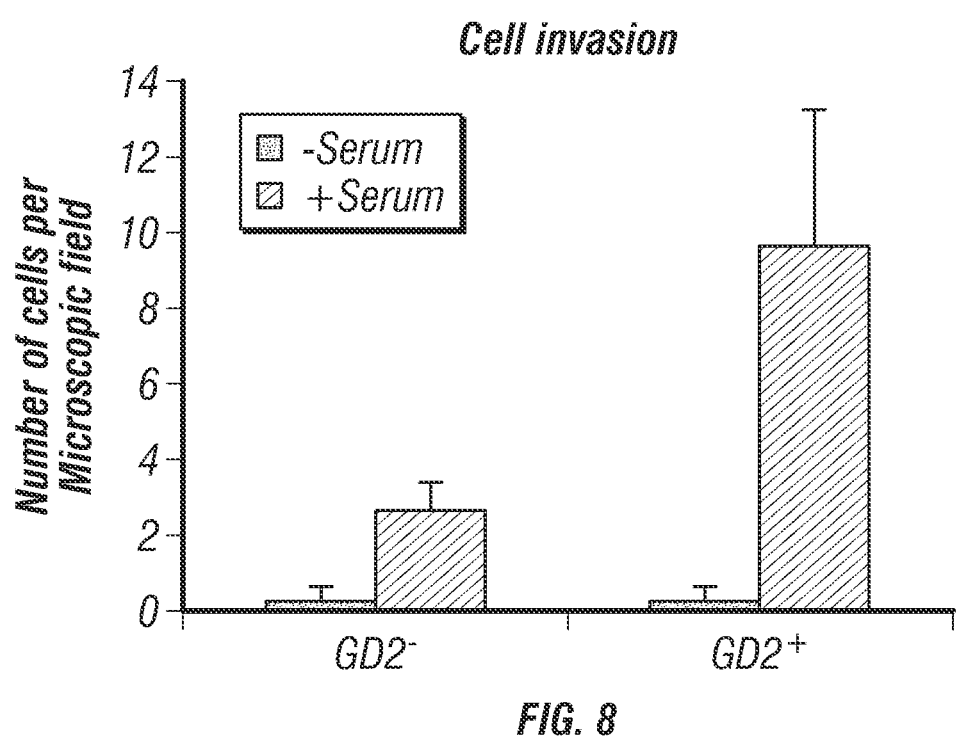
FIG. 8: $GD2^+$ cells possess higher matrigel invasion potential. To measure the invasion potential, $1 \times 10^4$ $GD^{+/-}$ HMLER cells were seeded on upper invasion chamber and incubated for 24 hrs in the presence or absence of 30% serum. Membranes were collected and cells were counted as described in methods.

CSCs are known to be more migratory and invasive (Rosen and Jordan, 2009; Schatton et al., 2009). To examine the migration and invasion potential of $GD2^{+/-}$ cells, HMLER cells were fractionated into $GD2^+$ and $GD2^-$ cells and analyzed for migration and invasion using Boydenchamber matrigel invasion assay chambers. After 24 hrs of incubation, $GD2^+$ HMLER cells migrated more than 4-fold more compared to $GD2^-$ cells indicating that $GD2^+$ cells are highly migratory (FIG. 8). The hallmark of CSCs is their ability to initiate tumor better than their bulk tumor counterparts (Rosen and Jordan, 2009; Schatton et al., 2009). To determine the tumor initiating potential of $GD2^+$ cells, $GD2^+$ and $GD2^-$ MDA-MB-231 cells were sorted and transplanted them subcutaneously into the flank of NOD/SCID mice at limiting dilutions. At lower cell dilutions including 100 or 10 cells/site, the $GD2^+$ cells generated tumor 2 and 5 fold more tumor incidence compared to GD2-fraction respectively (FIG. 1J). However, at higher cell numbers (10,000 or 1000 cells/site), there were no significant differences in tumor initiation between $GD2^+$ and $GD2^-$ cells. These data firmly established that GD2 is a marker of cells capable of initiating tumors at a higher frequency than cell without GD2.

Example 3—Percentage of $GD2^+$ Cells is Highest in Cell Lines with a Basal Molecular Signature On the basis of gene expression profile (Neve et al., 2006), breast cancer cell lines have been classified into three groups: luminal, basal-A, and basal-B. 12 breast cancer cell lines were randomly selected representing these three subgroups and analyzed for GD2 expression. Interestingly, the majority of these lines, independent of the subgroups, contained a subpopulation of $GD2^+$ cells at variable levels (Table 1). However, basal cell lines contain a much higher number (mean 9%, range 1.2-17%, n=6) of GD2+ cells compared to luminal cell lines (median 0.2%, range 0-3%, n=6, Table 10A, p=0.00237). Since basal-derived cell lines are better in tumor initiation and contain more CSCs based on the previously reported $CD44^{high}/CD24^{low}$ profiles (Sorlie et al., 2001), this finding once again confirms GD2 as a stem cell marker.

For the studies summarized in Table 10A Breast cancer cell lines were stained with anti-GD2, CD44-APC, and CD24-FITC as shown in FIG. 1A. The percentage of CD44/CD24/GD2 for each cell type is shown in separate columns. The cells were divided into three groups based on the origin: luminal, basal-A, and basal-B. The intensity of the marker expression is denoted as high/med/low based on the mean fluorescence intensity (MFI) of individual markers. 'High' indicates >1000 MFI; 'Med' indicates 100-1000 MFI; 'Low' indicates 20-100 MFI; 'Neg' indicates negative staining. The cells were analyzed on an LSR-II flow cytometer. Cells from a range of primary tumors were also assessed to determine the percentage of cells that were GD2 positive. For these in Table 10B, GD2 expression was assessed using flow cytometry of cells labeled with the 14g2a anti-GD2 antibody.

TABLE 10A

Expression of GD2 in breast cancer cell lines

| # | Cell line | Gene cluster | Percent of CD44+ cells & expression level | Percent of CD24+ cells & expression level | Percent of GD2+ cells & expression level |
|---|---|---|---|---|---|
| 1 | MCF-7 | Luminal | 35% ± 3% (Med) | 100% (High) | 1.6% ± 0.2% (Low) |
| 2 | MDA-MB-453 | Luminal | 0% (Neg) | 83% ± 4% (High) | 0% (Neg) |
| 3 | SKBR3 | Luminal | 0.5% ± 0.1% (Low) | 100% (High) | 0.3% 0.1% (Low) |
| 4 | BT474 | Luminal | 11% ± 1% (Med) | 100% (High) | 0.1% ± 0.1% (Low) |
| 5 | ZR751 | Luminal | 68% ± 4% (Med) | 56% ± 3% (Med) | 3% ± 0.3% (Med) |
| 6 | MDA-MB-361 | Luminal | 0% (Neg) | 100% (High) | 0% (Neg) |
| 7 | BT20 | Basal-A | 94% ± 3% (High) | 78% ± 4% (High) | 7% ± 1% (Med) |
| 8 | MDA-MB-468 | Basal-A | 96% ± 3% (High) | 99.6% ± 0.2% (High) | 9% ± 1% (High) |
| 9 | MDA-MB-231 | Basal-B | 100% (High) | 0% (Neg) | 9.7% ± 3% (High) |
| 10 | HS578T | Basal-B | 100% (High) | 0% (Neg) | 8.5% ± 3% (Med) |
| 11 | Sum159 | Basal-B | 100% (High) | 0% (Neg) | 17% ± 1% (High) |
| 12 | Sum149 | Basal-B | 100% (High) | 100% (High) | 1.2% ± 0.1% (low) |

TABLE 10B

Expression of GD2 in primary cancers

| Patient # | Type of breast cancer | Percent of GD2+ cells |
|---|---|---|
| 1 | Metastatic adenocarcinoma | 18% ± 3% |
| 2 | High-grade malignant neoplasm | 3.5% ± 0.6% |
| 3 | Lobular carcinoma | 0.5% ± 0.1% |
| 4 | Invasive ductal carcinoma | 7.5% ± 0.6% |
| 5 | Invasive ductal carcinoma | 2.2% ± 0.3% |
| 6 | Invasive ductal and lobular carcinoma | 5.5% ± 1.1% |
| 7 | Invasive ductal carcinoma | 16.2% ± 1.3% |
| 8 | Invasive lobular carcinoma | 2.4% ± 0.2% |
| 9 | Ductal carcinoma in situ | 1.1% ± 0.2% |
| 10 | Invasive lobular carcinoma | 5.2% ± 1.5% |
| 11 | Metastatic adenocarcinoma | 35.8% ± 2.1% |
| 12 | Invasive lobular carcinoma | 2.4% ± 0.3% |

Figure 2A:
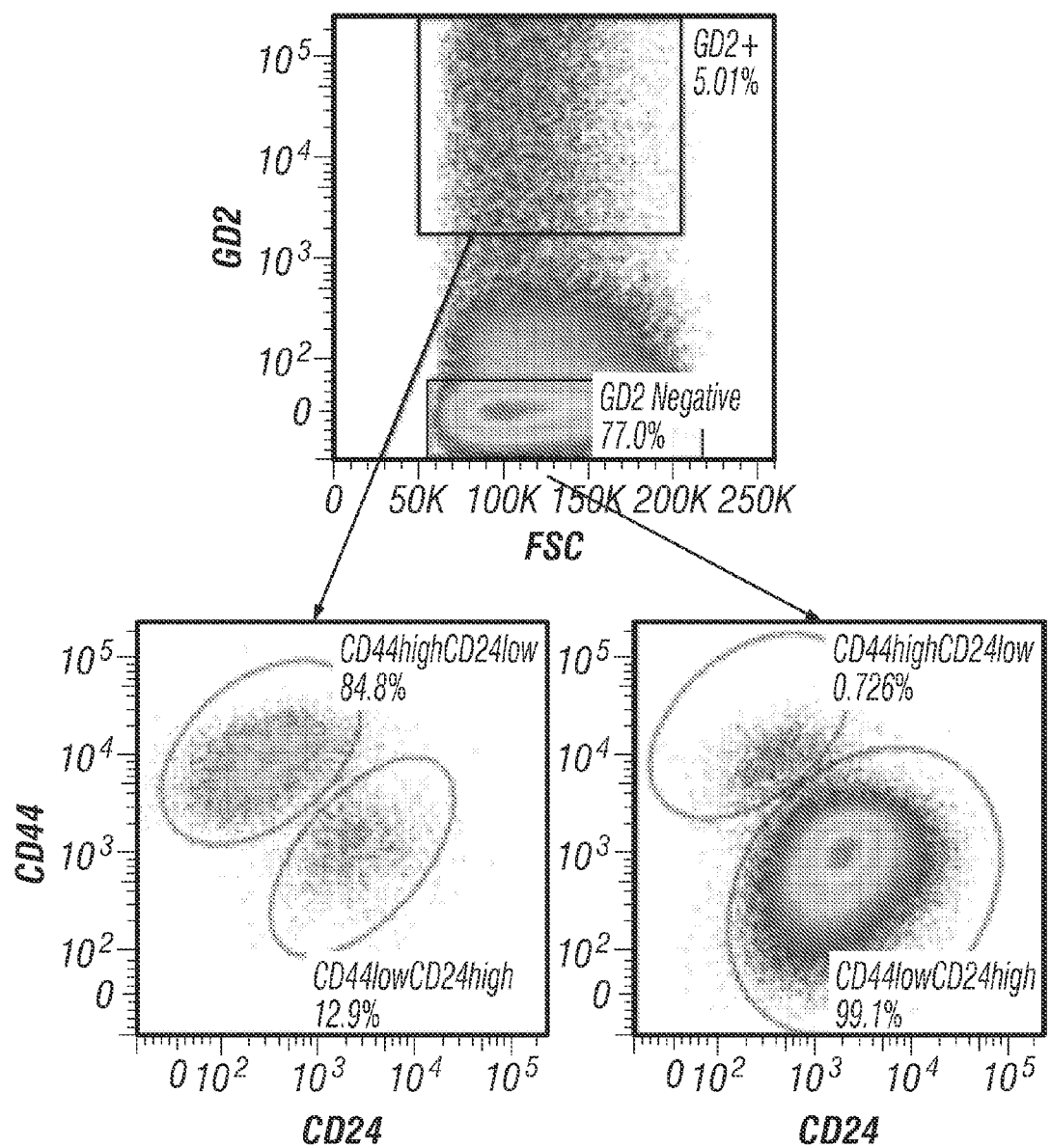
FIG. 2: GD2 identifies $CD44^{high}CD24^{low}$ stem cell phenotype in breast cancer cells. (A) HMLER cells were stained with anti-GD2 antibody and with CD44-APC, CD24-FITC using the four-step staining protocol as described in Example 1. Cells were electronically gated on $GD2^{+/-}$ cells and displayed in pseudo color dot plot with CD44 on Y-axis and CD24 on X-axis using FlowJo data analysis software. (B) In an identical experiment, $CD44^{high/low}CD24^{low/high}$ cells were displayed on pseudo color dot plot with GD2 on Y-axis and forward scatter (FSC) on X-axis. (C) Table showing the details of breast cancer patient samples analyzed: patient number, tumor type, percentage of GD2+ cells. (C) Percentage of GD2+ cells for each breast cancer patient, tumor type and estrogen receptor (ER), progesterone receptor (PR) and HER2/neu status are included. 'NA' represents non availability of patient information for the respective parameter. (D) Primary breast tumor samples were processed as described in the Experimental Procedures, and the single cells in suspension were stained with anti-GD2, CD44-APC, CD24-FITC, CD45-FITC and DAPI using the four-step staining protocol. Cells were initially gated on DAPI-negative cells to exclude dead cells, and the cells were then gated on CD45– cells to exclude hematopoietic cells. $GD2^+CD45^-$ cells were displayed on a dot plot, with CD44 on the y-axis and CD24 on the x-axis. Analysis was perfumed using LSR-II flow cytometer. Data was analyzed using FlowJo software.
Figure 2B:
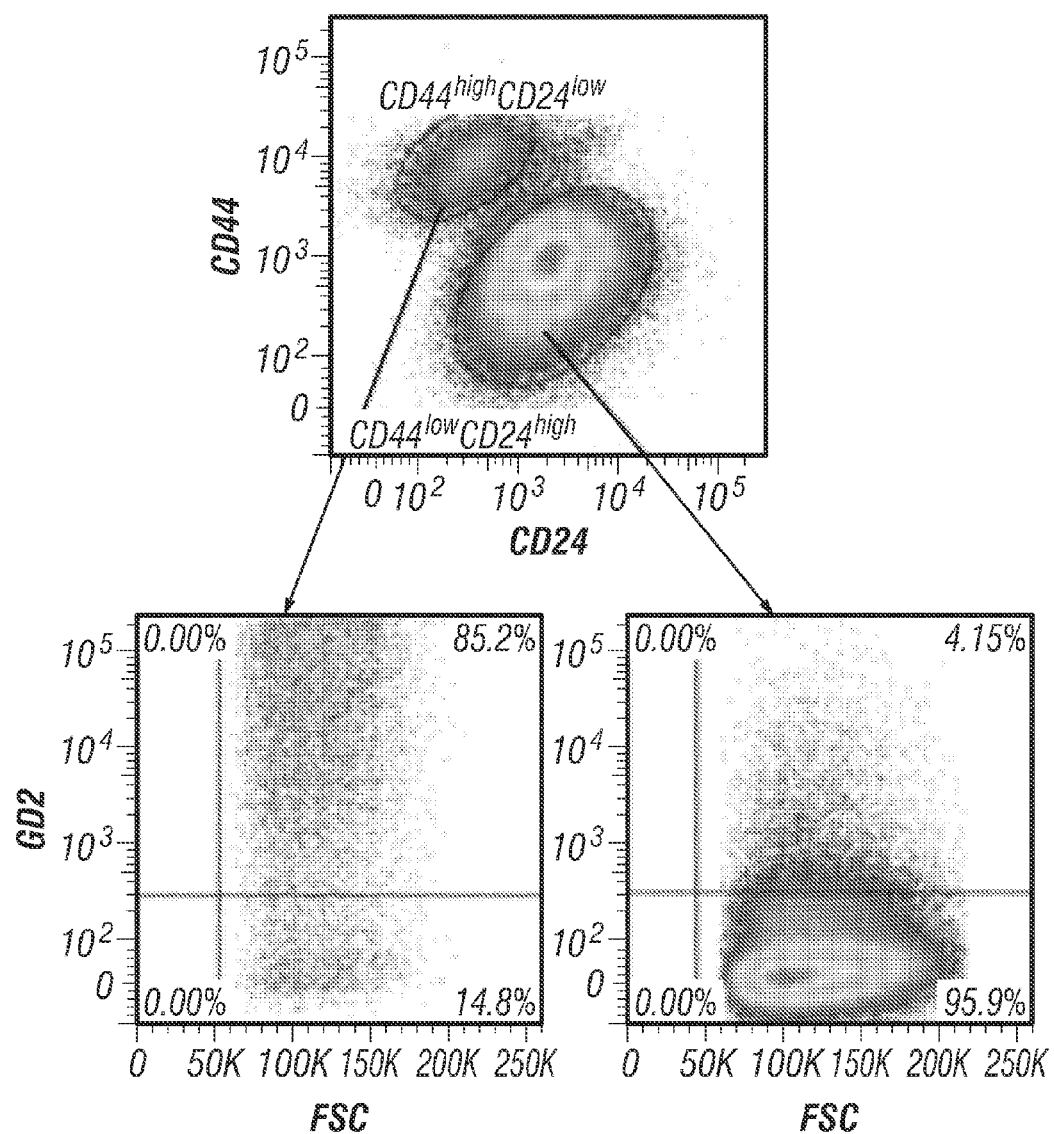
Figure 9A:
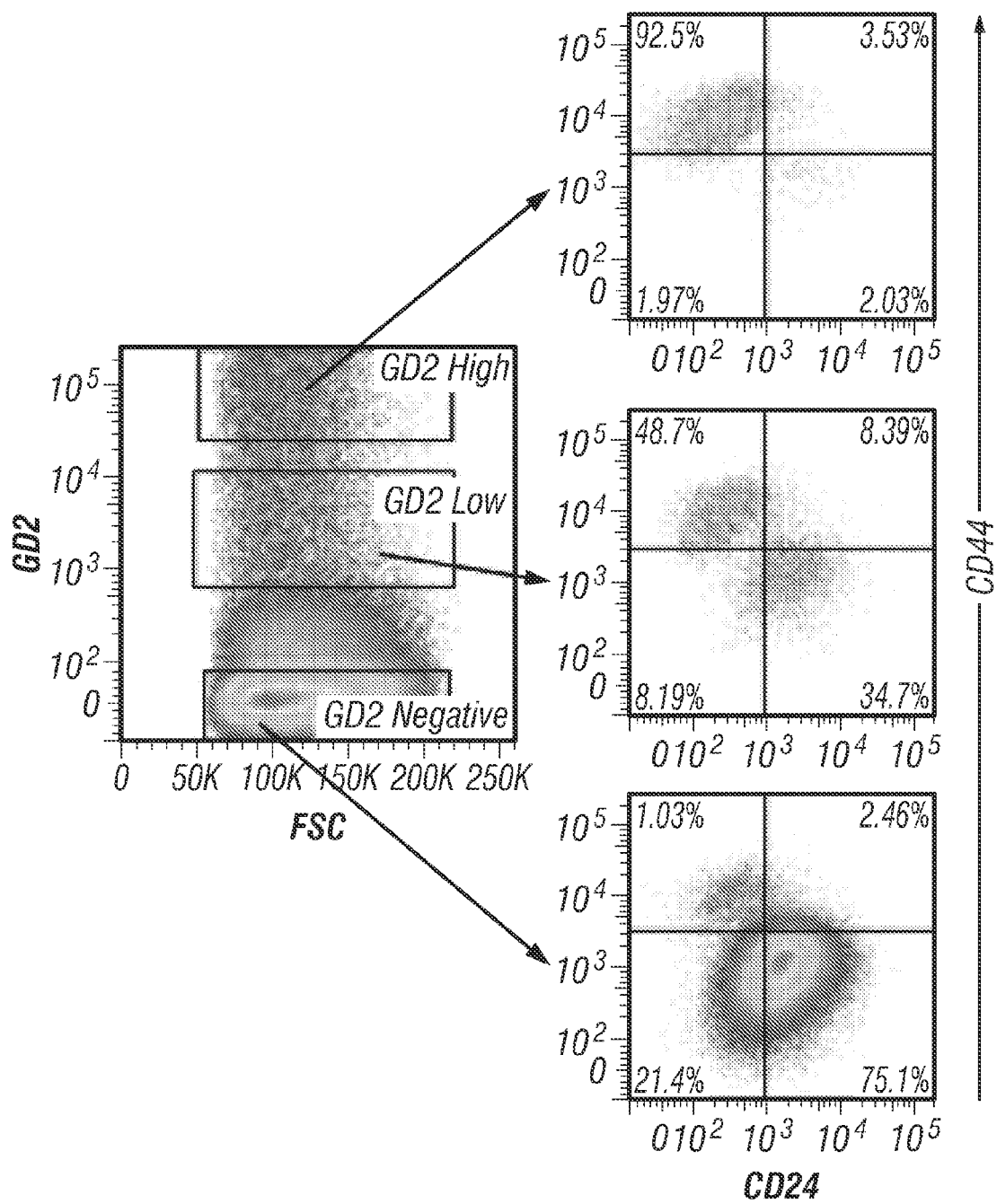
FIG. 9: GD2 identifies $CD44^{high}CD24^{low}$ phenotype. (A) In an identical experiment as shown in FIG. 2A-B, cells were stained with anti-GD2, anti-CD44 conjugated with APC, and anti-CD24 conjugated with FITC antibodies and gated on $GD2^{high/low/negative}$ regions of a contour plot and displayed as a color dot plot, with CD44 on the y-axis and CD24 on the x-axis. Dead cells were excluded by gating on DAPI-negative cells (live cells, not shown). (B) Mean fluorescence intensity (MFI) of anti-CD44-antibody on $GD2^{high/low/negative}$ cells was plotted as bar graphs. ($p<0.0001$).
Figure 9B:
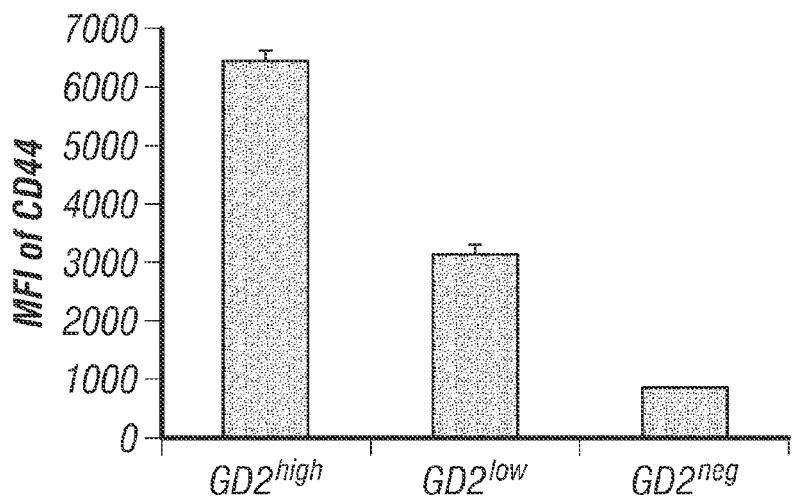
Figure 10:
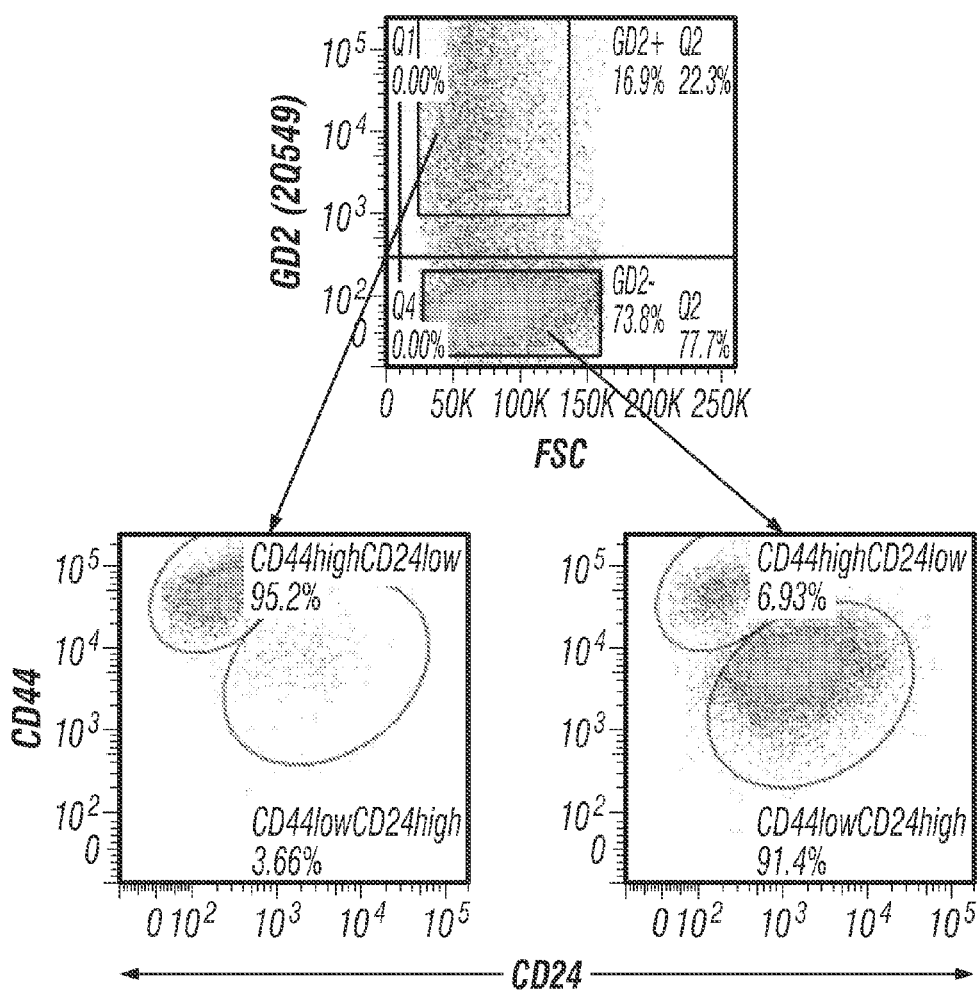
FIG. 10: Anti-GD2 antibody (clone#2Q549) identifies $CD44^{high}CD24^{low}$ breast cancer stem cells. In an identical experiment to FIG. 2A-B, HMLER cells were stained with anti-GD2 antibody (2Q549) in addition to anti-CD44 conjugated with APC and anti-CD24 conjugated with FITC antibodies and analyzed on LSR-II flow cytometer. $GD2^{+/-}$ cells were gated and plotted against CD44 (y-axis) and CD24 (x-axis) by using flow Jo data analysis software.

Example 4—GD2 Identifies the $CD44^{high}/CD24^{low}$ Population in Breast Cancer Cell Lines and Patient Samples Since it was found that GD2 is capable of separating cancer cells into two populations with differing tumor initiating potential similar to previously reported CD44 and CD24 cell surface markers (Al-Hajj et al., 2003), it was hypothesized that GD2 would be mostly expressed in the $CD44^{high}/CD24^{low}$ cancer cell fraction. To test this, the expression of $CD44^{high}CD24^{low}$ in $GD2^+$ HMLERs cell was analyzed and it was found that more than 85 percent (85±3.5%) of $GD2^+$ HMLERs also displayed $CD44^{high}/CD24^{low}$ CSC profile, whereas less than 1% (0.7%±0.2%) of $GD2^-$ HMLERs were $CD44^{high}/CD24^{low}$ (FIG. 2A). In addition, through reverse gating analysis of $CD44^{high}/CD24^{low}$ HMLERs cells, it was noted that more than 84 percent (84%±2.5%) of $CD44^{high}CD24^{low}$ HMLERs were also positive for GD2 (FIG. 2B), whereas less than 5 percent of $CD44^{low}/CD24^{high}$ HMLERs were $GD2^+$ (4.3±1.2%). To further determine the correlation between the expression of GD2 and the CD44/CD24 profiles, HMLERs were sequentially gated into $GD2^{high}$, $GD2^{low}$, and $GD2^{negative}$ cells. This analysis revealed that GD2 expression levels correlates strongly with $CD44^{high}CD24^{low}$ phenotype (FIG. 9A). Moreover, by determining the mean fluorescence intensity (MFI), it was found that GD2 expression levels correlated positively with CD44 expression (correlation index $r^2$=0.85, p<0.0003; FIG. 9B). To validate the co-expression of GD2 on $CD44^{high}CD24^{low}$ cells, anti-GD2 antibody from another source (abcam, clone 2Q549) was used to stain HMLER cells in 4-step staining procedure as explained before along with anti-CD44 and anti-CD24 antibodies. Analysis of $GD2^+$ cells revealed that these cells co-express $CD44^{high}CD24^{low}$ phenotype, confirming the initial findings with 14G2a clone (FIG. 10).

Figure 2D:
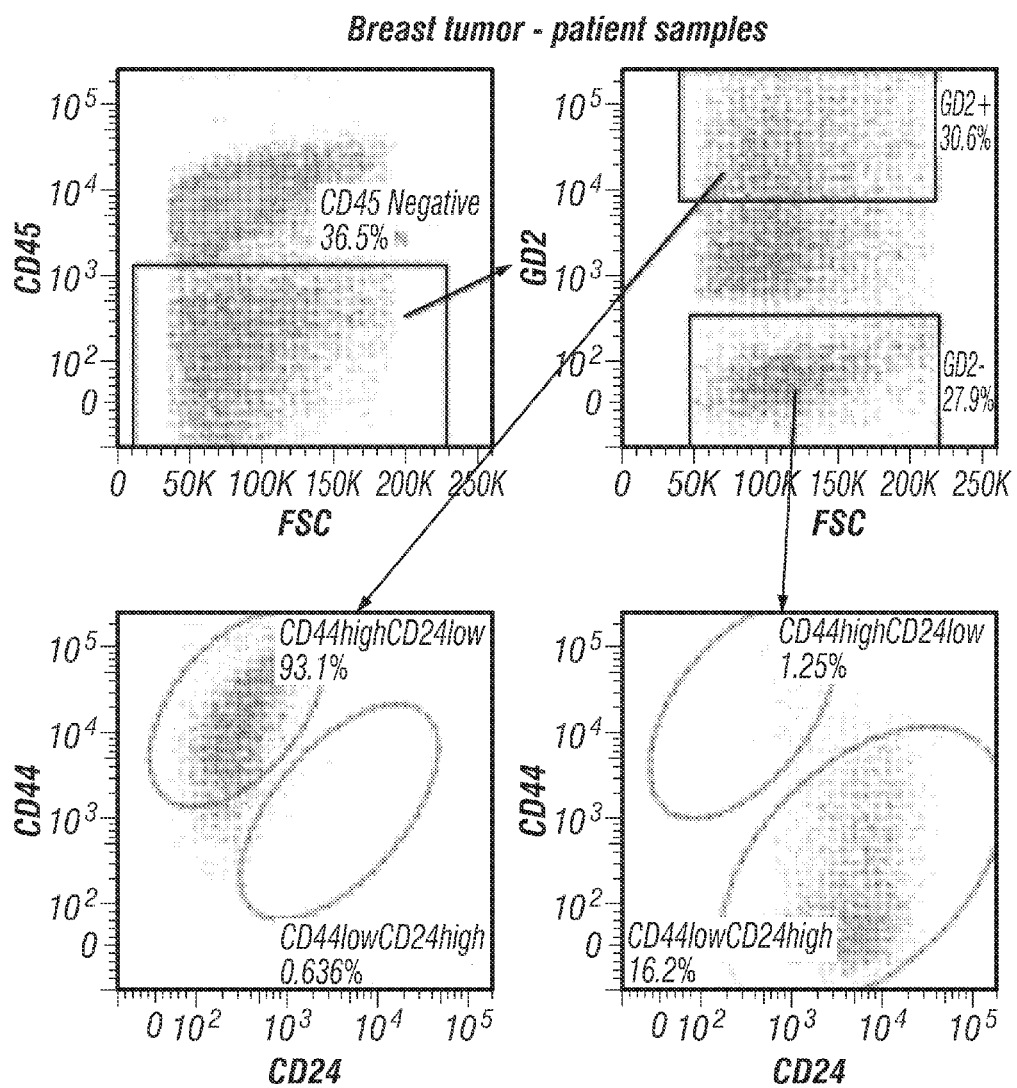

To further investigate the correlation between GD2 expression and the $CD44^{high}/CD24^{low}$ profile, primary breast tumor samples (n=12) were also analyzed. Using multi-parameter flow cytometry, $CD45^+$ inflammatory and other hematopoietic cells were excluded from dissociated tumor samples. The non hematopoietic $CD45^-$ was then analyzed for the expression of GD2, CD44, and CD24. This analysis of the $CD45^-$ fraction revealed that GD2 is expressed, at variable levels from 0.5 to 35 percent (median 4.35, range 0.5 to 35.8%), in tumor samples (FIG. 2C). Importantly, similar to cell lines, more than 95.5 percent (95.5±2.7%) of $GD2^+CD45^-$ tumor cells also co-segregated with $CD44^{high}CD24^{low}$ phenotype (FIG. 2D). In contrast, only 2.4 percent (2.4±0.4%) of $GD2^-CD45^-$ cells exhibited the $CD44^{high}CD24^{low}$ phenotype (FIG. 2D). Together these findings clearly indicated that GD2 is a marker of a subset of cancer cells with stem cell properties. To validate that the identified $GD2^+$ cells are in fact tumor cells and not mesenchymal stromal cells (MSCs), human breast tumors tissues were stained with anti-GD2 and epithelial specific anti-Pan Cytokeratin antibodies. Co-expression of both GD2 and cytokeratin was observed in some of the breast cancer cells suggesting that GD2 identifies breast tumors cells. Specifically, for these studies, breast tumor sections (from 2 different cases of triple negative breast cancer samples) were stained with anti-GD2 and anti-pan-Cytokeratin antibodies and an immuno-fluorescence assay was performed as described in Example 1.

Figure 3A:
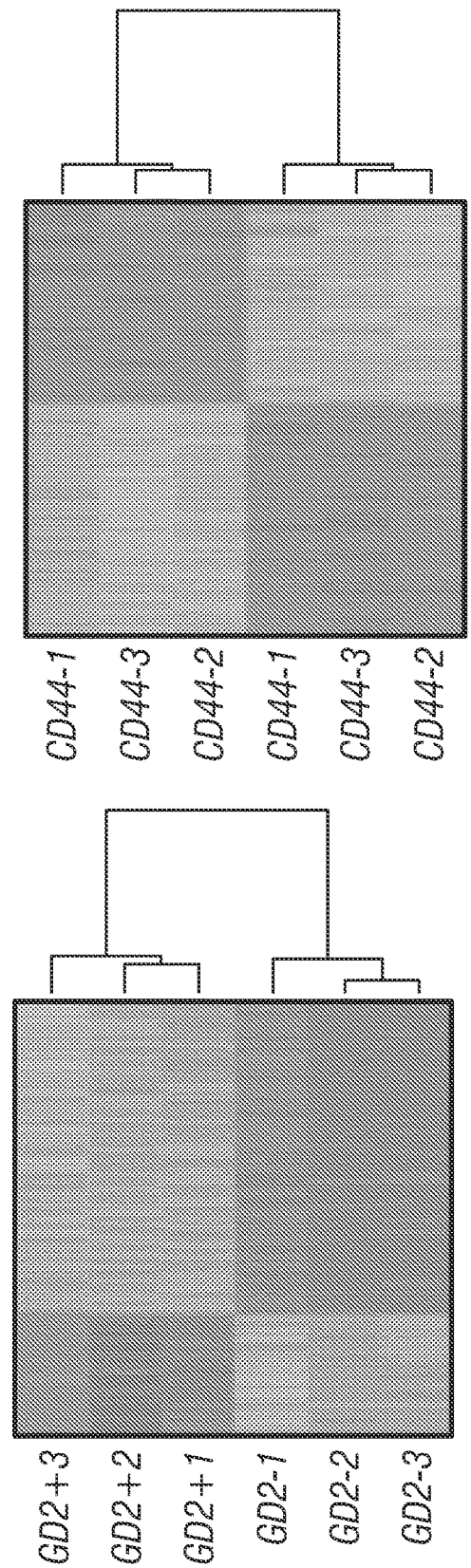
FIG. 3: $GD2^+$ and $CD44^{high}CD24^{low}$ Cells Share Similar Gene Signature. (A) Heat maps derived from microarray analysis of $CD44^{high/low}CD24^{low/high}$ (top panel) and $GD2^{+/-}$ (bottom panel) of HMLER cells. (B) Two hundred thirty-one genes of the top 600 differentially expressed genes were identical between $GD2^+$ vs. $GD^-$ and $CD44^{high}CD24^{low}$ vs. $CD44^{low}$ vs. $CD24^{high}$ groups. These genes were cross-classified in a two-by-two table by $GD2^+$ up/down regulation and $CD44^{high}CD24^{low}$ up/down regulation. Pearson's chi-square test with a Yates continuity correction was applied to assess the association. Statistical significance was assessed at the 0.05 level. (C) Biosynthesis reaction of GD2. (D & E) To measure the expression of GD2-/GD3-synthase mRNA, $CD44^{high}CD24^{low}$ or $CD44^{low}CD24^{high}$ and $GD2^{+/-}$ cells from HMLER (D) or MDA-MB-231 cells (E) were FACS sorted, and mRNA was analyzed using real-time RT-PCR.
Figure 3B:
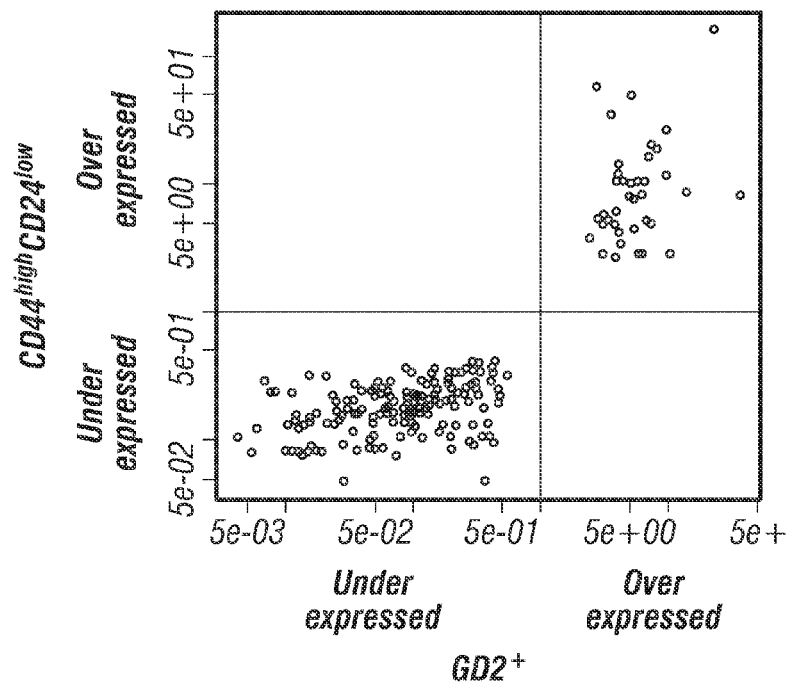
Figure 3C:
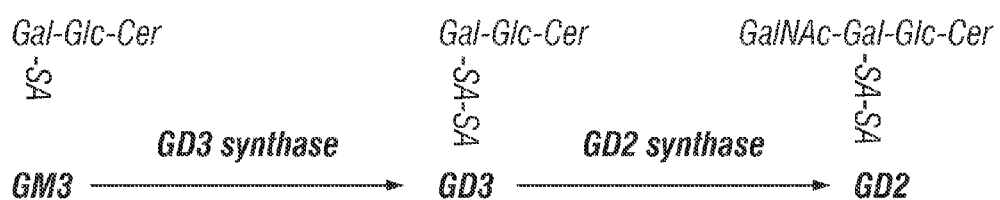

Example 5—GD2$^+$ and CD44$^{high}$CD24$^{low}$ Cells have Highly Similar Gene Signatures Since it was found that GD2 is capable of independently enriching for CSCs as single marker compared to previously known double markers CD44$^{high}$CD24$^{low}$, the global gene expression profiles between these two populations isolated from HMLER cells were compared using microarray analysis. Initial comparison of the GD2$^+$ fraction with the GD2$^-$ fraction of cells (GD2 set) and the CD44$^{high}$/CD24$^{low}$ with CD4$^{low}$/CD24$^{high}$ fraction (CD44 set) identified gene signatures specific to the GD2$^+$ and CD44$^{high}$/CD24$^{low}$ fractions (FIG. 3A). Comparison of the top 600 differentially expressed genes in the GD2 set and CD44 set identified 231 genes that are being identical between the two sets. In addition, a Pearson's chi-square test was applied with a Yates continuity correction to assess the association between these two cell types and found that the identified 231 genes correlated (100%) between the two groups described above (FIG. 3B). This gene expression analysis along with previous cell surface protein analysis from FIG. 2 indicated that GD2$^+$ cells share not only functional properties but also a gene signature with CD44$^{high}$CD24$^{low}$ cells.

Figure 3D:
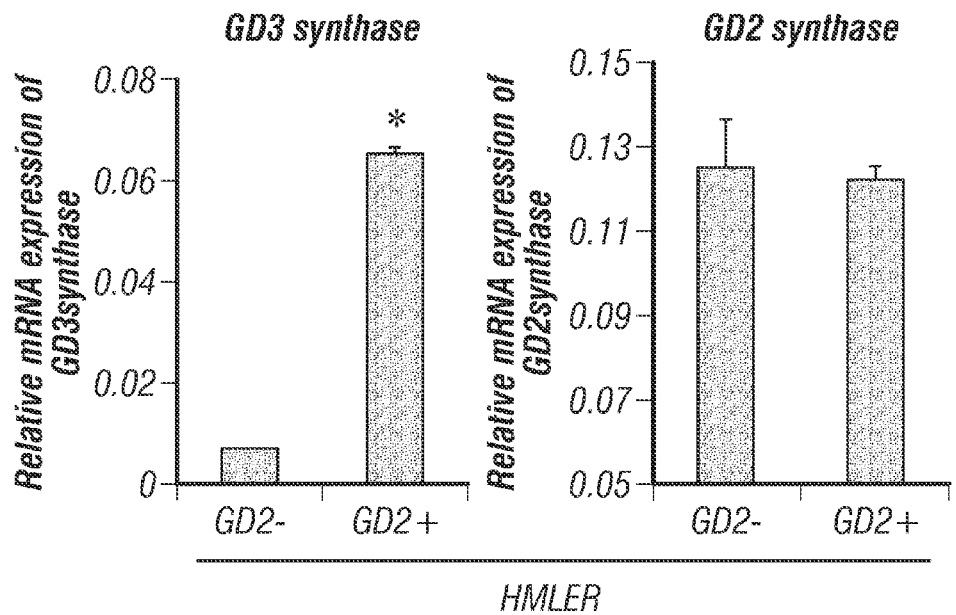
Figure 3E:
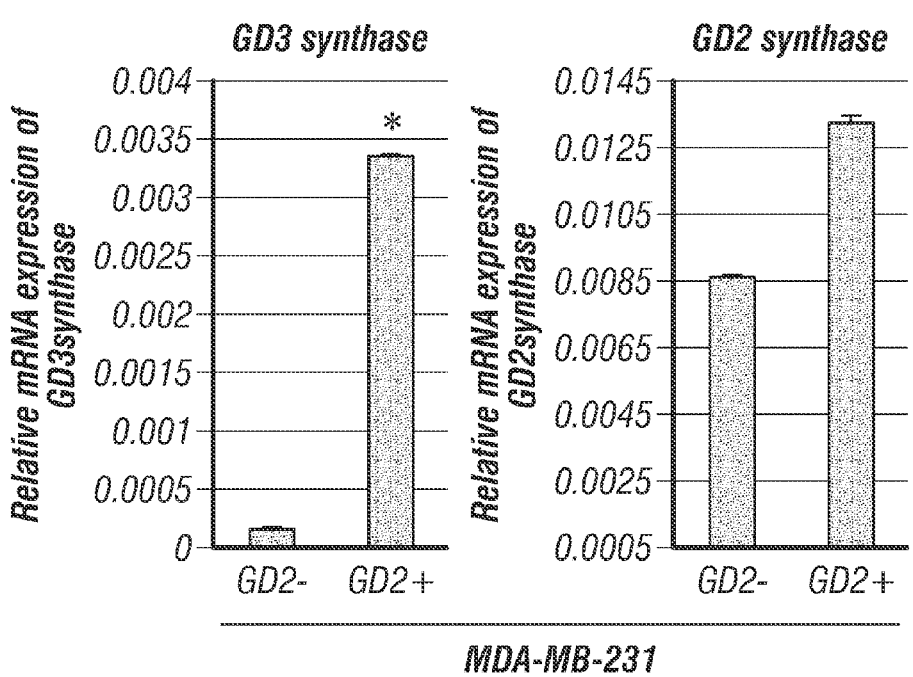
Figure 12:
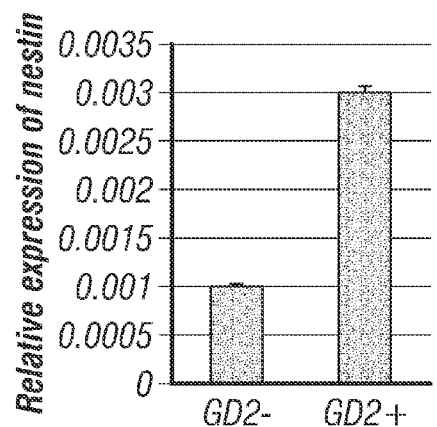
FIG. 12: $GD2^{+/-}$ MDA-MB-231 cells spontaneously produce $GD2^{-/+}$ cells in vivo. To demonstrate spontaneous generation of $GD2^{+/-}$ cells from $GD2^{-/+}$ cells, $1 \times 10^6$ $GD2^+$ (A) or $1 \times 10^6$ $GD2^-$ (B) MDA-MB-231 cells expressing GFP were transplanted subcutaneously into NOD/SCID mice. Four weeks after transplantation, mice were sacrificed; tumors were dissected and digested into single cell suspension. The cells were stained with anti-GD2 antibody using indirect staining protocol and analyzed on flow cytometer. Dead cells were excluded by eliminating DAPI positive cells.
Figure 13A:
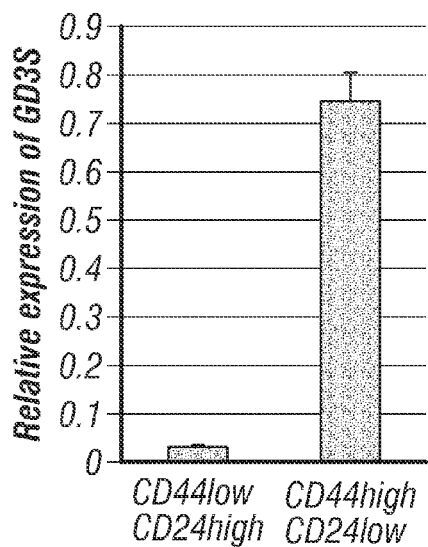
FIG. 13: $GD2^+$ cells express nestin. In an identical experiment to SF 3, mRNA from $HMLER-GD^{+/-}$ cells was analyzed for nestin expression by real-time RT-PCR.
Figure 13B:
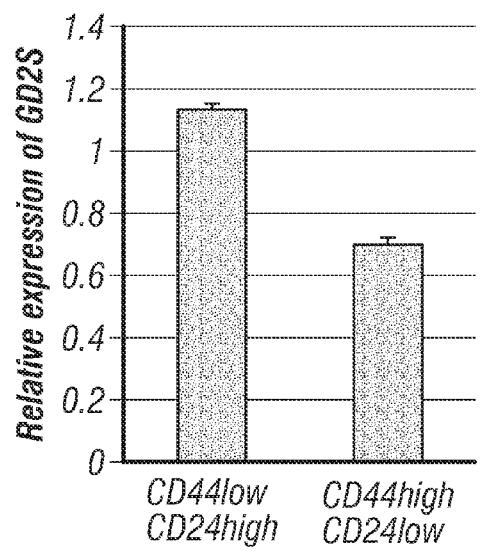

Among the genes differentially expressed between GD2$^+$ and GD2$^-$ populations, GD3 synthase (GD3S), a key enzyme involved in the biosynthesis of GD3 (an intermediate for GD2, FIG. 3C), was found to be upregulated ~9 fold in GD2$^+$ compared to GD2$^-$ cells (Table 2). The microarray data was validated by qRT-PCR (FIG. 3D). However, expression of the gene encoding GD2 synthase, which is involved in conversion of GD3 to GD2 is not altered (FIG. 3D). Expression of a number of genes involved in migration and invasion including matrix metalloproteinases (MMPs) (MMP-2, MMP-7 and MMP19) and EMT associated markers, including N-cadherin and vimentin, are expressed at higher levels, whereas E-cadherin is expressed at low levels in GD2$^+$ cells (Table 2). These findings were confirmed by qRT-PCR (FIG. 11). In addition, CD44 mRNA is up- and CD24 mRNA is down-regulated in GD2$^+$ relative to GD2$^-$ cells, which was confirmed by FACS analysis (FIG. 2A). In addition, the stem cell marker nestin was also found to be upregulated in GD2$^+$ cells compared to GD2$^-$ cells (FIG. 12). These and other genes that were differentially expressed in GD2$^+$ vs. GD2$^-$ cells are listed in Table 11. Conversely, similar to the GD2$^+$ cells, the GD3S is overexpressed more than 10 fold in CD44$^{high}$CD24$^{low}$ compared to CD4$^{low}$/CD24$^{high}$ cells (FIG. 13), but no significant difference was found in the expression of GD2S between CD44$^{high}$/CD24$^{low}$ and CD4$^{low}$/CD24$^{high}$ cells. This again demonstrates that the expression of GD3S and GD2 strongly correlates with the CD44$^{high}$CD24$^{low}$ phenotype. Similar to HMLER cells, GD2$^+$ cells from MDA-MB-231 cells expressed GD3S more than 5 fold higher than to GD$^-$ cells and consistently no significant differences in GD2S expression are observed (FIG. 3E).

TABLE 11

List of genes that were differentially expressed in GD2$^+$ cells compared to GD2$^-$ cells

| Gene name | Full name | Affymetrix probe ID | Fold change |
|---|---|---|---|
| Lumican | Lumican | 201744_s_at | 29.0 |
| PDGFRA | Platelet derived growth factor receptor-alpha | 203131_at | 27.25 |
| ZEB1 | zinc finger E-box binding homeobox 1 | 239952_at | 25.46 |
| Collagen III | Collagen type III | 215076_s_at | 23.4 |
| Collagen I | Collagen type I | 202310_s_at | 21.9 |
| ST8SIA1 | GD3 synthase | 210073_at | 18.29 |
| VCAM1 | vascular cell adhesion molecule 1 | 203868_s_at | 12.8 |
| N-cadherin | Cadherin 2 | 203441_s_at | 11.7 |
| NCAM1 | Neural cell adhesion molecule 1 | 229799_s_at | 10.15 |
| IL8 | Interleukin8 | 211506_s_at | 8.4 |
| Nestin | Nestin | 218678_at | 7.9 |
| MMP2 | Matrix metallopeptidase 2 | 201069_at | 7.5 |
| Twist1 | twist homolog 1 (*Drosophila*) | 213943_at | 6.5 |
| Fibronectin | Fibronectin | 1558199_at | 6.1 |
| Vimentin | Vimentin | 1555938_x_at | 5.3 |
| MMP7 | Matrix metallopeptidase 7 | 204259_at | 4.8 |
| BST2 | Bone marrow stromal cell antigen 2 | 201641_at | 4.8 |
| MMP19 | Matrix metallopeptidase 19 | 204575_s_at | 4.7 |
| NOTCH3 | Notch homolog 3 | 203238_s_at | 4.0 |
| CD44 | CD44 | 212063_at | 3.0 |
| Myosin | Myosin | 212338_at | −8.7 |
| LAMC2 | Laminin | 207517_at | −13.0 |
| IL1A | interleukin 1, alpha | 210118_s_at | 13.5 |
| GJB3 | Gap junction protein, beta 3, 31 kDa | 215243_s_at | −14.2 |
| FGFR3 | Fibroblast growth factor receptor 3 | 204379_at | −17.7 |
| ITGB6 | Integrin, beta 6 | 226535_at | 24.84 |
| CD24 | CD24 | 208651_x_at | −20 |
| E-cadherin | E-cadherin | 201131_s_at | −29.8 |
| EPCAM | Epithelial cell adhesion molecule | 201839_s_at | −44.5 |

Example 6—GD2$^-$ Cells can Spontaneously Generate GD2$^+$ Cells

Figure 4A:
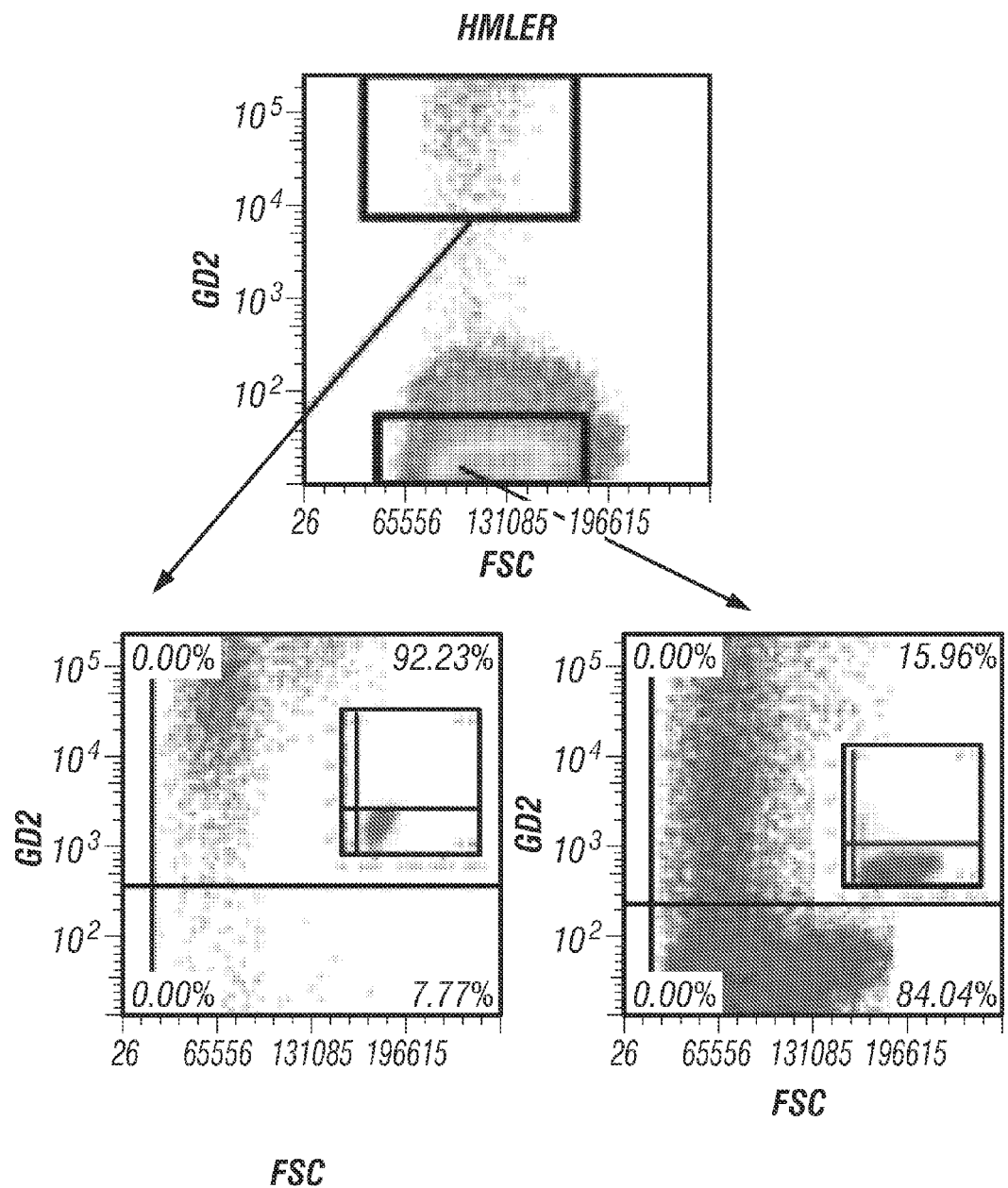
FIG. 4: GD2 Depleted Cells are Able to Generate $GD2^+$ Cells in Culture: A possible role of EMT. (A&B) $GD2^{+/-}$ cells from HMLER (A) MDA-MB-231 (B) cells were FACS sorted and cultured in MEGM medium for 10 days. After incubation, the cells were stained with GD2 antibody (BD) and analyzed on an LSR-II flow cytometer. Note the re-generation of $GD^+$ cells in a GD2-depleted population. C. To determine the possible role of EMT, HMLER cells transduced with two known EMT inducers (Twist and Snail) stained with anti-GD2 antibody and analyzed on an LSR-II flow cytometer. Expression of GD2 is shown on the y-axis and forward scatter (FSC) on the x-axis. D. Graphic representation of percent of $GD2^+$ vector control or Twist- or Snail-transduced HMLER cells. (E&F) mRNA expression analysis of GD3 synthase (GD3S, E) and GD2 synthase (GD2S, F) in vector or Twist- or Snail-transduced cells was performed by real-time TaqMan RT-PCR.
Figure 4B:
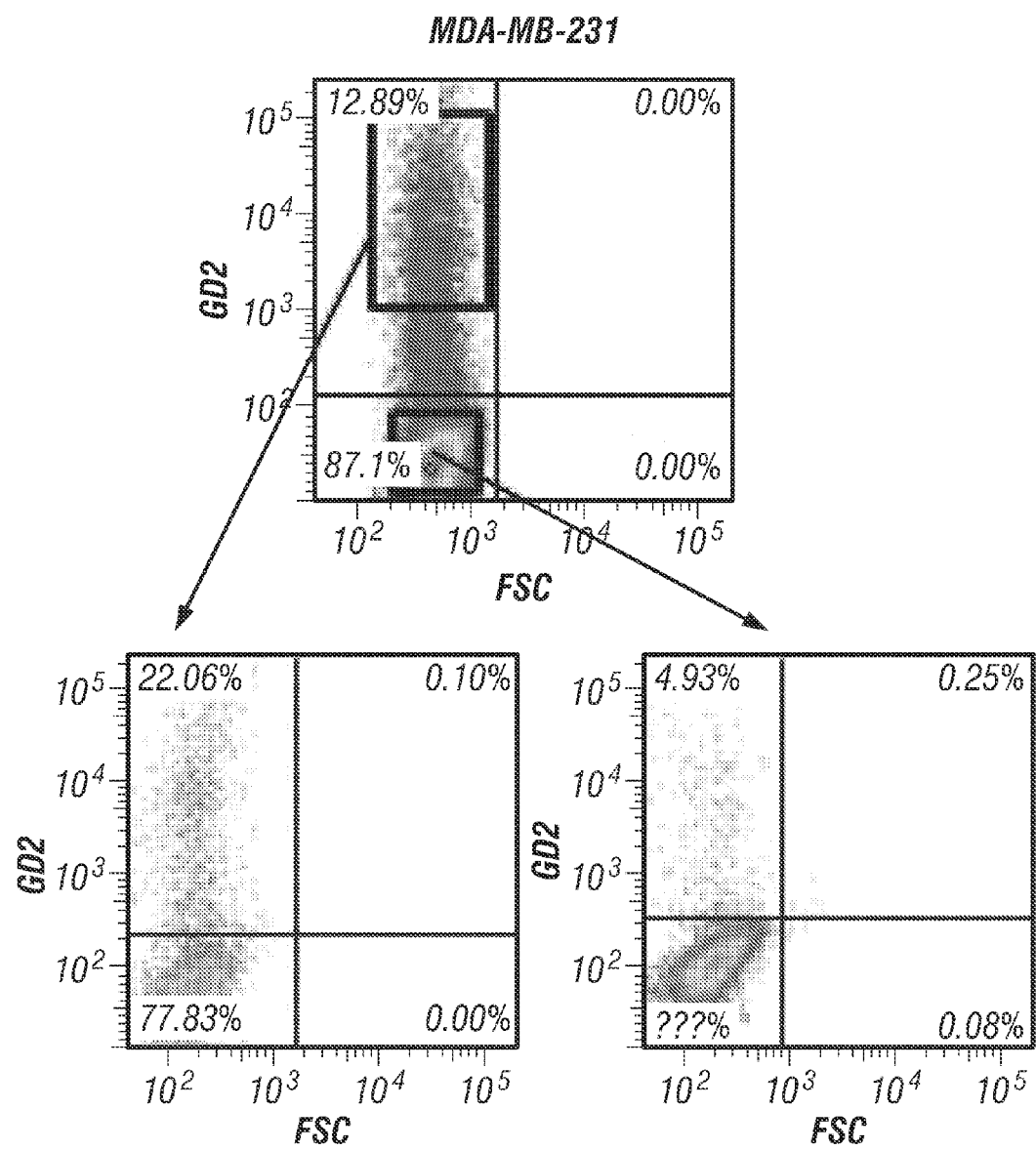
Figure 14A:
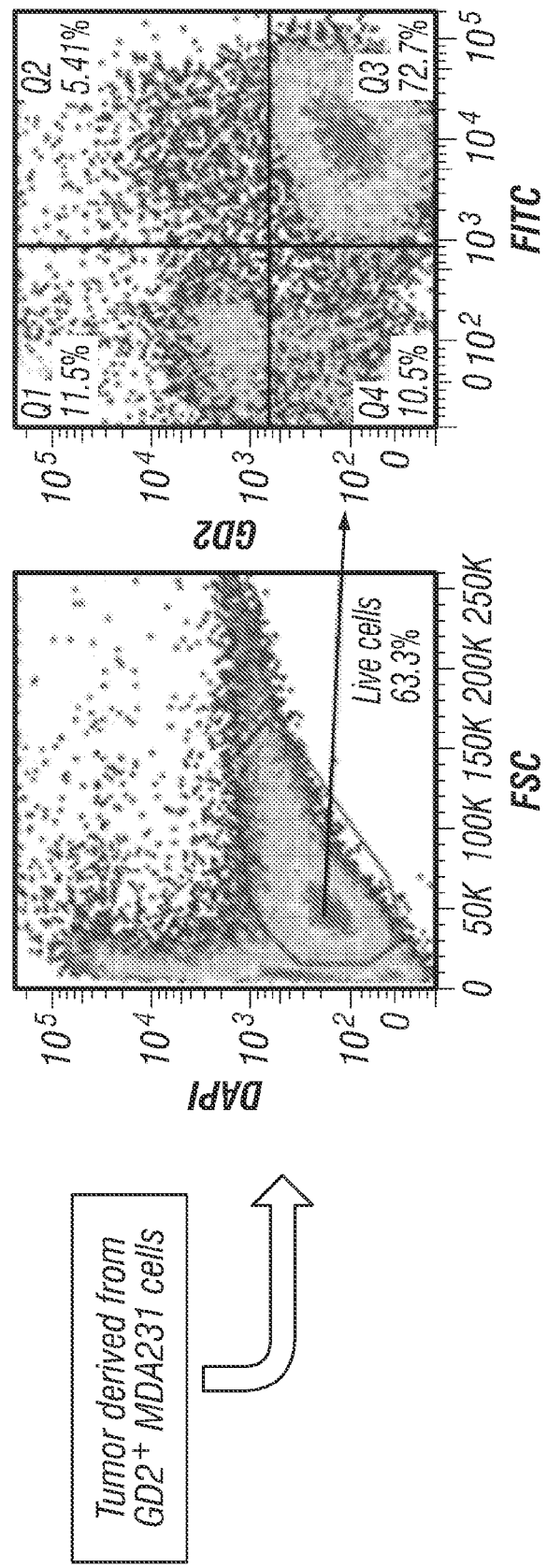
FIG. 14: $CD44^{high} CD24^{low}$ cells from HMLER express higher levels of GD3S. $CD44^{high}CD24^{low}$ and $CD44^{low}CD24^{high}$ cells from HMLER were cell sorted and mRNA was analyzed for the expression of GD3S (A) and GD2S (B) by real-time RT-PCR.
Figure 14B:
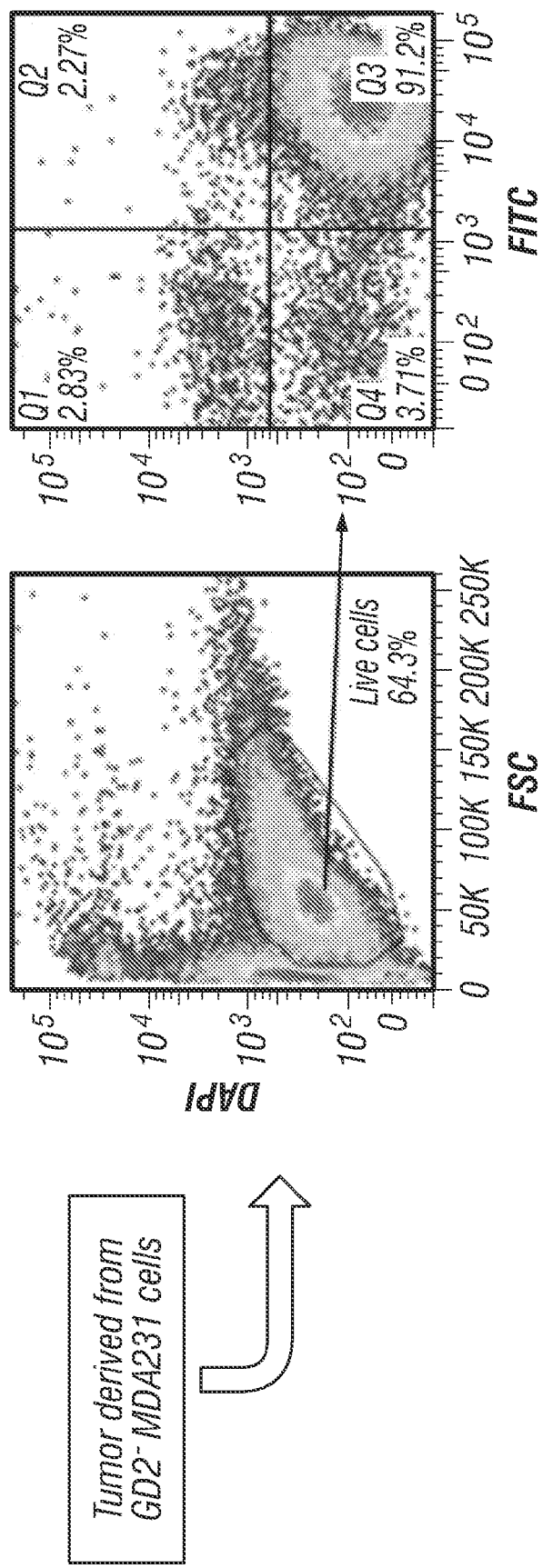

Since it was observed that only a 2 fold difference in mammosphere formation and 2-5 fold difference in tumor initiation between GD2$^+$ and GD2$^-$ populations, it was investigated whether this was due to the generation of GD2$^+$ cells from GD2$^-$ cells. In fact, GD2$^+$ and GD2$^-$ cells were sorted from HMLER (FIG. 4A) and MDA-MB-231 cells (FIG. 4B) and cultured in vitro for 12 days in their respective growth media. Surprisingly, ~10% of GD2$^+$ HMLERs had become GD2$^-$, and 15% of GD2$^-$ cells had spontaneously generated GD2$^+$ cells, and this proportion was almost identical to the unfractionated original HMLER cells (FIG. 4A). Similarly, the GD2$^+$ and GD2$^-$ cells from MDA MB 231 cells also generated 81 percent (81±2.5%) of GD2$^-$ and 12 percent of GD2$^+$ cells, respectively, again reflecting the percentage of GD2$^+$ cells within the parental MDA-MB-231 cell composition. To investigate the generation of GD2$^+$ cells from GD2$^-$ cells and vice versa in vivo, GFP labeled MDA-MB-231 cells were sorted into GD2$^+$ and GD2$^-$ and 1×10$^6$ GD2$^{-/+}$ cells were subcutaneously transplanted into NOD/SCID mice. Four weeks later the tumors were dissected and made into single cell suspension as described in methods. The cells were then stained with anti-GD2 antibody and analyzed using flow cytometer. It was found that the tumor generated by GD2$^+$ cells had nearly 91±4.5% of GD2$^-$ cells, whereas 2.4±1.1% of cells in GD2$^-$ derived tumors were positive for GD2. These findings indicate that the GD2$^+$ cells could spontaneously become GD2$^-$ cells and vice versa in vivo (FIGS. 14 A&B).

Example 7—Induction of EMT Generates GD2+ Cells

Figure 4C:
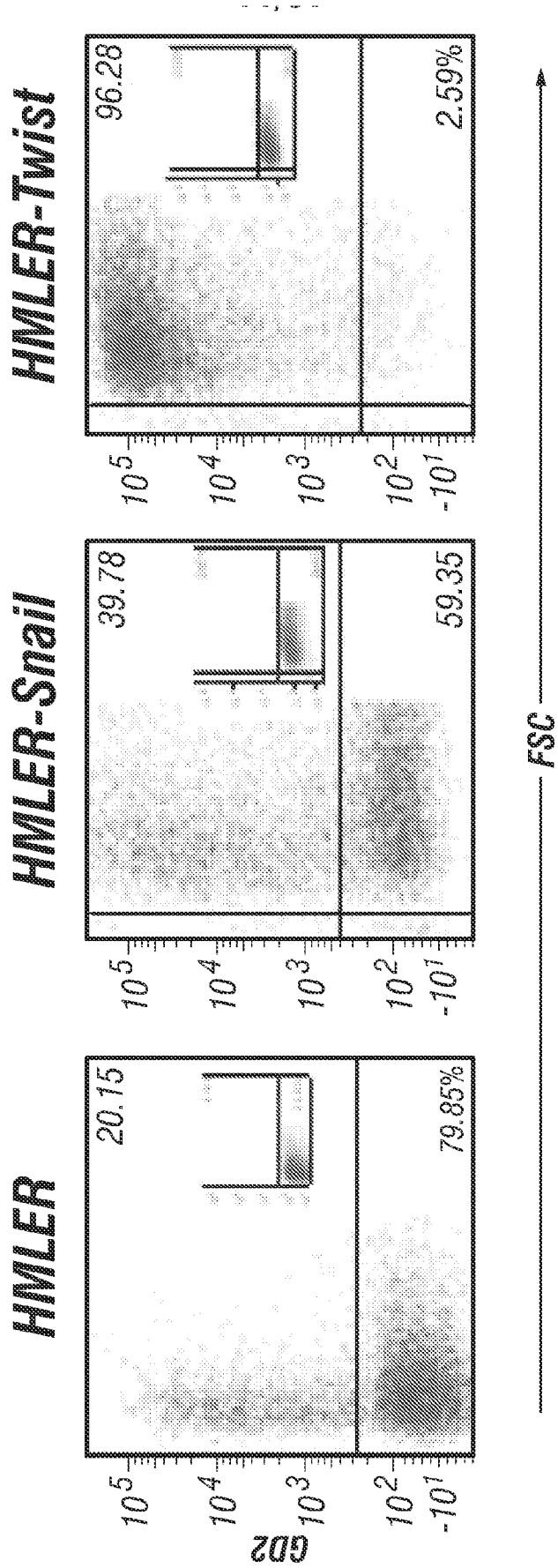

Since it was recently reported that the induction of EMT in HMLER cells results in the acquisition of stem cell properties (Mani et al., 2008), the expression of GD2 on HMLER cells induced to undergo EMT was also examined by the ectopic expression of either Twist or Snail. Strikingly, it was found that the induction of EMT by Snail or Twist resulted in significant increase in the percent of GD2+ populations from initial 18% (control) to 40% in HMLER-Snail cells and 100% in HMLER-Twist cells (FIGS. 4 C and D). Corroborating the previous data suggesting a correlation between GD3S and CSCs, it was also found that the expression of GD3S mRNA increased in the EMT-derived HMLER cells following induction of EMT by 2.5 fold in Snail cells and 8 fold in Twist cells (FIG. 4E), which correlates with the total percentage of GD2 positive cells in their respective population (40% in Snail and 100% in Twist cells). In contrast, no significant difference in the expression of GD2S (FIG. 4F) was found, reiterating the fact that GD3S is the key regulator in the biosynthesis of GD2.

Example 8—GD3S is Necessary for Cancer Stem Cell Properties

Figure 17A:
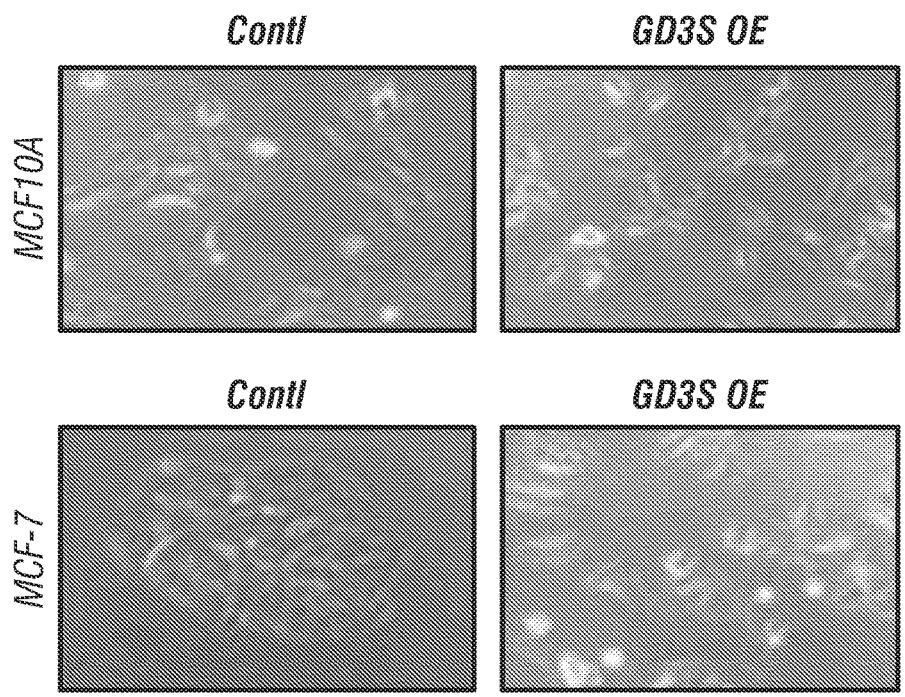
FIG. 17: GD3S induces EMT. MCF-10A and MCF7 cells were transduced with lentivirus to stably express GD3S. Morphological examination (A) and gene expression studies (B) are consistent with induction of EMT by GD3S.
Figure 17B:
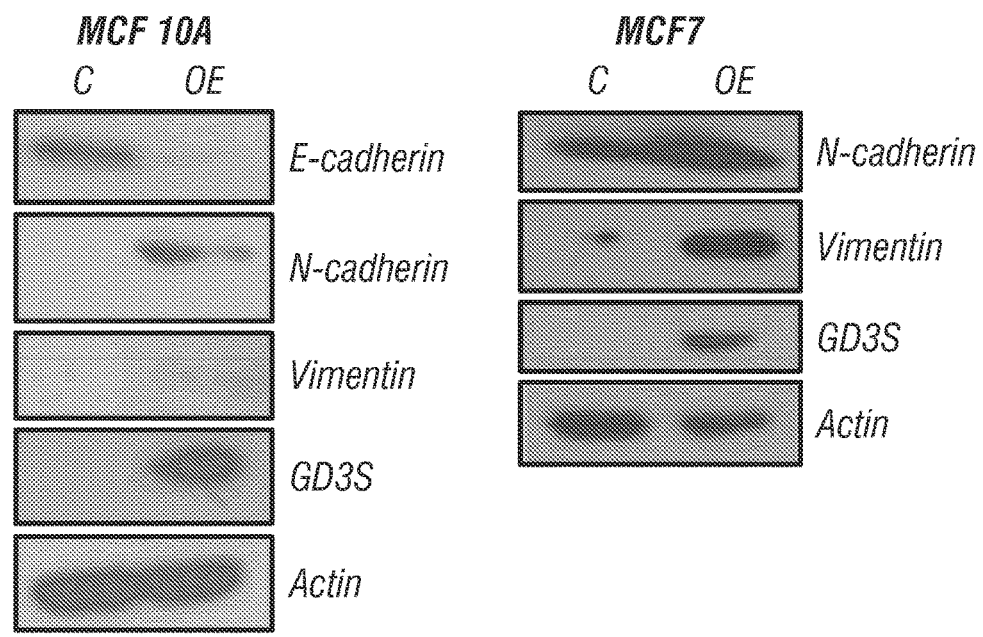

Although EMT has been shown to play an important role in cancer metastasis, key molecular factors responsible for this function have not been well defined. To examine the role of GD3S in EMT, GD3S was over-expressed in MCF-10A mammary epithelial cells and MCF7 breast cancer cells and tested for induction of EMT. Interestingly, significant changes in cell growth morphology and gene expression were observed in GD3S over-expressing (OE) cells (FIG. 17). GD3S-OE cells changed from cobblestone appearance to spindle shaped cells, whereas vector control cells continued to form cobblestone structures. In addition, protein expression data revealed that the EMT related genes N-cadherin and vimentin were up-regulated whereas E-cadherin was down-regulated in GD3S-OE cells compared to vector controls (FIG. 17). These results suggest that GD3S induces EMT in breast cancer cells. In an attempt to investigate the role of GD3S in breast cancer metastasis, the metastatic ability of GD3S knock-down MDA-MB-231 cells was tested in ~NOD/SCID experimental metastasis model. When cells were transplanted through the tail vein, an 80% reduction in pulmonary metastatic nodules that develop from GD3S-shRNA transduced cells was observed as compared to vector control cells. This indicates that GD3S is essential for the metastatic function of MDA-MB-231 cells. In-vivo bio-luminescence imaging in live mouse revealed that 4/5 mice transplanted with GD3S-KD cells showed no nodule formation in 1 tmg whereas, all mice transplanted with control shRNA treated cells metastasized to lungs and formed nodules.

Figure 5F:
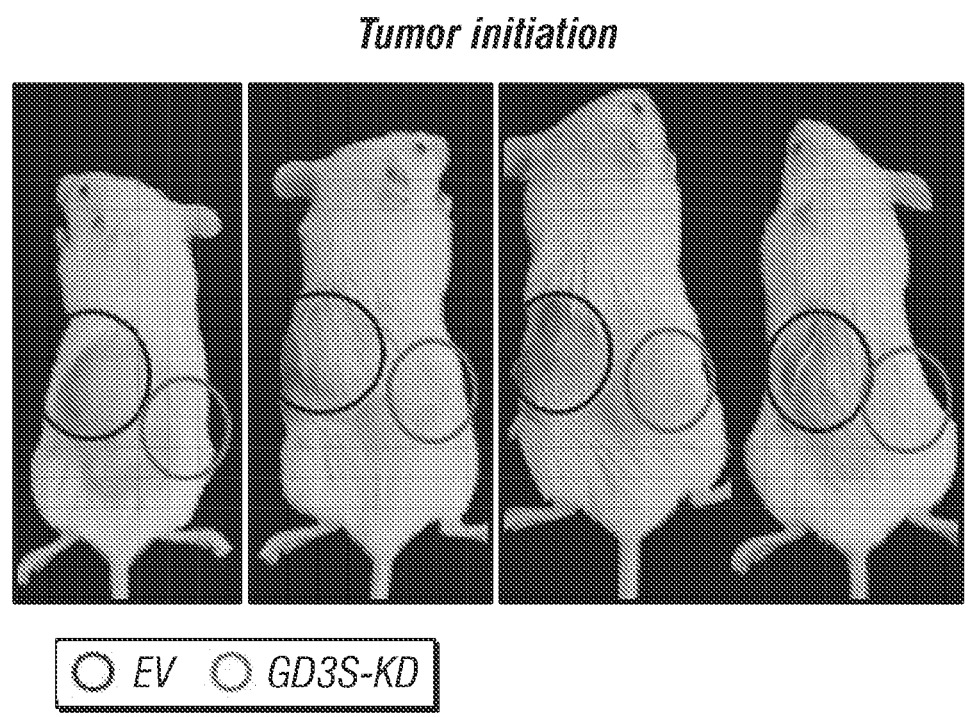
FIG. 5: Knockdown of GD3S Reduces Cell Proliferation, Mammosphere Formation, and Tumor Initiation in MDA-MB-231 Cells. (A) To measure knockdown of GD3S, vector control or GD3S-KD MDA231 cells were analyzed for mRNA expression of GD3S by real-time TaqMan RT-PCR. Relative expression of GD3S is shown in the bar graph. (B) To measure levels of GD2 on the cell surface, vector control or GD3S-KD MDA231 cells were stained with anti-GD2 antibody and analyzed on an LSR-II flow cytometer (BD). GD2 expression is shown on the y-axis and forward scatter (FSC) on the x-axis. (C) Graphic representation of the percentage of $GD2^+$ cells in vector control and GD3S-KD-MDA231 cells. (D) To measure cell migration, vector control and GD3S-KD-MDA231 cells were cultured in the presence or absence of 30% serum in a trans-well migration chamber. The average number of cells per microscopic field was shown in a bar graph. (E) Mammosphere formation assay using either vector control or GD3S-KD-MDA231 cells was performed by seeding 1,000 cells per well in 24-well cell culture dishes containing mammosphere growth medium. After 10 days, the mammospheres were counted under a light microscope. Graphic representation of mammospheres formed from either vector control or GD3S-KD-MDA231 cells. (F) To examine tumor initiation potential, $1 \times 10^6$ vector control or GD3S-KD-MDA231 cells were transplanted subcutaneously into flanks NOD/SCID mice. At the end of the 9th week, mice were shaved to remove excess hair on the tumors and photographs were taken. (G) The tumors size was measured between 4-9 weeks
Figure 5G:
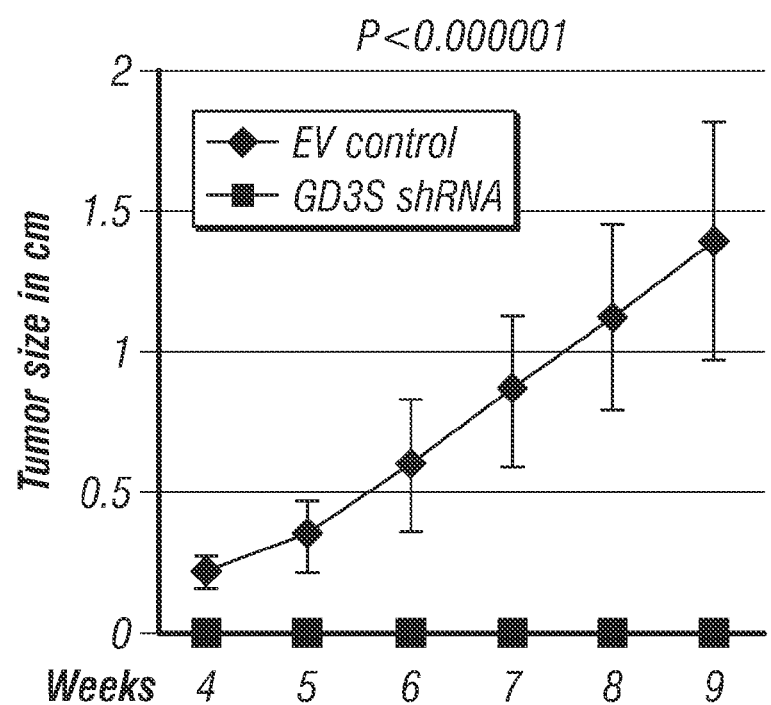
Figure 15A:
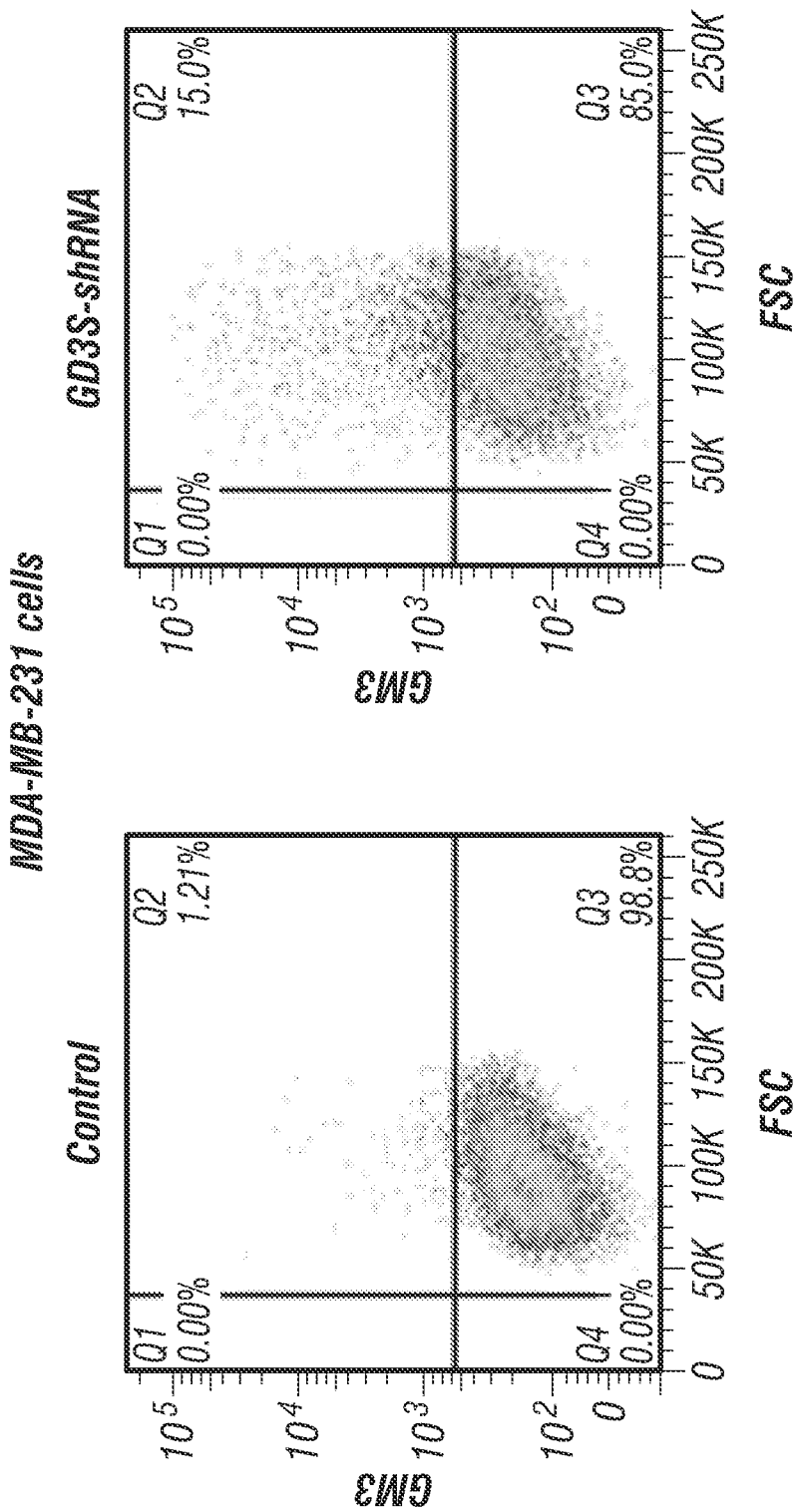
FIG. 15: Knock-down of GD3S enhances the expression of GM3 ganglioside. (A) MDA-231 cells that were transduced with either GD3S or control sh-RNA were stained with anti-GM3 antibody by indirect staining method. Data was analyzed on LSR-II flow cytometer. (B) Bar graph showing the percent of GM3 positive cells in GD3S knock-down and control MDA-MB-231 cells.
Figure 15B:
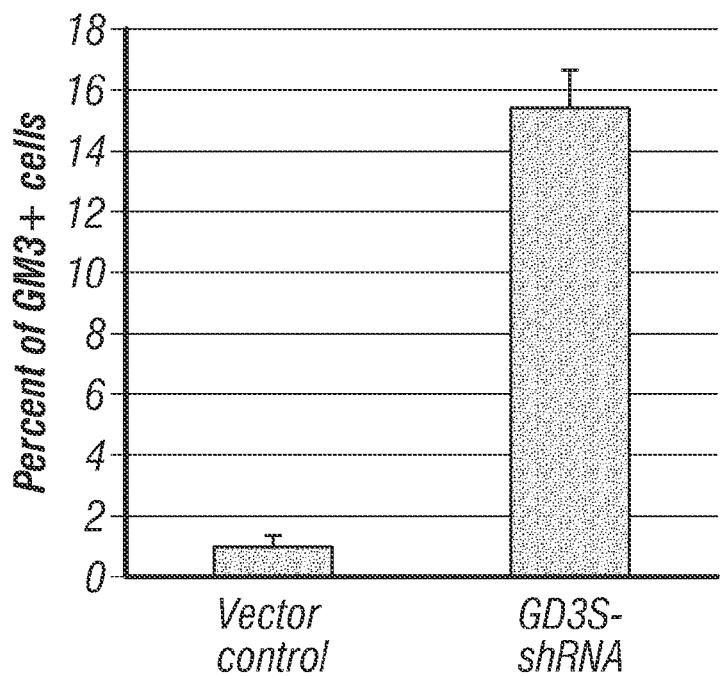

To investigate the functional role of GD2 in cancer stem cells, the expression of GD3S, the critical enzyme involved in the biosynthesis of GD2 in MDA-MB-231 cells was suppressed using a lentiviral-based shRNA expression vector and obtained more than 80 percent knockdown (FIG. 5A). As expected, GD3S knockdown reduced the percentage of GD2+ cells from 12.3% (12.3±1.7%) to 5.5% (5.5±0.8%) in MDA-MB-231 cells (FIGS. 5B and C). Since GD3S is known to regulate a-series gangliosides including GM3, it was tested if knockdown of GD3S could induce the expression of GM3 in MDA-MB-231 cells. Flow cytometric analysis revealed that expression of GM3 was increased from 0.4%±0.3% (control cells) to 15%±1.4% (GD3S knock-down cells) suggesting that the knockdown of GD3S is efficient in these cells (FIGS. 15 10A&B). In addition functional analysis revealed that, GD3S-KD-MDA231 cells were ~3 fold less migratory in trans-well Matrigel invasion assays (FIG. 5D), and formed 3 fold less mammospheres compared to the controls (FIG. 5E). To further investigate the effects of suppression of GD3S on tumor formation, MDA-MB-231 cells expressing either control-shRNA or the GD3S-shRNA were subcutaneously injected into the flank of NOD/SCID mice. Strikingly, even after eight weeks, 1 million of GD3S-shRNA cells had not formed tumors, whereas the control shRNA cells had formed tumors in 4 out of 4 mice (FIG. 5F). The growth rate (tumor size) was also dramatically altered, as plotted in FIG. 5G.

Example 9—Triptolide, a Small Molecule Inhibitor, Inhibits GD3S Expression and Cancer Stem Cell Properties Triptolide, a small molecule anti-inflammatory drug, has been shown to inhibit GD3S in a melanoma cancer cell line (Kwon et al., 2010). Therefore, it was investigated whether triptolide could inhibit GD3S in breast cancer cell lines as well. MDA-MB-231 and Sum159 cells were treated with different concentrations of triptolide for 24 hr. Triptolide inhibited GD3S mRNA expression in both cell types in a dose dependent manner, with >95% inhibition at 125 nM (FIG. 6A, B). To test whether inhibition of GD3S by triptolide also inhibited GD2 expression, MDA-MB-231 cells were treated with different concentration of triptolide for either 24 or 48 hours. Absolute cell counts were measured using flow cytometer and found a dose dependent and time dependent decrease of GD2+ cells after triptolide treatment, indicating the successful inhibition of GD3S by triptolide (FIG. 6C).

Figure 16:
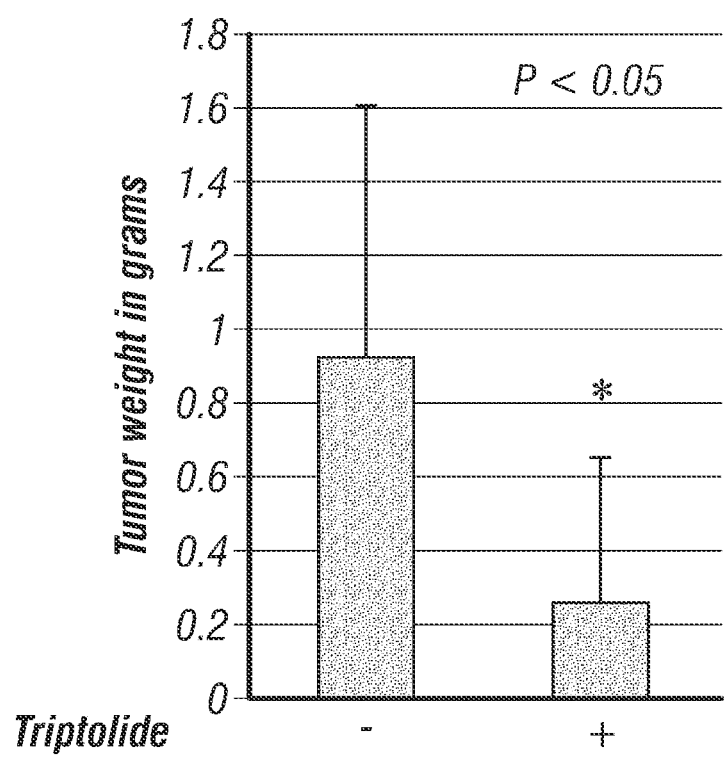
FIG. 16: Triptolide treatment reduces tumor mass in NOD-SCID mice. The experiment was performed as described in FIG. 6D. At the end of the experiment, tumors from control and triptolide treated mice dissected after killing the mice. The weight of the tumors were measured and plotted in a bar graph ($p<0.01$).

To further examine whether Triptolide could also inhibit tumor growth in vivo, $1 \times 10^6$ MDA-MB-231 cells were subcutaneously introduced into NOD-SCID mice (two injections per mouse and four mice per group). After the tumors reached 50 mm$^3$, the mice were randomly divided into two groups, and half of the mice treated with triptolide (0.15 mg/kg/day) while the other half were treated with PBS (control mice) every day by intraperitoneal injections. Interestingly, after 4 weeks, triptolide treated animals showed a dramatic decrease in tumor growth compared to control mice. Fifty percent of triptolide treated breast tumors were completely tumor free and there was reduction in tumor volume by >8-fold in 25% of mice (FIG. 6D). In addition, tumors in triptolide treated mice were 3-fold smaller in size and 4-fold lighter by weight (FIG. 6E, FIG. 16). Moreover, in a repeat, identical experiment, triptolide significantly prolonged survival of the treated mice (Log-rank, control vs triptolide, p=0.0015) (FIG. 6F). These findings indicate that GD3S plays a major role in regulating GD3S expression and the resulting GD2+ population. Specifically, it affects cell proliferation and tumor initiation of GD2+ breast cancer cells and when inhibited, greatly diminishes tumor growth and increases metastasis free survival of breast cancer bearing mice.

Discussion

The ganglioside GD2 was identified as a novel marker for breast cancer stem cells. Specifically, GD2+ cells displayed stem cell properties similar to those of the CD44$^{high}$/CD24$^{low}$ population. GD2 was found to be expressed predominantly in the CD44$^{high}$CD24$^{low}$ fraction isolated from breast cancer cell lines and primary patient breast cancer cells. In addition, the gene expression signature derived from GD2+ cells correlates strikingly with that obtained from CD44$^{high}$/CD24$^{low}$ cells. Moreover, inhibition of GD2 production using either shRNA against GD3 synthase (GD3S) or a small molecule inhibitor of GD3S (triptolide) resulted in significant reduction in the number of total GD2+ cells as well as in CSC-associated properties. Collectively, these results indicated that GD2 can be used in place of CD44$^{high}$/CD24$^{low}$ phenotype for the identification and/or purification of CSCs and, unlike the phenotype, can be targeted with small molecule or shRNA inhibitors of its regulator GD3S.

Of note, most of the basal-breast cancer cell lines used in this study displayed a higher percentage of GD2+ cells than the luminal-derived breast cancer cell lines. This observation is in line with the clinical observation of the more aggressive phenotype of basal-like vs luminal breast cancer (Sorlie et al., 2001). CD44, apart from being a mesenchymal marker, also serves as a prognostic marker for metastatic breast cancer (Orian-Rousseau, 2010; Seiter et al., 1993). Microarray analysis of GD2+ cells showed that mesenchymal markers including N-cadherin, vimentin, and fibronectin and the stem cell marker nestin were highly expressed in these cells; in addition, epithelial markers including E-cadherin and CD24 were downregulated, supporting the mesenchymal nature of these cells. In addition, the observation that GD2 expression correlates with CD44 expression, that GD2+ cells appear mesenchymal and that GD3S expression is induced during EMT indicates that the GD2/GD3S pathway could be used to diagnose and treat tumors that are CSC enriched and contain cells that have undergone EMT.

Induction of EMT in HMLER cells using either Snail or Twist resulted in mesenchymal appearance as well as in increased expression of GD2. Conversely, GD2+ cells isolated from HMLER cells displayed mesenchymal morphology. This suggests that both, EMT-derived and prexisting CSCs, seem to express GD2 and that the inhibition of GD2 production by shRNA against GD3S or by triptolide may inhibit CSCs independent of the mechanism of this inhibition.

Tumor cells, when cultured in vitro tend to maintain a small percentage of GD2+ cells. Moreover, fractionated GD2− cells generate GD2+ cells when cultured in vitro. This indicates that cancer cells acquire stem cell capacity through dedifferentiation from differentiated cancer cells probably via EMT. The finding that spontaneous generation of GD2+ cells from GD2− cells of HMLER or MDA-MB-231 cells is in line with recent reports that cancer cells acquire stem cell capacity through dedifferentiation from differentiated cancer cells and vice versa (Quintana et al., 2010).

It was noted that GD3S, but not GD2S correlates with GD2 expression even though GD2S is the immediate enzyme responsible for the conversion of GD3 to GD2. Further analysis indicates that only GD3S—but not GD2S-mRNA expression was regulated during EMT. Moreover, Dae et al. found that ZEB1, a known EMT inducing transcription factor directly binds to the GD3S promoter and induces transcription of GD3S in glioblastoma cells (Dae et al., 2009). These findings suggest that, the EMT inducing factors such as ZEB1 might bind to the GD3S promoter and up regulate its expression in CSCs as well as in EMT-derived cancer cells, which then generate GD3, due to the high basal expression of GD2S in these cells, which probably immediately converts to GD2 by ubiquitously expressed GD2S.

GD2 could serve as a potential marker for CSCs in other tumor types in addition to breast cancer and may possibly constitute a therapeutic target. Collectively, these findings indicate that GD2 and GD3S could identify cancer stem cells in breast cancer, and that therapeutic intervention of GD2 biosynthesis by targeting GD3S may serve as a novel means to inhibit CSC associated tumor growth, relapse, chemotherapy resistance and tumor metastasis.

Example 10—GD3S Inhibitors

Molecular modeling was used to identify candidate GD3S inhibitors. Such inhibitors are contemplated for use in reducing proliferation and/or inducing cell death in cancer cells, in particular in cancer stem cells, such as GD2-expressing cells.

A first set of candidate GD3S inhibitors have a general structure according to:

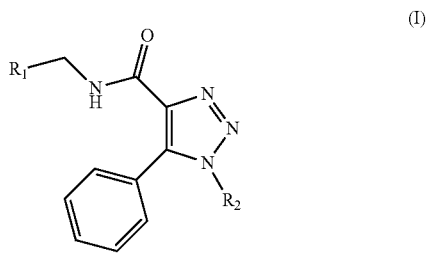

(I)

Examples of $R_1$ and $R_2$ side chains include alkyl, alkenyl, aryl, aralkyl or heteroaryl. In some cases, the $R_1$ group is provided by substitution of one of the compounds from Table 3 at this position. Likewise, in some cases, the $R_2$ group is provided by substitution of one of the compounds from Table 4 at this position. Some specific GD3S inhibitor candidates having the general structure of (I) are provided in Tables 5.

A first set of candidate GD3S inhibitors have a general structure according to:

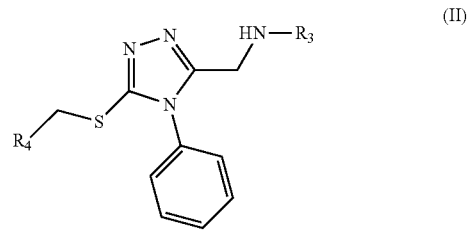

(II)

Examples of $R_3$ and $R_4$ side chains include alkyl, alkenyl, aryl, aralkyl or heteroaryl groups. In some cases, the $R_3$ group is provided by substitution of one of the compounds from Table 6 at this position. Likewise, in some cases, the $R_4$ group is provided by substitution of one of the compounds from Table 7 at this position. Some specific GD3S inhibitor candidates having the general structure of (II) are provided in Tables 8.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509
U.S. Pat. No. 4,675,287
U.S. Pat. No. 4,938,948
U.S. Pat. No. 5,021,236
U.S. Pat. No. 5,208,020
U.S. Pat. No. 6,333,410
U.S. Pat. No. 6,506,559
U.S. Pat. No. 6,573,099
U.S. Pat. No. 6,673,611
U.S. Pat. No. 7,276,497
U.S. Patent Publn. 2002/0168707
U.S. Patent Publn. 2003/0051263
U.S. Patent Publn. 2003/0055020
U.S. Patent Publn. 2003/0159161
U.S. Patent Publn. 2004/0019001
U.S. Patent Publn. 2004/0064842
U.S. Patent Publn. 2004/0265839
U.S. Patent Publn. 20100317547
Al-Hajj et al., *Proc. Natl. Acad. Sci. USA*, 100:3983-3988, 2003.
Antibodies: A Laboratory Manual, Cold Spring Harbor Laboratory, 1988.
Battula et al., *Haematologica*, 94:173-184, 2009.
Battula et al., *Stem Cells*, 28:1435-1445, 2010.
Bertolini et al., *Proc. Natl. Acad. Sci. USA*, 106:16281-16286, 2009.
Cumber et al., *J. Immunology*, 149B:120-126, 1992.
Dae et al., *Acta Biochim. Biophys. Sin. (Shanghai)*, 41:237-245, 2009.
Elenbaas et al., *Genes Dev.*, 15:50-65, 2001.
Fillmore and Kuperwasser, *Breast Cancer Res.*, 10:R25, 2008.
Fishman and Brady, *Science*, 194:906-915, 1976.
Gentleman et al., *Genome Biol.*, 5:R80, 2004.
Hakomori, *Cancer Res.*, 56:5309-5318, 1996.
Irizarry et al., *Biostatistics*, 4:249-264, 2003.
Kelly et al., *Science*, 317:337, 2007.
Klipper-Aurbach et al., *Med. Hypotheses*, 45:486-490, 1995.
Konopleva et al., *Cancer Cell*, 10:375-388, 2006.
Kwon et al., *Exp. Mol. Med.*, 42:849-855, 2010.
Liu et al., *Cell Mol. Biol.*, 49(2):209-16, 2003.
Lloyd and Old, *Cancer Res.*, 49:3445-3451, 1989.
Mani et al., *Cell*, 133:704-715, 2008.
Martinez et al., *Blood*, 109:4245-4248, 2007.
Neve et al., *Cancer Cell*, 10:515-527, 2006.
Orian-Rousseau, *Eur. J. Cancer*, 46:1271-1277, 2010.
Pack et al., *Biochem.*, 31:1579-1584, 1992.
PCT Publn. WO 02/056835
Posse de Chaves and Sipione, *FEBS Lett.*, 584:1748-1759, 2009.
Quintana et al., *Cancer Cell*, 18:510-523, 2010.
Rey et al., *J. Cell Physiol.*, 225:73-83, 2010.
Rosen and Jordan, *Science*, 324:1670-1673, 2009.
Schatton et al., *Bioessays*, 31:1038-1049, 2009.
Seiter et al., *J. Exp. Med.*, 177:443-455, 1993.
Smyth, *Stat. Appl. Genet. Mol. Biol.*, 3:Article 3, 2004.
Song et al., *Nature Med.* 9:347-351, 2003.
Sonnino and Prinetti, *Adv. Exp. Med. Biol.*, 688:165-184, 2010.
Sorlie et al., *Proc. Natl. Acad. Sci. USA*, 98:10869-10874, 2001.
Soutschek et al., *Nature*, 432(7014):173-178, 2004.
Svennerholm, *J. Neurochem.*, 10:613-623, 1963.
Visvader and Lindeman, *Nat. Rev. Cancer*, 8:755-768, 2008.
Wadhwa et al., *Curr. Opin. Mol. Ther.*, 6(4):367-372, 2004.

The invention claimed is:

1. An in vitro method for detecting the presence of candidate cancer stem cells (CSCs) in a ganglioside GD2 negative cancer, characterized as a cancer composed of at least 90% GD2 negative cells, the method comprising a) obtaining a cell population from the GD2 negative cancer; b) contacting the population with an anti-GD2 antibody to detect the presence of GD2 positive cells, said GD2 positive cells being candidate CSCs; and c) contacting the GD2 positive cells detected in step b) with antibodies to CD44 and/or CD24 to detect the expression of CD44 and/or CD24 by the GD2 positive cells.

2. The method of claim 1, wherein the cancer is an epithelial cancer.

3. The method of claim 1, wherein the cancer is a breast cancer.

4. The method of claim 1, wherein detecting the presence of GD2 positive cells in the GD2 negative population comprises performing an ELISA, an immunoassay, a radioimmunoassay (RIA), an immunoradiometric assay, a fluoroimmunoassay, a chemiluminescent assay, a bioluminescent assay, thin layer chromatography (TLC), flow cytometry, positron emission tomography (PET), single photon emission computed tomography (SPECT) imaging or a microscopy assay.

5. A method of treating cancer in a patient having a GD2 negative cancer, said GD2 negative cancer being characterized as a cancer composed of at least 90% GD2 negative cells, the method comprising detecting the presence of candidate cancer stem cells in the patient's GD2 negative cancer by the method of claim 1 and administering a GD2-targeted therapy to the patient in an amount effective to inhibit proliferation of cancer stem cells in the patient.

6. An isolated compound having a structure according to:

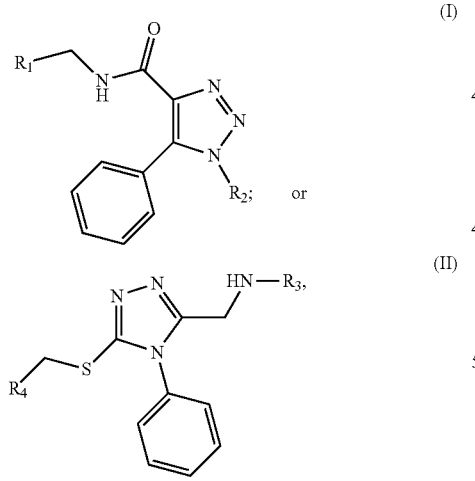

wherein $R_1$ is

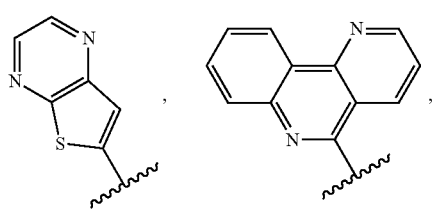

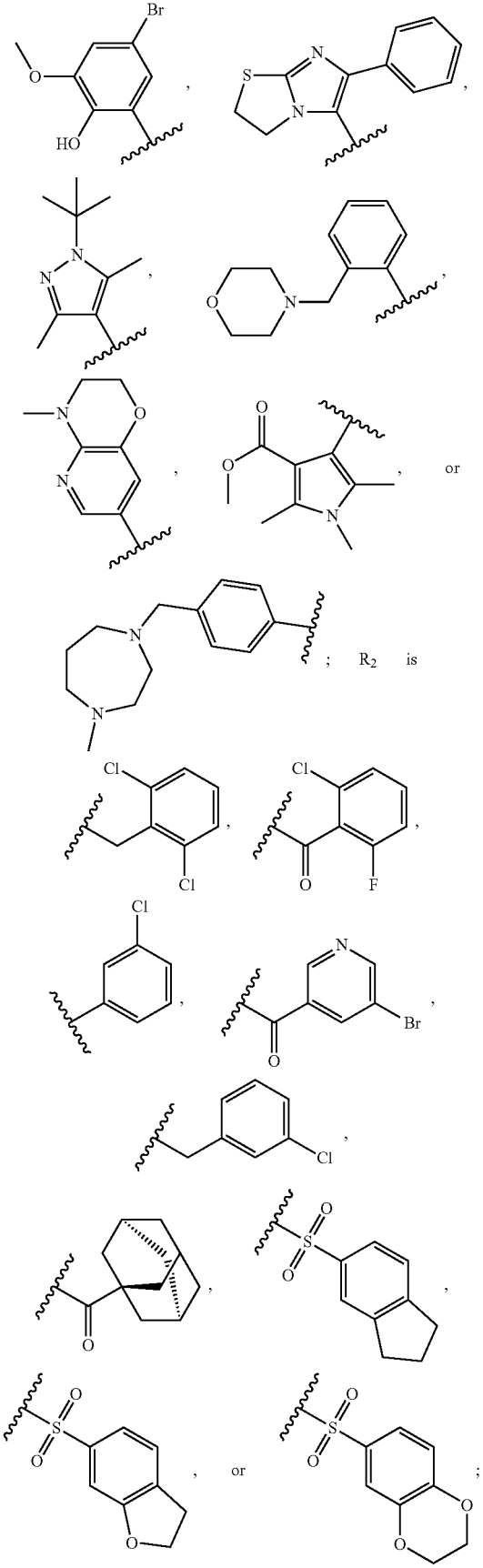

; $R_2$ is

-continued

R₃ is

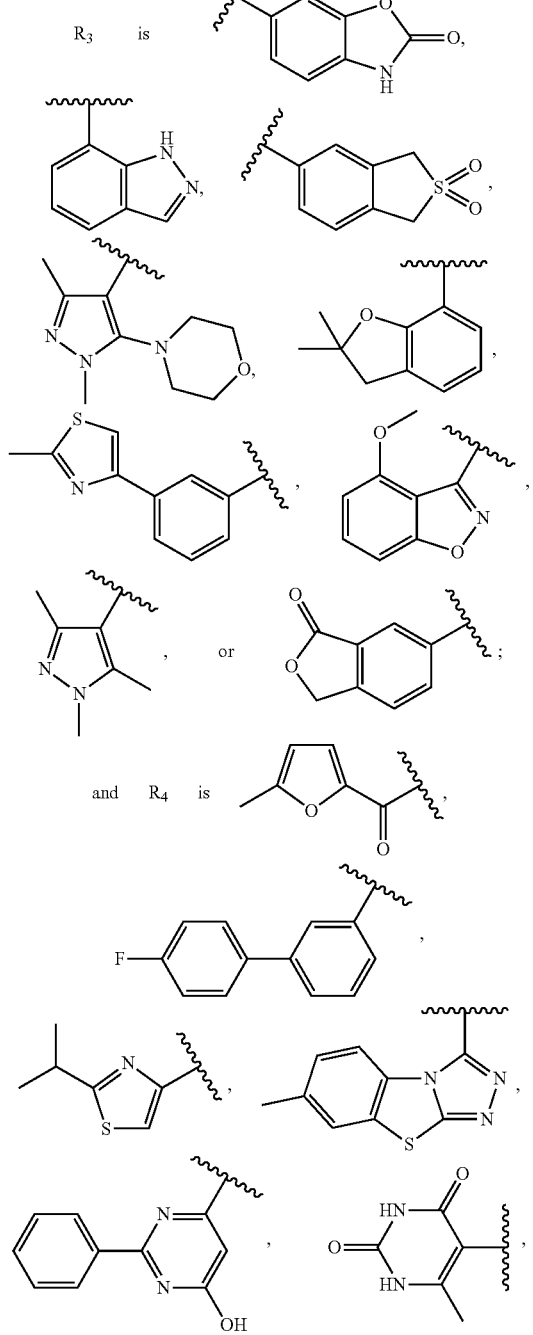

and R₄ is

-continued

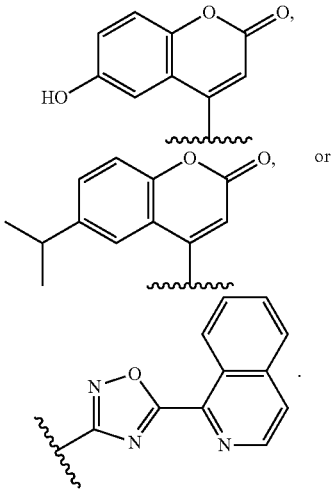

7. A composition comprising a compound according to claim 6 and pharmaceutically acceptable carrier.

8. A method of treating a patient having a cancer, wherein the cancer comprises cells that express GD2, comprising administering an effective amount of a compound of claim 6 to the patient.

9. The compound of claim 6, wherein the compound is selected from one of those in Table 5 or Table 8.

10. An isolated compound selected from Table 9.

11. A composition comprising a compound of claim 10 and a pharmaceutically acceptable carrier.

12. A method of treating a patient having a cancer, wherein the cancer comprises cells that express GD2, comprising administering an effective amount of a compound of claim 10 to the patient.

13. A method of treating a patient having a ganglioside GD2 (GD2) negative cancer, characterized as a cancer composed of at least 90% GD2 negative cells, comprising:

(i) administering a chemotherapy or radiation therapy to the patient in an amount effective to inhibit proliferation of cancer cells in the patient;

(ii) detecting the presence of GD2 positive candidate CSCs in accordance with claim 1; and (iii) administering a GD2-targeted therapy to if the patient is determined to have said GD2 positive candidate CSCs.

* * * * *

UNITED STATES PATENT AND TRADEMARK OFFICE
CERTIFICATE OF CORRECTION

PATENT NO. : 9,846,160 B2
APPLICATION NO. : 14/380807
DATED : December 19, 2017
INVENTOR(S) : Venkata Battula et al.

Page 1 of 1

It is certified that error appears in the above-identified patent and that said Letters Patent is hereby corrected as shown below:

In Claim 6, Column 66, Lines 33-38, delete:

" 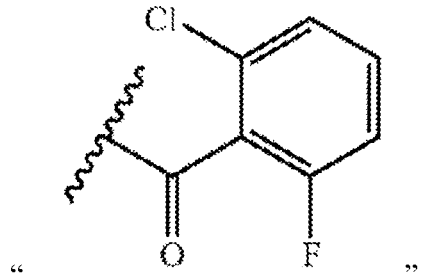 "

And insert:

-- 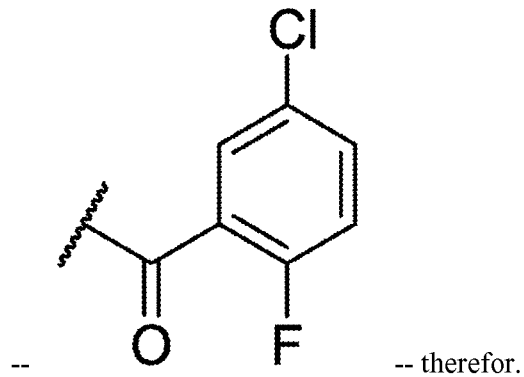 -- therefor.

Signed and Sealed this
Third Day of April, 2018

Andrei Iancu
*Director of the United States Patent and Trademark Office*